(12) United States Patent
Benjamin

(10) Patent No.: US 7,919,605 B1
(45) Date of Patent: Apr. 5, 2011

(54) NUCLEIC ACIDS, COMPOSITIONS AND METHODS FOR THE EXCISION OF TARGET NUCLEIC ACIDS

(75) Inventor: Kirsten R. Benjamin, Emeryville, CA (US)

(73) Assignee: Amyris, Inc., Emeryville, CA (US)

( * ) Notice: Subject to any disclaimer, the term of this patent is extended or adjusted under 35 U.S.C. 154(b) by 0 days.

(21) Appl. No.: 12/978,061

(22) Filed: Dec. 23, 2010

Related U.S. Application Data

(60) Provisional application No. 61/378,350, filed on Aug. 30, 2010.

(51) Int. Cl.
*C12N 15/11* (2006.01)
*C12N 1/19* (2006.01)
*C12N 15/70* (2006.01)

(52) U.S. Cl. .................. 536/23.1; 435/254.2; 435/471

(58) Field of Classification Search .................. None
See application file for complete search history.

(56) References Cited

U.S. PATENT DOCUMENTS

2005/0172365 A1 8/2005 Puchta et al.

OTHER PUBLICATIONS

Zeng, et al., *Current Biology*, (2009), 19:218-222.

*Primary Examiner* — Michele K Joike
(74) *Attorney, Agent, or Firm* — Jones Day

(57) ABSTRACT

Nucleic acids, compositions, and methods that allow for the excision of one or more loci from the genome of a host cell are provided herein. In particular, provided herein is an excisable nucleic acid construct comprising, in a 5' to 3' orientation: a first tandem repeat nucleic acid, a first homing endonuclease recognition site, a target nucleic acid, a second homing endonuclease recognition site, and a second tandem repeat nucleic acid. In some embodiments, the excisable nucleic acid construct is integrated into the host cell genome, and the target nucleic acid can be excised from the host cell genome by contacting the homing endonuclease recognition sites with one or more appropriate homing endonucleases.

20 Claims, 4 Drawing Sheets

SEQUENCE LISTING

```
<160> NUMBER OF SEQ ID NOS: 144

<210> SEQ ID NO 1
<211> LENGTH: 9
<212> TYPE: PRT
<213> ORGANISM: Artificial Sequence
<220> FEATURE:
<223> OTHER INFORMATION: Motif sequence for LAGLIDADG homing
      endonuclease

<400> SEQUENCE: 1

Leu Ala Gly Leu Ile Asp Ala Asp Gly
 1               5

<210> SEQ ID NO 2
<211> LENGTH: 6
<212> TYPE: PRT
<213> ORGANISM: Artificial Sequence
<220> FEATURE:
<223> OTHER INFORMATION: Motif sequence for GIY-YIG homing
      endonuclease

<400> SEQUENCE: 2

Gly Ile Tyr Tyr Ile Gly
 1               5

<210> SEQ ID NO 3
<211> LENGTH: 18
<212> TYPE: DNA
<213> ORGANISM: Artificial Sequence
<220> FEATURE:
<223> OTHER INFORMATION: Recognition sequence for I-SceI

<400> SEQUENCE: 3
tagggataac aggtaat                                                    18

<210> SEQ ID NO 4
<211> LENGTH: 31
<212> TYPE: DNA
<213> ORGANISM: Artificial Sequence
<220> FEATURE:
<223> OTHER INFORMATION: Recognition sequence for VDE (PI-SceI)

<400> SEQUENCE: 4
tatgtcgggt gcggagaaag aggtaatgaa a                                    31

<210> SEQ ID NO 5
<211> LENGTH: 24
<212> TYPE: DNA
<213> ORGANISM: Artificial Sequence
<220> FEATURE:
<223> OTHER INFORMATION: Recognition sequence for F-Cph

<400> SEQUENCE: 5
gatgcacgag cgcaacgctc acaa                                            24

<210> SEQ ID NO 6
<211> LENGTH: 24
<212> TYPE: DNA
<213> ORGANISM: Artificial Sequence
<220> FEATURE:
<223> OTHER INFORMATION: Recognition sequence for PI-MgaI (pps1)

<400> SEQUENCE: 6
gcgtagctgc ccagtatgag tcag                                            24
```

```
<210> SEQ ID NO 7
<211> LENGTH: 40
<212> TYPE: DNA
<213> ORGANISM: Artificial Sequence
<220> FEATURE:
<223> OTHER INFORMATION: Recognition sequence for PI-MtuII (pps1)

<400> SEQUENCE: 7
acgtgcacta cgtagagggt cgcaccgcac cgatctacaa                         40

<210> SEQ ID NO 8
<211> LENGTH: 20
<212> TYPE: DNA
<213> ORGANISM: Artificial Sequence
<220> FEATURE:
<223> OTHER INFORMATION: Directly repeated sequence (DR) s20M

<400> SEQUENCE: 8
aagatccgat cgaccgagaa                                               20

<210> SEQ ID NO 9
<211> LENGTH: 40
<212> TYPE: DNA
<213> ORGANISM: Artificial Sequence
<220> FEATURE:
<223> OTHER INFORMATION: Directly repeated sequence (DR) s40M

<400> SEQUENCE: 9
aagatccgat cgaccgagaa ctgagaacgg tgcaatgatc                         40

<210> SEQ ID NO 10
<211> LENGTH: 60
<212> TYPE: DNA
<213> ORGANISM: Artificial Sequence
<220> FEATURE:
<223> OTHER INFORMATION: Directly repeated sequence (DR) s60M

<400> SEQUENCE: 10
aagatccgat cgaccgagaa ctgagaacgg tgcaatgatc aacatgatct gcgacgagct   60

<210> SEQ ID NO 11
<211> LENGTH: 80
<212> TYPE: DNA
<213> ORGANISM: Artificial Sequence
<220> FEATURE:
<223> OTHER INFORMATION: Directly repeated sequence (DR) s80M

<400> SEQUENCE: 11
aagatccgat cgaccgagaa ctgagaacgg tgcaatgatc aacatgatct gcgacgagct   60
tgaggatgca aatggctgac                                               80

<210> SEQ ID NO 12
<211> LENGTH: 60
<212> TYPE: DNA
<213> ORGANISM: Artificial Sequence
<220> FEATURE:
<223> OTHER INFORMATION: Single sequence s60M

<400> SEQUENCE: 12
aagatccgat cgaccgagaa ctgagaacgg tgcaatgatc aacatgatct gcgacgagct   60

<210> SEQ ID NO 13
<211> LENGTH: 60
<212> TYPE: DNA
<213> ORGANISM: Artificial Sequence
<220> FEATURE:
```

<223> OTHER INFORMATION: s1x_hphA repeat sequence

<400> SEQUENCE: 13
cgttacgaag cacacactag ttagcgtcga gacacatagc gacgctagaa cttgcgactt    60

<210> SEQ ID NO 14
<211> LENGTH: 60
<212> TYPE: DNA
<213> ORGANISM: Artificial Sequence
<220> FEATURE:
<223> OTHER INFORMATION: s2x_hphA repeat sequence

<400> SEQUENCE: 14
gtactgccta gtagaaacgg atctccacgt actagagtcc acctggtatc tattagcccg    60

<210> SEQ ID NO 15
<211> LENGTH: 60
<212> TYPE: DNA
<213> ORGANISM: Artificial Sequence
<220> FEATURE:
<223> OTHER INFORMATION: s3x_kanA repeat sequence

<400> SEQUENCE: 15
cgaggattaa cgtgtaaggc cctaagctat gtaccgcatc tcctaagaga gtgtgaccca    60

<210> SEQ ID NO 16
<211> LENGTH: 60
<212> TYPE: DNA
<213> ORGANISM: Artificial Sequence
<220> FEATURE:
<223> OTHER INFORMATION: s4x_kanA repeat sequence

<400> SEQUENCE: 16
ttaatcagcg cccagagact agcactgaat gatcaacggg tagttcacac actgccagac    60

<210> SEQ ID NO 17
<211> LENGTH: 60
<212> TYPE: DNA
<213> ORGANISM: Artificial Sequence
<220> FEATURE:
<223> OTHER INFORMATION: s5x_natA repeat sequence

<400> SEQUENCE: 17
atggaatcac ggggctattc cacttgctaa taacgaggcg cttatcaacg gcgagcacat    60

<210> SEQ ID NO 18
<211> LENGTH: 60
<212> TYPE: DNA
<213> ORGANISM: Artificial Sequence
<220> FEATURE:
<223> OTHER INFORMATION: s6x_natA repeat sequence

<400> SEQUENCE: 18
agtcaaagcg cgattcgcta ggaatgagag cgagaacgaa ccggagtata tcacaatcgc    60

<210> SEQ ID NO 19
<211> LENGTH: 60
<212> TYPE: DNA
<213> ORGANISM: Artificial Sequence
<220> FEATURE:
<223> OTHER INFORMATION: s7x_URA3 repeat sequence

<400> SEQUENCE: 19
actagagcga aatggagagg tacgtgatcc tactagagcc cacgctatca tacagttggc    60

<210> SEQ ID NO 20

```
<211> LENGTH: 60
<212> TYPE: DNA
<213> ORGANISM: Artificial Sequence
<220> FEATURE:
<223> OTHER INFORMATION: s8x_URA3 repeat sequence

<400> SEQUENCE: 20
gtacgtccgt acttatgctg agcgctccta cacgaaaaac tcaccgtgac tagcataacg    60

<210> SEQ ID NO 21
<211> LENGTH: 20
<212> TYPE: DNA
<213> ORGANISM: Artificial Sequence
<220> FEATURE:
<223> OTHER INFORMATION: I-SceI primer sequence

<400> SEQUENCE: 21
gctagggata cagggtaat                                                 20

<210> SEQ ID NO 22
<211> LENGTH: 20
<212> TYPE: DNA
<213> ORGANISM: Artificial Sequence
<220> FEATURE:
<223> OTHER INFORMATION: I-SceI primer sequence

<400> SEQUENCE: 22
actagggata acaggtttat                                                20

<210> SEQ ID NO 23
<211> LENGTH: 50
<212> TYPE: DNA
<213> ORGANISM: Artificial Sequence
<220> FEATURE:
<223> OTHER INFORMATION: Directly repeated sequence (DR) xM0

<400> SEQUENCE: 23
aagatccgat cgaccgagaa ctgagaacgg tgcaatgatc aacatgatct               50

<210> SEQ ID NO 24
<211> LENGTH: 50
<212> TYPE: DNA
<213> ORGANISM: Artificial Sequence
<220> FEATURE:
<223> OTHER INFORMATION: Directly repeated sequence (DR) xM1

<400> SEQUENCE: 24
cgttacgaag cacacactag ttagcgtcga gacacatagc gacgctagaa               50

<210> SEQ ID NO 25
<211> LENGTH: 50
<212> TYPE: DNA
<213> ORGANISM: Artificial Sequence
<220> FEATURE:
<223> OTHER INFORMATION: Directly repeated sequence (DR) xM2

<400> SEQUENCE: 25
gtactgccta gtagaaacgg atctccacgt actagagtcc acctggtatc               50

<210> SEQ ID NO 26
<211> LENGTH: 50
<212> TYPE: DNA
<213> ORGANISM: Artificial Sequence
<220> FEATURE:
<223> OTHER INFORMATION: Directly repeated sequence (DR) xM3

<400> SEQUENCE: 26
```

```
cgaggattaa cgtgtaaggc cctaagctat gtaccgcatc tcctaagaga          50
```

```
<210> SEQ ID NO 27
<211> LENGTH: 50
<212> TYPE: DNA
<213> ORGANISM: Artificial Sequence
<220> FEATURE:
<223> OTHER INFORMATION: Directly repeated sequence (DR) xM4

<400> SEQUENCE: 27
ttaatcagcg cccagagact agcactgaat gatcaacggg tagttcacac          50
```

```
<210> SEQ ID NO 28
<211> LENGTH: 50
<212> TYPE: DNA
<213> ORGANISM: Artificial Sequence
<220> FEATURE:
<223> OTHER INFORMATION: Directly repeated sequence (DR) xM5

<400> SEQUENCE: 28
gaatcacggg gctattccac ttgctaataa cgaggcgctt atcaacggcg          50
```

```
<210> SEQ ID NO 29
<211> LENGTH: 50
<212> TYPE: DNA
<213> ORGANISM: Artificial Sequence
<220> FEATURE:
<223> OTHER INFORMATION: Directly repeated sequence (DR) xM6

<400> SEQUENCE: 29
gtcaaagcgc gattcgctag gaatgagagc gagaacgaac cggagtatat          50
```

```
<210> SEQ ID NO 30
<211> LENGTH: 50
<212> TYPE: DNA
<213> ORGANISM: Artificial Sequence
<220> FEATURE:
<223> OTHER INFORMATION: Directly repeated sequence (DR) xM7

<400> SEQUENCE: 30
actagagcga aatggagagg tacgtgatcc tactagagcc cacgctatca          50
```

```
<210> SEQ ID NO 31
<211> LENGTH: 50
<212> TYPE: DNA
<213> ORGANISM: Artificial Sequence
<220> FEATURE:
<223> OTHER INFORMATION: Directly repeated sequence (DR) xM8

<400> SEQUENCE: 31
gtacgtccgt acttatgctg agcgctccta cacgaaaaac tcaccgtgac          50
```

```
<210> SEQ ID NO 32
<211> LENGTH: 50
<212> TYPE: DNA
<213> ORGANISM: Artificial Sequence
<220> FEATURE:
<223> OTHER INFORMATION: Directly repeated sequence (DR) xM9

<400> SEQUENCE: 32
gcattaagtc gtagctagcg gattctctct tcgtgcatcc tagcaaatgg          50
```

```
<210> SEQ ID NO 33
<211> LENGTH: 2733
<212> TYPE: DNA
<213> ORGANISM: Artificial Sequence
<220> FEATURE:
```

<223> OTHER INFORMATION: RYSE 12 entry vector

<400> SEQUENCE: 33

```
gtaaaacgac ggccagtatt aaccctcact aaagggaact cgaggctctt cagctcacac      60
gcggccaggg ggagcctggc agactccata tgctatgcgg catcagagca gattgtactg     120
agagtgcacc atatgcggtg tgaaataccg cacagatgcg taaggagaaa ataccgcatc     180
aggcgccatt cgccattcag gctgcgcaac tgttgggaag ggcgatcggt gcgggcctct     240
tcgctattac gccagctggc gaaaggggga tgtgctgcaa ggcgattaag ttgggtaacg     300
ccagggtttt cccagtcacg acgttgtaaa acgacggcca gtgaattcga gctcggtacc     360
cggggatcct ctagcgtcga cctgcaggca tgcaagcttg cgtaatcat ggtcatagct      420
gtttcctgtg tgaaattgtt atccgctcac aattccacac aacatacgag ccggaagcat     480
aaagtgtaaa gcctggggtg cctaatgagt gagctaactc acattaattg cgttgcgcgc     540
tagcgagtca tccacgctcg tccaacgccg cggaccttg aagagcgagc tcccgctgag      600
caataactag cgtcatagct gtttcctggg tcgttcggct gcggcgagcg gtatcagctc     660
actcaaaggc ggtaatacgg ttatccacag aatcaggggga taacgcagga agaacatgt    720
gagcaaaagg ccagcaaaag gccaggaacc gtaaaaaggc cgcgttgctg gcgttttttcc    780
ataggctccg ccccctgac gagcatcaca aaaatcgacg ctcaagtcag aggtggcgaa      840
acccgacagg actataaaga taccaggcgt ttccccctgg aagctccctc gtgcgctctc     900
ctgttccgac cctgccgctt acccgatacc tgtccgcctt ctcccttcg ggaagcgtgg      960
cgctttctca tagctcacgc tgtaggtatc tcagttcggt gtaggtcgtt cgctccaagc    1020
tgggctgtgt gcacgaaccc cccgttcagc ccgaccgctg cgccttatcc ggtaactatc    1080
gtcttgattc caacccggta agacacgact tatcgccact ggcagcagcc actggtaaca    1140
ggattagcag agcgaggtat gtaggcggtg ctacagagtt cttgaagtgg tggcctaact    1200
acggctacac tagaagaaca gtatttggta tctgcgctct gctgaagcca gttaccttcg    1260
gaaaaagagt tggtagctct tgatccggca acaaaccac cgctggtagc ggtggttttt     1320
ttgtttgcaa gcagcagatt acgcgcagaa aaaaaggatc tcaagaagat cctttgatct    1380
tttctacggg gtctgacgct cagtggaacg aaaactcacg ttaagggatt ttggtcatga    1440
gattatcaaa aaggatcttc acctagatcc ttttaaatta aaaatgaagt tttaaatcaa    1500
tctaaagtat atatgagtaa cttggtcgca tgcttaccaa tgcttaatca gtgaggcacc    1560
tatctcagcg atctgtctat ttcgttcatc catagttgcc tgactgcccg tcgtgtagat    1620
aactacgata cgggagggct taccatctgg ccccagtgct gcaatgatac cgcgagaccc    1680
acgctcaccg gctccagatt tatcagcaat aaaccagcca gccggaaggg ccgagcgcag    1740
aagtggtcct gcaactttat ccgcctccat ccagtctatt aattgttgcc gggaagctag    1800
agtaagtagt tcgccagtta atagtttgcg caacgttgtt gccattgcta caggcatcgt    1860
ggtgtcacgc tcgtcgtttg gtatggcttc attcagctcc ggttcccaac gatcaaggcg    1920
agttacatga tcccccatgt tgtgcaaaaa agcggttagc tccttcggtc ctccgatcgt    1980
tgtcagaagt aagttggccg cagtgttatc actcatggtt atggcagcac tgcataattc    2040
tcttactgtc atgccatccg taagatgctt ttctgtgact ggtgagtact caaccaagtc    2100
attctgagaa tagtgtatgc ggcgaccgag ttgctcttgc ccggcgtcaa tacgggataa    2160
taccgcgcca catagcagaa ctttaaaagt gctcatcatt ggaaaacgtt cttcggggcg    2220
aaaactctca aggatcttac cgctgttgag atccagttcg atgtaaccca ctcgtgcacc    2280
```

| | |
|---|---:|
| caactgatct tcagcatctt ttactttcac cagcgtttct gggtgagcaa aaacaggaag | 2340 |
| gcaaaatgcc gcaaaaaagg gaataagggc gacacgaaaa tgttgaatac tcatcaattg | 2400 |
| cctttttcaa tattattgaa gcatttatca gggttattgt ctcatgagcg gttacatatt | 2460 |
| tgaatgtatt tagaaaaata aacaaatagg ggttccgcgc acatttcccc gaaaagtgcc | 2520 |
| acctgacgtc taagaaacca ttattatcat gacattaacc tataaaaata ggcgtatcac | 2580 |
| gaggcccttt catctcgcgc gtttcggtga tgacggtgaa aacctctgac acatgcagct | 2640 |
| cccggagaca gtcacagctt gtctgtaagc ggatgccggg agcagacaag cccgtcaggg | 2700 |
| cgcgtcagcg ggtgttggcg ggtgtcgggg ctg | 2733 |

<210> SEQ ID NO 34
<211> LENGTH: 1692
<212> TYPE: DNA
<213> ORGANISM: Artificial Sequence
<220> FEATURE:
<223> OTHER INFORMATION: xMarker ss60M.URA.I-SceI

<400> SEQUENCE: 34

| | |
|---|---:|
| aagatccgat cgaccgagaa ctgagaacgg tgcaatgatc aacatgatct gcgacgagct | 60 |
| tagggataac agggtaatat gcgtccatct ttacagtcct gtcttattgt tcttgatttg | 120 |
| tgccccgtaa aatactgtta cttggttctg cgcaggtatt ggatagttcc ttttttataaa | 180 |
| ggccatgaag cttttctttt ccaattttt tttttcgtc attatagaaa tcattacgac | 240 |
| cgagattccc gggtaataac tgatataatt aaattgaagc tctaatttgt gagtttagta | 300 |
| tacatgcatt tacttataat acagtttttt agttttgctg gccgcatctt ctcaaatatg | 360 |
| cttcccagcc tgcttttctg taacgttcac cctctacctt agcatccctt ccctttgcaa | 420 |
| atagtcctct tccaacaata ataatgtcag atcctgtaga gaccacatca tccacggttc | 480 |
| tatactgttg acccaatgcg tctcccttgt catctaaacc cacaccgggt gtcataatca | 540 |
| accaatcgta accttcatct cttccaccca tgtctctttg agcaataaag ccgataacaa | 600 |
| aatctttgtc actcttcgca atgtcaacag taccccttagt atattctcca gtagataggg | 660 |
| agcccttgca tgacaattct gctaacatca aaaggcctct aggttccttt gttacttctt | 720 |
| ctgccgcctg cttcaaaccg ctaacaatac ctgggcccac cacaccgtgt gcattcgtaa | 780 |
| tgtctgccca ttctgctatt ctgtatacac ccgcagagta ctgcaatttg actgtattac | 840 |
| caatgtcagc aaattttctg tcttcgaaga gtaaaaaatt gtacttggcg gataatgcct | 900 |
| ttagcggctt aactgtgccc tccatggaaa atcagtcaa gatatccaca tgtgttttta | 960 |
| gtaaacaaat tttgggacct aatgcttcaa ctaactccag taattccttg gtggtacgaa | 1020 |
| catccaatga agcacacaag tttgtttgct tttcgtgcat gatattaaat agcttggcag | 1080 |
| caacaggact aggatgagta gcagcacgtt cctatatgt agctttcgac atgatttatc | 1140 |
| ttcgtttcct gcaggttttt gttctgtgca gttgggttaa gaatactggg caatttcatg | 1200 |
| tttcttcaac accacatatg cgtatatata ccaatctaag tctgtgctcc ttccttcgtt | 1260 |
| cttccttctg ctcggagatt accgaatcaa aaaaatttca agaaaccgg aatcaaaaaa | 1320 |
| aagaacaaaa aaaaaaaga tgaattgaaa agctttatgg accctgaaac cacagccaca | 1380 |
| ttaaccttct tgatggtca aaacttatcc ttcaccataa atatgcctcg caaaaaggt | 1440 |
| aattaacata tatagaatta cattatttat gaaatatcat cactatctct tagcatcttt | 1500 |
| aatccttttc tacatcagat aacttcggtt tgttatcatc gtctgtattg tcatcaattg | 1560 |
| gcgcagtagc ctcaatttca acgtcgtttg actctggtgt ttgttcatgt gcagatccat | 1620 |

```
gagatgatga acaagatccg atcgaccgag aactgagaac ggtgcaatga tcaacatgat    1680
ctgcgacgag ct                                                        1692

<210> SEQ ID NO 35
<211> LENGTH: 1602
<212> TYPE: DNA
<213> ORGANISM: Artificial Sequence
<220> FEATURE:
<223> OTHER INFORMATION: RaBit12-0-M-555

<400> SEQUENCE: 35
gctcacacgc ggccaggggg agccgttcat catctcatgg atctgcacat gaacaaacac      60
cagagtcaaa cgacgttgaa attgaggcta ctgcgccaat tgatgacaat acagacgatg     120
ataacaaacc gaagttatct gatgtagaaa aggattaaag atgctaagag atagtgatga     180
tatttcataa ataatgtaat tctatatatg ttaattacct tttttgcgag gcatatttat     240
ggtgaaggat aagttttgac catcaaagaa ggttaatgtg gctgtggttt cagggtccat     300
aaagcttttc aattcatctt ttttttttt gttcttttt ttgattccgg tttctttgaa      360 attttttga ttcggtaatc tccgagcaga aggaagaacg aaggaaggag cacagactta     420
gattggtata tatacgcata tgtggtgttg aagaaacatg aaattgccca gtattcttaa     480
cccaactgca cagaacaaaa acctgcagga aacgaagata atcatgtcg aaagctacat     540 ataaggaacg tgctgctact catcctagtc ctgttgctgc caagctattt aatatcatgc     600
acgaaaagca acaaacttg tgtgcttcat tggatgttcg taccaccaag gaattactgg     660
agttagttga agcattaggt cccaaaattt gtttactaaa aacacatgtg gatatcttga     720
ctgatttttc catggagggc acagttaagc cgctaaaggc attatccgcc aagtacaatt     780
ttttactctt cgaagacaga aaatttgctg acattggtaa tacagtcaaa ttgcagtact     840
ctgcgggtgt atacagaata gcagaatggg cagacattac gaatgcacac ggtgtggtgg     900
gcccaggtat tgttagcggt ttgaagcagg cggcagaaga agtaacaaag gaacctagag     960
gccttttgat gttagcagaa ttgtcatgca agggctccct atctactgga gaatatacta    1020
agggtactgt tgacattgcg aagagtgaca agatttttgt tatcggcttt attgctcaaa    1080
gagacatggg tggaagagat gaaggttacg attggttgat tatgacaccc ggtgtgggtt    1140
tagatgacaa gggagacgca ttgggtcaac agtatagaac cgtggatgat gtggtctcta    1200
caggatctga cattattatt gttggaagag gactatttgc aaagggaagg gatgctaagg    1260
tagagggtga acgttacaga aaagcaggct gggaagcata tttgagaaga tgcggccagc    1320
aaaactaaaa aactgtatta taagtaaatg catgtatact aaactcacaa attagagctt    1380
caatttaatt atatcagtta ttacccggga atctcggtcg taatgatttc tataatgacg    1440
aaaaaaaaaa aattggaaag aaaaagcttc atggcctta taaaaggaa ctatccaata    1500 cctcgccaga accaagtaac agtatttac ggggcacaaa tcaagaacaa taagacagga    1560
ctgtaaagat ggacgcatcg ctcgtccaac gccggcggac ct                       1602

<210> SEQ ID NO 36
<211> LENGTH: 95
<212> TYPE: DNA
<213> ORGANISM: Artificial Sequence
<220> FEATURE:
<223> OTHER INFORMATION: Primer KB520-266-136

<400> SEQUENCE: 36
aagatccgat cgaccgagaa ctgagaacgg tgcaatgatc aacatgatct gatgcacgag      60
```

```
cgcaacgctc acaagttcat catctcatgg atctg                                    95
```

<210> SEQ ID NO 37
<211> LENGTH: 93
<212> TYPE: DNA
<213> ORGANISM: Artificial Sequence
<220> FEATURE:
<223> OTHER INFORMATION: Primer KB521-266-136

<400> SEQUENCE: 37

```
agatcatgtt gatcattgca ccgttctcag ttctcggtcg atcggatctt gtgagcgttg         60
cgctcgtgca tcatgcgtcc atctttacag tcc                                      93
```

<210> SEQ ID NO 38
<211> LENGTH: 95
<212> TYPE: DNA
<213> ORGANISM: Artificial Sequence
<220> FEATURE:
<223> OTHER INFORMATION: Primer KB522-266-136

<400> SEQUENCE: 38

```
aagatccgat cgaccgagaa ctgagaacgg tgcaatgatc aacatgatct gcgtagctgc         60
ccagtatgag tcaggttcat catctcatgg atctg                                    95
```

<210> SEQ ID NO 39
<211> LENGTH: 95
<212> TYPE: DNA
<213> ORGANISM: Artificial Sequence
<220> FEATURE:
<223> OTHER INFORMATION: Primer KB523-266-136

<400> SEQUENCE: 39

```
agatcatgtt gatcattgca ccgttctcag ttctcggtcg atcggatctt ctgactcata         60
ctgggcagct acgcatgcgt ccatctttac agtcc                                    95
```

<210> SEQ ID NO 40
<211> LENGTH: 111
<212> TYPE: DNA
<213> ORGANISM: Artificial Sequence
<220> FEATURE:
<223> OTHER INFORMATION: Primer KB524-266-136

<400> SEQUENCE: 40

```
aagatccgat cgaccgagaa ctgagaacgg tgcaatgatc aacatgatct acgtgcacta         60
cgtagagggt cgcaccgcac cgatctacaa gttcatcatc tcatggatct g                  111
```

<210> SEQ ID NO 41
<211> LENGTH: 109
<212> TYPE: DNA
<213> ORGANISM: Artificial Sequence
<220> FEATURE:
<223> OTHER INFORMATION: Primer KB525-266-136

<400> SEQUENCE: 41

```
agatcatgtt gatcattgca ccgttctcag ttctcggtcg atcggatctt gtagatcggt         60
gcggtgcgac cctctacgta gtgcacgtat gcgtccatct ttacagtcc                     109
```

<210> SEQ ID NO 42
<211> LENGTH: 102
<212> TYPE: DNA
<213> ORGANISM: Artificial Sequence
<220> FEATURE:
<223> OTHER INFORMATION: Primer KB518-266-135

-continued

```
<400> SEQUENCE: 42
aagatccgat cgaccgagaa ctgagaacgg tgcaatgatc aacatgatct tatgtcgggt    60
gcggagaaag aggtaatgaa agttcatcat ctcatggatc tg                      102

<210> SEQ ID NO 43
<211> LENGTH: 101
<212> TYPE: DNA
<213> ORGANISM: Artificial Sequence
<220> FEATURE:
<223> OTHER INFORMATION: Primer KB519-266-135

<400> SEQUENCE: 43
agatcatgtt gatcattgca ccgttctcag ttctcggtcg atcggatctt tttcattacc    60
tctttctccg cacccgacat aatgcgtcca tctttacagt c                       101

<210> SEQ ID NO 44
<211> LENGTH: 23
<212> TYPE: DNA
<213> ORGANISM: Artificial Sequence
<220> FEATURE:
<223> OTHER INFORMATION: Primer KB496-266-100

<400> SEQUENCE: 44
ccaacaataa taatgtcaga tcc                                           23

<210> SEQ ID NO 45
<211> LENGTH: 19
<212> TYPE: DNA
<213> ORGANISM: Artificial Sequence
<220> FEATURE:
<223> OTHER INFORMATION: Primer KB495-266-100

<400> SEQUENCE: 45
ccgagcagaa ggaagaacg                                                19

<210> SEQ ID NO 46
<211> LENGTH: 1504
<212> TYPE: DNA
<213> ORGANISM: Artificial Sequence
<220> FEATURE:
<223> OTHER INFORMATION: RaBit12-0-M-262

<400> SEQUENCE: 46
gctcacacgc ggccaggggg agcctcgaca ctagtaatac acatcatcgt cctacaagtt    60
catcaaagtg ttggacagac aactatacca gcatggatct cttgtatcgg ttcttttctc   120
ccgctctctc gcaataacaa tgaacactgg gtcaatcata gcctacacag gtgaacagag   180
tagcgtttat acagggttta tacggtgatt cctacggcaa aaattttca tttctaaaaa    240 aaaaagaaa aattttctt tccaacgcta gaaggaaaag aaaaatctaa ttaaattgat    300
ttggtgattt tctgagagtt ccctttttca tatatcgaat tttgaatata aaaggagatc   360 gaaaaattt ttctattcaa tctgtttct ggttttattt gatagttttt ttgtgtatta   420
ttattatgga ttagtactgg tttatatggg tttttctgta taacttcttt ttatttagt   480 ttgtttaatc ttattttgag ttacattata gttccctaac tgcaagagaa gtaacattaa   540
aaatgaccac tcttgacgac acggcttacc ggtaccgcac cagtgtcccg ggggacgccg   600
aggccatcga ggcactggat gggtccttca ccaccgacac cgtcttccgc gtcaccgcca   660
ccggggacgg cttcacccctg cgggaggtgc cggtggaccc gccctgacc aaggtgttcc   720 ccgacgacga atcggacgac gaatcggacg ccggggagga cggcgacccg gactcccgga   780
```

```
cgttcgtcgc gtacggggac gacggcgacc tggcgggctt cgtggtcgtc tcgtactccg      840
gctggaaccg ccggctgacc gtcgaggaca tcgaggtcgc cccggagcac cgggggcacg      900
gggtcgggcg cgcgttgatg gggctcgcga cggagttcgc ccgcgagcgg ggcgccgggc      960
acctctggct ggaggtcacc aacgtcaacg caccggcgat ccacgcgtac cggcggatgg     1020
ggttcaccct ctgcggcctg dacaccgccc tgtacgacgg caccgcctcg dacggcgagc     1080
aggcgctcta catgagcatg ccctgcccct gagtttaact tgatactact agatttttc      1140 tcttcattta taaaattttt ggttataatt gaagctttag aagtatgaaa aaatccttttt    1200 ttttcattct ttgcaaccaa aataagaagc ttcttttatt cattgaaatg atgaatataa     1260
acctaacaaa agaaaaagac tcgaatatca aacattaaaa aaaaataaaa gaggttatct     1320
gttttcccat ttagttggag tttgcatttt ctaatagata gaactctcaa ttaatgtgga     1380
tttagtttct ctgttcgttt ttttttgttt tgttctcact gtatttacat ttctatttag     1440
tatttagtta ttcatataat cttaacttct cgaggagctc cgctcgtcca acgccggcgg     1500
acct                                                                  1504
```

```
<210> SEQ ID NO 47
<211> LENGTH: 97
<212> TYPE: DNA
<213> ORGANISM: Artificial Sequence
<220> FEATURE:
<223> OTHER INFORMATION: Primer MF51-312-97

<400> SEQUENCE: 47
cgttacgaag cacacactag ttagcgtcga gacacatagc gacgctagaa gatgcacgag      60
cgcaacgctc acaatcgaca ctagtaatac acatcat                              97

<210> SEQ ID NO 48
<211> LENGTH: 94
<212> TYPE: DNA
<213> ORGANISM: Artificial Sequence
<220> FEATURE:
<223> OTHER INFORMATION: Primer MF52-312-97

<400> SEQUENCE: 48
ttctagcgtc gctatgtgtc tcgacgctaa ctagtgtgtg cttcgtaacg ttgtgagcgt      60
tgcgctcgtg catcgagctc ctcgagaagt taag                                 94

<210> SEQ ID NO 49
<211> LENGTH: 97
<212> TYPE: DNA
<213> ORGANISM: Artificial Sequence
<220> FEATURE:
<223> OTHER INFORMATION: Primer MF57-312-98

<400> SEQUENCE: 49
ttaatcagcg cccagagact agcactgaat gatcaacggg tagttcacac gatgcacgag      60
cgcaacgctc acaatcgaca ctagtaatac acatcat                              97

<210> SEQ ID NO 50
<211> LENGTH: 94
<212> TYPE: DNA
<213> ORGANISM: Artificial Sequence
<220> FEATURE:
<223> OTHER INFORMATION: Primer MF58-312-98

<400> SEQUENCE: 50
gtgtgaacta cccgttgatc attcagtgct agtctctggg cgctgattaa ttgtgagcgt      60
```

```
tgcgctcgtg catcgagctc ctcgagaagt taag                              94
```

```
<210> SEQ ID NO 51
<211> LENGTH: 17
<212> TYPE: DNA
<213> ORGANISM: Artificial Sequence
<220> FEATURE:
<223> OTHER INFORMATION: Primer KB479-266-81

<400> SEQUENCE: 51
cgtccgattc gtcgtcg                                                 17
```

```
<210> SEQ ID NO 52
<211> LENGTH: 16
<212> TYPE: DNA
<213> ORGANISM: Artificial Sequence
<220> FEATURE:
<223> OTHER INFORMATION: Primer KB480-266-81

<400> SEQUENCE: 52
gaggtgccgg tggacc                                                  16
```

```
<210> SEQ ID NO 53
<211> LENGTH: 1960
<212> TYPE: DNA
<213> ORGANISM: Artificial Sequence
<220> FEATURE:
<223> OTHER INFORMATION: RaBit12-0-M-21

<400> SEQUENCE: 53
gctcacacgc ggccaggggg agcctcgaca ctagtaatac acatcatcgt cctacaagtt    60
catcaaagtg ttggacagac aactatacca gcatggatct cttgtatcgg ttcttttctc   120
ccgctctctc gcaataacaa tgaacactgg gtcaatcata gcctacacag gtgaacagag   180
tagcgtttat acagggttta tacggtgatt cctacggcaa aaattttttca tttctaaaaa   240
aaaaaagaaa aattttttctt tccaacgcta gaaggaaaag aaaaatctaa ttaaattgat   300
ttggtgattt tctgagagtt ccctttttca tatatcgaat tttgaatata aaaggagatc   360
gaaaaaattt ttctattcaa tctgtttttct ggttttattt gatagttttt ttgtgtatta   420
ttattatgga ttagtactgg tttatatggg ttttttctgta taacttcttt ttattttagt   480
ttgtttaatc ttattttgag ttacattata gttccctaac tgcaagagaa gtaacattaa   540
aaatgaaaaa gcctgaactc accgcgacgt ctgtcgagaa gtttctgatc gaaaagttcg   600
acagcgtctc cgacctgatg cagctctcgg agggcgaaga atctcgtgct ttcagcttcg   660
atgtaggagg gcgtggatat gtcctgcggg taaatagctg cgccgatggt ttctacaaag   720
atcgttatgt ttatcggcac tttgcatcgg ccgcgctccc gattccggaa gtgcttgaca   780
ttggggaatt cagcgagagc ctgacctatt gcatctcccg ccgtgcacag ggtgtcacgt   840
tgcaagacct gcctgaaacc gaactgcccg ctgttctgca gccggtcgcg gaggccatgg   900
atgcgatcgc tgcggccgat cttagccaga cgagcgggtt cggcccattc ggaccgcaag   960
gaatcggtca atacactaca tggcgtgatt tcatatgcgc gattgctgat ccccatgtgt  1020
atcactggca aactgtgatg gacgacaccg tcagtgcgtc cgtcgcgcag gctctcgatg  1080
agctgatgct ttgggccgag gactgccccg aagtccggca cctcgtgcac gcggatttcg  1140
gctccaacaa tgtcctgacg gacaatggcc gcataacagc ggtcattgac tggagcgagg  1200
cgatgttcgg ggattcccaa tacgaggtcg ccaacatctt cttctggagg ccgtggttgg  1260
cttgtatgga gcagcagacg cgctacttcg agcggaggca tccggagctt gcaggatcgc  1320
```

```
cgcggctccg ggcgtatatg ctccgcattg gtcttgacca actctatcag agcttggttg    1380
acggcaattt cgatgatgca gcttgggcgc agggtcgatg cgacgcaatc gtccgatccg    1440
gagccgggac tgtcgggcgt acacaaatcg cccgcagaag cgcggccgtc tggaccgatg    1500
gctgtgtaga agtactcgcc gatagtggaa accgacgccc cagcactcgt ccagggcaa     1560 aggaataggt ttaacttgat actactagat ttttctctt catttataaa attttttggtt    1620 ataattgaag ctttagaagt atgaaaaaat ccttttttt cattctttgc aaccaaaata    1680
agaagcttct tttattcatt gaatgatga atataaacct aacaaagaa aaagactcga     1740 atatcaaaca ttaaaaaaaa ataaagagg ttatctgttt tcccatttag ttggagtttg    1800
cattttctaa tagatagaac tctcaattaa tgtggattta gtttctctgt tcgttttttt    1860
ttgttttgtt ctcactgtat ttacatttct atttagtatt tagttattca tataatctta   1920
acttctcgag gagctccgct cgtccaacgc cggcggacct                          1960
```

```
<210> SEQ ID NO 54
<211> LENGTH: 97
<212> TYPE: DNA
<213> ORGANISM: Artificial Sequence
<220> FEATURE:
<223> OTHER INFORMATION: Primer MF53-312-98

<400> SEQUENCE: 54
gtactgccta gtagaaacgg atctccacgt actagagtcc acctggtatc gatgcacgag    60
cgcaacgctc acaatcgaca ctagtaatac acatcat                             97

<210> SEQ ID NO 55
<211> LENGTH: 94
<212> TYPE: DNA
<213> ORGANISM: Artificial Sequence
<220> FEATURE:
<223> OTHER INFORMATION: Primer MF54-312-98

<400> SEQUENCE: 55
gataccaggt ggactctagt acgtggagat ccgtttctac taggcagtac ttgtgagcgt    60
tgcgctcgtg catcgagctc ctcgagaagt taag                                94

<210> SEQ ID NO 56
<211> LENGTH: 16
<212> TYPE: DNA
<213> ORGANISM: Artificial Sequence
<220> FEATURE:
<223> OTHER INFORMATION: Primer KB492-266-100

<400> SEQUENCE: 56
gccgaaatcc gcgtgc                                                    16

<210> SEQ ID NO 57
<211> LENGTH: 19
<212> TYPE: DNA
<213> ORGANISM: Artificial Sequence
<220> FEATURE:
<223> OTHER INFORMATION: Primer KB491-266-100

<400> SEQUENCE: 57
cggaagtgct tgacattgg                                                 19

<210> SEQ ID NO 58
<211> LENGTH: 1744
<212> TYPE: DNA
<213> ORGANISM: Artificial Sequence
<220> FEATURE:
```

<223> OTHER INFORMATION: RaBit 12-0-M-261

<400> SEQUENCE: 58

| | | |
|---|---|---|
| gctcacacgc ggccaggggg agcctcgaca ctagtaatac acatcatcgt cctacaagtt | 60 |
| catcaaagtg ttggacagac aactatacca gcatggatct cttgtatcgg ttcttttctc | 120 |
| ccgctctctc gcaataacaa tgaacactgg gtcaatcata gcctacacag gtgaacagag | 180 |
| tagcgtttat acagggttta tacggtgatt cctacggcaa aaattttca tttctaaaaa | 240 |
| aaaaaagaaa aattttctt tccaacgcta gaaggaaaag aaaaatctaa ttaaattgat | 300 |
| ttggtgattt tctgagagtt cccttttca tatatcgaat tttgaatata aaaggagatc | 360 |
| gaaaaattt ttctattcaa tctgttttct ggttttattt gatagttttt ttgtgtatta | 420 |
| ttattatgga ttagtactgg tttatatggg ttttctgta taacttcttt ttatttagt | 480 |
| ttgtttaatc ttattttgag ttacattata gttccctaac tgcaagagaa gtaacattaa | 540 |
| aaatgggtaa ggaaaagact cacgtttcga ggccgcgatt aaattccaac atggatgctg | 600 |
| atttatatgg gtataaatgg gctcgcgata atgtcgggca atcaggtgcg acaatctatc | 660 |
| gattgtatgg gaagcccgat gcgccagagt tgtttctgaa acatggcaaa ggtagcgttg | 720 |
| ccaatgatgt tacagatgag atggtcagac taaactggct gacggaattt atgcctcttc | 780 |
| cgaccatcaa gcattttatc cgtactcctg atgatgcatg gttactcacc actgcgatcc | 840 |
| ccggcaaaac agcattccag gtattagaag aatatcctga ttcaggtgaa aatattgttg | 900 |
| atgcgctggc agtgttcctg cgccggttgc attcgattcc tgtttgtaat tgtccttta | 960 |
| acagcgatcg cgtatttcgt ctcgctcagg cgcaatcacg aatgaataac ggtttggttg | 1020 |
| atgcgagtga ttttgatgac gagcgtaatg gctggcctgt tgaacaagtc tggaaagaaa | 1080 |
| tgcataagct tttgccattc tcaccggatt cagtcgtcac tcatggtgat ttctcacttg | 1140 |
| ataaccttat ttttgacgag gggaaattaa taggttgtat tgatgttgga cgagtcggaa | 1200 |
| tcgcagaccg ataccaggat cttgccatcc tatggaactg cctcggtgag ttttctcctt | 1260 |
| cattacagaa acggcttttt caaaaatatg gtattgataa tcctgatatg aataaattgc | 1320 |
| agtttcattt gatgctcgat gagttttct aagtttaact tgatactact agattttttc | 1380 |
| tcttcattta taaaattttt ggttataatt gaagctttag aagtatgaaa aaatcctttt | 1440 |
| ttttcattct ttgcaaccaa ataagaagc ttcttttatt cattgaaatg atgaatataa | 1500 |
| acctaacaaa agaaaagac tcgaatatca acattaaaa aaaataaaa gaggttatct | 1560 |
| gttttcccat ttagttggag tttgcatttt ctaatagata gaactctcaa ttaatgtgga | 1620 |
| tttagtttct ctgttcgttt ttttttgttt tgttctcact gtatttacat ttctatttag | 1680 |
| tatttagtta ttcatataat cttaacttct cgaggagctc cgctcgtcca acgccggcgg | 1740 |
| acct | 1744 |

<210> SEQ ID NO 59
<211> LENGTH: 102
<212> TYPE: DNA
<213> ORGANISM: Artificial Sequence
<220> FEATURE:
<223> OTHER INFORMATION: Primer TD_180

<400> SEQUENCE: 59

| | | |
|---|---|---|
| cgaggattaa cgtgtaaggc cctaagctat gtaccgcatc tcctaagaga gatgcacgag | 60 |
| cgcaacgctc acaatcgaca ctagtaatac acatcatcgt cc | 102 |

<210> SEQ ID NO 60

```
<211> LENGTH: 102
<212> TYPE: DNA
<213> ORGANISM: Artificial Sequence
<220> FEATURE:
<223> OTHER INFORMATION: Primer TD_181

<400> SEQUENCE: 60
tctcttagga gatgcggtac atagcttagg gccttacacg ttaatcctcg ttgtgagcgt    60
tgcgctcgtg catcgagctc ctcgagaagt taagattata tg                     102

<210> SEQ ID NO 61
<211> LENGTH: 24
<212> TYPE: DNA
<213> ORGANISM: Artificial Sequence
<220> FEATURE:
<223> OTHER INFORMATION: Primer KB494-266-100

<400> SEQUENCE: 61
tatctattag aaaatgcaaa ctcc                                          24

<210> SEQ ID NO 62
<211> LENGTH: 20
<212> TYPE: DNA
<213> ORGANISM: Artificial Sequence
<220> FEATURE:
<223> OTHER INFORMATION: Primer KB493-266-100

<400> SEQUENCE: 62
gttactcacc actgcgatcc                                               20

<210> SEQ ID NO 63
<211> LENGTH: 429
<212> TYPE: DNA
<213> ORGANISM: Artificial Sequence
<220> FEATURE:
<223> OTHER INFORMATION: coding sequence for F-CphI

<400> SEQUENCE: 63
atgactaagt tgtattctga cttgtacagg acctgcatga catgcggaga agaaaaattg    60
tcaaccgagt tctacgtcag gaacaagaag accggagtta gacattcatc atgcaaagag   120
tgtgacaagg tcagggtcaa atcaagacac aaggagaacc ctgaaaggac caaaacaac    180 gacttgaaga gattgtacgg aatcaccttg gacgagcata cccaaatgta tgaggaacaa   240
aatggtgtat gtgcaatttg caagggagaa ggagatggaa agtggaagaa attgtgtgtt   300
gaccatgatc acgaaacagg aaaggtcagg cagttgttgt gtaggaactg caatatgatg   360
ttgggtcagg tcaacgacaa cgttaactta ttatcagaaa tgataaagta tttgaaagaa   420
tatcagtaa                                                          429

<210> SEQ ID NO 64
<211> LENGTH: 103
<212> TYPE: DNA
<213> ORGANISM: Artificial Sequence
<220> FEATURE:
<223> OTHER INFORMATION: Primer TD_176

<400> SEQUENCE: 64
gtcaaagcgc gattcgctag gaatgagagc gagaacgaac cggagtatat gatgcacgag    60
cgcaacgctc acaaaataca catcatcgtc ctacaagttc atc                    103

<210> SEQ ID NO 65
<211> LENGTH: 103
<212> TYPE: DNA
```

-continued

<213> ORGANISM: Artificial Sequence
<220> FEATURE:
<223> OTHER INFORMATION: Primer TD_177

<400> SEQUENCE: 65
atatactccg gttcgttctc gctctcattc ctagcgaatc gcgctttgac ttgtgagcgt    60
tgcgctcgtg catcaagtta agattatatg aataactaaa tac                    103

<210> SEQ ID NO 66
<211> LENGTH: 24
<212> TYPE: DNA
<213> ORGANISM: Artificial Sequence
<220> FEATURE:
<223> OTHER INFORMATION: Primer TD_183

<400> SEQUENCE: 66
tcggccacga agtgcacgca gttg                                          24

<210> SEQ ID NO 67
<211> LENGTH: 24
<212> TYPE: DNA
<213> ORGANISM: Artificial Sequence
<220> FEATURE:
<223> OTHER INFORMATION: Primer TD_182

<400> SEQUENCE: 67
tcgagttctg gaccgaccgg ctcg                                          24

<210> SEQ ID NO 68
<211> LENGTH: 28
<212> TYPE: DNA
<213> ORGANISM: Artificial Sequence
<220> FEATURE:
<223> OTHER INFORMATION: Primer RYSE0

<400> SEQUENCE: 68
gacggcacgg ccacgcgttt aaaccgcc                                      28

<210> SEQ ID NO 69
<211> LENGTH: 28
<212> TYPE: DNA
<213> ORGANISM: Artificial Sequence
<220> FEATURE:
<223> OTHER INFORMATION: Primer RYSE19

<400> SEQUENCE: 69
cggtgtttaa accccagcgc ctggcggg                                      28

<210> SEQ ID NO 70
<211> LENGTH: 598
<212> TYPE: DNA
<213> ORGANISM: Artificial Sequence
<220> FEATURE:
<223> OTHER INFORMATION: RaBit01-0-U-407

<400> SEQUENCE: 70
gacggcacgg ccacgcgttt aaaccgccga gctattcgcg gaacattcta gctcgtttgc    60
atcttcttgc atttggtagg ttttcaatag ttcggtaata ttaacggata cctactatta   120
tcccctagta ggctcttttc acggagaaat tcgggagtgt ttttttttccg tgcgcatttt   180 cttagctata ttcttccagc ttcgcctgct gcccggtcat cgttcctgtc acgtagtttt   240
tccggattcg tccggctcat ataataccgc aataaacacg gaatatctcg ttccgcggat   300
tcggttaaac tctcggtcgc ggattatcac agagaaagct tcgtggagaa ttttttccaga   360

```
ttttccgctt tccccgatgt tggtatttcc ggaggtcatt atactgaccg ccattataat      420
gactgtacaa cgaccttctg gagaaagaaa caactcaata acgatgtggg acattggggg      480
cccactcaaa aaatctgggg actatatccc cagagaattt ctccagaaga gaagaaaagt      540
caaagttttt tttcgcttgg gggttgcata taaagctcac acgcggccag ggggagcc       598

<210> SEQ ID NO 71
<211> LENGTH: 574
<212> TYPE: DNA
<213> ORGANISM: Artificial Sequence
<220> FEATURE:
<223> OTHER INFORMATION: RaBit29-0-D-408

<400> SEQUENCE: 71
cgctcgtcca acgccggcgg acctaataaa agacattggt acatgatatc aaacagaatt       60
ttaacatttc ttgatccagt ttgtaaacaa acaaacaat ttttctacca tttaacttca       120
taccatcggc gagagccgaa caggaaaaaa agaagtctc cggttatcgt aagcagtatc       180
aaataataag aatgtatgtg tgtgcaattt gttatacca cgaagaagtg cgcagtagag       240
ttagaaaacc aactgagtaa tctttactcc cgacaatcgt ccaataatcc tcttgttgct       300
aggaacgtga tgatggattt cgtttgaaat ccggacggaa aactcaaaag aagtccaacc      360
accaaccatt ttcgagcctc aagaatctct aagcaggttt ctttactaag gggatggcct      420
ttctgtcctg gacatttttt ccttcctttt ttcatttcct tgaaaggaac agattttttt      480 tgactttgc cacacagctg cactatctca acccctttta catttaagt tttcgggttg       540 aatggccggt gtttaaaccc cagcgcctgg cggg                                574

<210> SEQ ID NO 72
<211> LENGTH: 668
<212> TYPE: DNA
<213> ORGANISM: Artificial Sequence
<220> FEATURE:
<223> OTHER INFORMATION: RaBit23-0-P-39

<400> SEQUENCE: 72
cgctcgtcca acgccggcgg accttacttt ttttttggat ggacgcaaag aagttaata       60 atcatattac atggcattac caccatatac atatccatat ctaatcttac ttatatgttg      120
tggaaatgta aagagcccca ttatcttagc ctaaaaaaac cttctctttg gaactttcag      180
taatacgctt aactgctcat tgctatattg aagtacggat tagaagccgc cgagcgggcg      240
acagccctcc gacggaagac tctcctccgt gcgtcctcgt cttcaccggt cgcgttcctg      300
aaacgcagat gtgcctcgcg ccgcactgct ccgaacaata aagattctac aatactagct      360
tttatggtta tgaagaggaa aaattggcag taacctggcc ccacaaacct tcaaattaac      420
gaatcaaatt aacaaccata ggatgataat gcgattagtt ttttagcctt atttctgggg      480
taattaatca gcgaagcgat gattttttgat ctattaacag atatataaat ggaaaagctg     540
cataaccact ttaactaata ctttcaacat tttcagtttg tattacttct tattcaaatg     600
tcataaaagt atcaacaaaa aattgttaat atacctctat acttatcccc gcgtgcttgg      660
ccggccgt                                                             668

<210> SEQ ID NO 73
<211> LENGTH: 311
<212> TYPE: DNA
<213> ORGANISM: Artificial Sequence
<220> FEATURE:
<223> OTHER INFORMATION: RaBit45-0-T-64
```

-continued

```
<400> SEQUENCE: 73
aacctgcagg ccgcgagcgc cgattaagtg aatttacttt aaatcttgca tttaaataaa      60
ttttcttttt atagctttat gacttagttt caatttatat actattttaa tgacattttc     120
gattcattga ttgaaagctt tgtgtttttt cttgatgcgc tattgcattg ttcttgtctt     180
tttcgccaca tgtaatatct gtagtagata cctgatacat tgtggatgct gagtgaaatt     240
ttagttaata atggaggcgc tcttaataat tttggggata ttggcttaac gcgatcgccg     300
acgccgccga t                                                          311

<210> SEQ ID NO 74
<211> LENGTH: 24
<212> TYPE: DNA
<213> ORGANISM: Artificial Sequence
<220> FEATURE:
<223> OTHER INFORMATION: Primer RYSE4

<400> SEQUENCE: 74
cgctcgtcca acgccggcgg acct                                             24

<210> SEQ ID NO 75
<211> LENGTH: 24
<212> TYPE: DNA
<213> ORGANISM: Artificial Sequence
<220> FEATURE:
<223> OTHER INFORMATION: Primer RYSE11

<400> SEQUENCE: 75
atcggcggcg tcggcgatcg cgtt                                             24

<210> SEQ ID NO 76
<211> LENGTH: 547
<212> TYPE: DNA
<213> ORGANISM: Artificial Sequence
<220> FEATURE:
<223> OTHER INFORMATION: RaBit01-0-U-97

<400> SEQUENCE: 76
gacggcacgg ccacgcgttt aaaccgccct ccaagctgac ataaatcgca ctttgtatct      60 acttttttt attcgaaaac aaggcacaac aatgaatcta tcgccctgtg agattttcaa     120
tctcaagttt gtgtaataga tagcgttata ttatagaact ataaaggtcc ttgaatatac     180
atagtgtttc attcctatta ctgtatatgt gactttacat tgttacttcc gcggctattt     240
gacgttttct gcttcaggtg cggcttggag ggcaaagtgt cagaaaatcg ccaggccgt      300 atgacacaaa agagtagaaa acgagatctc aaatatctcg aggcctgtcc tctatacaac     360
cgcccagctc tctgacaaag ctccagaacg gttgtctttt gtttcgaaaa gccaaggtcc     420
cttataattg ccctccattt tgtgtcacct atttaagcaa aaattgaaa gtttactaac      480 ctttcattaa agagaaataa caatattata aaaagcgctt aaagctcaca cgcggccagg     540
gggagcc                                                               547

<210> SEQ ID NO 77
<211> LENGTH: 568
<212> TYPE: DNA
<213> ORGANISM: Artificial Sequence
<220> FEATURE:
<223> OTHER INFORMATION: RaBit29-0-D-23

<400> SEQUENCE: 77
cgctcgtcca acgccggcgg acctataaac taatgatttt aaatcgttaa aaaaatatgc      60
```

```
gaattctgtg gatcgaacac aggacctcca gataacttga ccgaagtttt ttcttcagtc      120
tggcgctctc ccaactgagc taaatccgct tactatttgt tatcagttcc cttcatatct      180
acatagaata ggttaagtat tttattagtt gccagaagaa ctactgatag ttgggaatat      240
ttggtgaata atgaagattg ggtgaataat ttgataattt tgagattcaa ttgttaatca      300
atgttacaat attatgtata cagagtatac tagaagttct cttcggagat cttgaagttc      360
acaaagggga tcgatatttt ctacataata ttatcattac ttcttcccca tcttatattt      420
gtcattcatt attgattatg atcaatgcaa taatgattgg tagttgccaa acatttaata      480
cgatcctctg taatatttct atgaataatt atcacagcaa cgttcaatta tcttcaattc      540
cggtgtttaa accccagcgc ctggcggg                                        568

<210> SEQ ID NO 78
<211> LENGTH: 552
<212> TYPE: DNA
<213> ORGANISM: Artificial Sequence
<220> FEATURE:
<223> OTHER INFORMATION: RaBit01-0-U-270

<400> SEQUENCE: 78
gacggcacgg ccacgcgttt aaaccgccca gatggaatcc cttccataga gagaaggagc       60
aagcaactga cccaatattg actgccactg gacctgaaga catgcaacaa agtgcaagca      120
tagtggggcc ttcttccaat gctaatccgg tcactgccac tgctgctacg gaaaaccaac      180
ctaaaggtat taacttcttc actataagaa aatcacacga gcgcccggac gatgtctctg      240
tttaaatggc gcaagttttc cgctttgtaa tatatattta taccccttc ttctctcccc       300 tgcaatataa tagtttaatt ctaatattaa taatatccta tattttcttc atttaccggc      360
gcactctcgc ccgaacgacc tcaaaatgtc tgctacattc ataataacca aaagctcata      420 acttttttt ttgaacctga atatatatac atcacatatc actgctggtc cttgccgacc      480
agcgtataca atctcgatag ttggtttccc gttctttcca ctcccgtcgc tcacacgcgg      540 ccaggggag cc                                                          552

<210> SEQ ID NO 79
<211> LENGTH: 561
<212> TYPE: DNA
<213> ORGANISM: Artificial Sequence
<220> FEATURE:
<223> OTHER INFORMATION: RaBit29-0-D-95

<400> SEQUENCE: 79
cgctcgtcca acgccggcgg acctcgtgca tgcgggtgtt cttatttatt agcatactac       60
atttgaaata tcaaatttcc ttagtagaaa agtgagagaa ggtgcactga cacaaaaaat      120
aaaatgctac gtataactgt caaaactttg cagcagcggg catccttcca tcatagcttc      180
aaacatatta gcgttcctga tcttcatacc cgtgctcaaa atgatcaaac aaactgttat      240
tgccaagaaa taaacgcaag gctgccttca aaaactgatc cattagatcc tcatatcaag      300
cttcctcata gaacgcccaa ttacaataag catgttttgc tgttatcacc gggtgatagg      360
tttgctcaac catggaaggt agcatggaat cataatttgg atactaatac aaatcggcca      420
tataatgcca ttagtaaatt gcgctcccat ttaggtggtt ctccaggaat actaataaat      480
gcggtgcatt tgcaaaatga atttattcca aggccaaaac aacacgatga atgcggtgtt      540
taaaccccag cgcctggcgg g                                               561

<210> SEQ ID NO 80
```

```
<211> LENGTH: 1179
<212> TYPE: DNA
<213> ORGANISM: Artificial Sequence
<220> FEATURE:
<223> OTHER INFORMATION: Coding sequence for PI-MgaI(pps1) with
      N-terminal SV40 NLS

<400> SEQUENCE: 80
atgttaattt ctccaaagaa gaagaggaag gtcgagttgg gatgtttagc aggtgatacc      60
ttggtttgga ccgccaatag aggacaggtc ccaatcaagg agatagagtt cggtgacagg     120
gtcttctctt acgacgaatc agcagagaga ttcgtagttg ccccagtaaa agcatctgct     180
caaacagaca ccaggttaac ctacgaggta aagactacca aaggtcagt tagggctact      240
gacaaccacc caatgttggt cttgagggat gaaaggaagg agggtagaca aagagccagg     300
tatgctagga gatgggtaac agtaggacag ataaagcctg gtgactttat cgctgttcca     360
agagctgtac caaacttcgg agtcgctgag cagttgcctt cagtcgccgg tttgaccaca     420
ccagccacct catcagcaga tttgatgtgg ttattgggat gtacgtcgg agacggaaac      480
ttgcacttgt caaccaagac ctatagggta caatttgcta tacctgcaac cgatagagag     540
ttaagggccg agttgactag agttatcaag gacttgttcg gattgaggtg cattgaggca     600
gatgagtaca gggttgtcgt caattcaaag gcattaaccg aatggatcgc agctttgggt     660
tttggaggtt tgtcattgac aaaaagagtc ccagactggg tttatggatt gccagtcgat     720
caaagattgg cattcttagg tggatgggta gatgccgatg ttatgtctc tccagacaaa      780
tcaggttcaa ttttattgac atgtgccaat caggccttga taggtcaggc cagggaatta     840
gctgagttag ctggtttgag ggctggaggt ccttggtcat tcactcaacc ttacagacat     900
gcaccagaca ggatgcaaat tgcatggagg ttgggtatct ctggtgattt cgagagattg     960
ggttgtagga acccaaagag aaccgacagg ttcggtagga aaggtacat gcattcatct     1020
tcaggtgccc acggaaccac cattagggcc cactgcaacg attggttggg atttgagagg    1080
gtcaaagcag tcgagccata tgcagttgag cctgtatacg acatcgaggt tgacggtcca    1140
cacaacttcg tcgcagaggg attagtagtt cataactaa                           1179

<210> SEQ ID NO 81
<211> LENGTH: 1122
<212> TYPE: DNA
<213> ORGANISM: Artificial Sequence
<220> FEATURE:
<223> OTHER INFORMATION: Coding sequence for PI-MtuII(pps1) with
      N-terminal SV40 NLS

<400> SEQUENCE: 81
atgttgatct caccaaagaa gaagagaaaa gtcgagttgg gttgcttacc tgctggagag      60
ttaataacta cagccgacgg tgacttgagg cctatcgagt ctataagggt aggagacttc     120
gttacaggtc acgatggtag gccacacaga gtcacagcag ttcaggtcag agatttagat     180
ggagaattgt tcactttcac ccctatgtct cctgctaacg cattttctgt taccgccgaa     240
catcctttat tagcaatccc tagggacgaa gtcaggggtta tgaggaagga gaggaatggt     300
tggaaggctg aagtcaactc taccaaatta agatctgcag agccaaggtg gatcgcagct     360
aaagatgttg ccgagggtga ttttcttgatc taccctaaac caaagcctat ccctcacagg     420
accgtattgc cattggagtt cgctaggttg gctggatact acttagcaga aggtcatgct     480
tgtttaacca acgatgcgca gtctttaatc ttctcattcc actctgatga atttgaatac     540
gtagaggacg ttaggcaagc ctgtaaatca ttatacgaaa agtctggatc agtccttgatc    600
```

```
gaggagcata acactcagc aagggtaacc gtctacacta agctggata tgctgccatg      660 agggacaacg tcggtatagg ttcttcaaat aaaaagttat cagacttgtt aatgaggcag     720
gacgaaacct ttttgaggga gttggttgac gcatatgtta acggagatgg aaacgtaacc    780
agaaggaatg gagcagtttg gaaaagggtc cacacaacat caaggttgtg ggcatttcaa    840
ttacagtcaa ttttggcaag attgggtcat tacgcaaccg tagaattaag gagaccaggt    900
ggtccaggtg taataatggg taggaacgtt gttaggaaag acatctacca ggtacagtgg    960
accgagggag gtaggggtcc aaagcaggca agggactgcg gagattactt cgcagttcca   1020
atcaagaaga gagctgttag ggaagcccac gagccagtct acaacttgga cgtcgaaaac   1080
ccagactcat acttggccta tggttttgca gtccataact aa                      1122
```

<210> SEQ ID NO 82
<211> LENGTH: 708
<212> TYPE: DNA
<213> ORGANISM: Artificial Sequence
<220> FEATURE:
<223> OTHER INFORMATION: Coding sequence for I-SceI

<400> SEQUENCE: 82

```
atgaagaaca tcaagaagaa ccaggtcatg aatctgggtc ctaactctaa attattgaaa      60
gaatataaga gccaacttat cgaactaaac attgaacaat ttgaggctgg aataggttta    120
attttaggtg atgcgtacat taggtccaga gatgagggta aaacatactg tatgcagttt    180
gagtggaaaa ataaagccta tatggatcat gttttgtttgc tgtatgatca atgggtatta   240
tctcctcctc ataagaaaga aagagttaat cacctaggga atttagtgat aacgtgggga    300
gcacagactt ttaagcacca agcgttcaac aaaattagca aatttgtttat tgtcaataat   360 aagaaaacaa ttcctaataa tttggtggaa aactacctaa ctccaatgtc tttagcatat    420
tggttcatgg atgacggtgg aaaatgggat tacaacaaaa acagcacaaa caaatctata    480
gtgctaaata cgcaaagttt tacttttgaa gaagtagaat acttagttaa aggattgcgt    540
aacaagtttc aacttaattg ttatgttaag attaataaaa ataaaccgat catttacata    600
gattctatgt catatttaat attctacaat cttattaaac cttatttaat tccgcaaatg    660
atgtataaac tgccaaatac catatcttcc gagacgttcc tcaagtag                 708
```

<210> SEQ ID NO 83
<211> LENGTH: 36
<212> TYPE: DNA
<213> ORGANISM: Artificial Sequence
<220> FEATURE:
<223> OTHER INFORMATION: Primer KB510-266-134

<400> SEQUENCE: 83

```
ctgagctcta aatataaaca ttaaatacat tacacg                              36
```

<210> SEQ ID NO 84
<211> LENGTH: 32
<212> TYPE: DNA
<213> ORGANISM: Artificial Sequence
<220> FEATURE:
<223> OTHER INFORMATION: Primer KB511-266-134

<400> SEQUENCE: 84

```
gactcgaggc tcaaaagaag actaactaag ag                                  32
```

<210> SEQ ID NO 85
<211> LENGTH: 55
<212> TYPE: DNA

```
<213> ORGANISM: Artificial Sequence
<220> FEATURE:
<223> OTHER INFORMATION: Primer KB512-266-134

<400> SEQUENCE: 85
aattcgacct ttctcttctt ttttggagag attgtcatat tttattattg tattg        55

<210> SEQ ID NO 86
<211> LENGTH: 48
<212> TYPE: DNA
<213> ORGANISM: Artificial Sequence
<220> FEATURE:
<223> OTHER INFORMATION: Primer KB513-266-134

<400> SEQUENCE: 86
caaaaaagaa gagaaaggtc gaattaggtt ttgccaaggg taccaatg               48

<210> SEQ ID NO 87
<211> LENGTH: 44
<212> TYPE: DNA
<213> ORGANISM: Artificial Sequence
<220> FEATURE:
<223> OTHER INFORMATION: Primer KB514-266-134

<400> SEQUENCE: 87
ggttgtcgtc cataattgct gaaagatttt tgtagttttt gtat                    44

<210> SEQ ID NO 88
<211> LENGTH: 44
<212> TYPE: DNA
<213> ORGANISM: Artificial Sequence
<220> FEATURE:
<223> OTHER INFORMATION: Primer KB515-266-134

<400> SEQUENCE: 88
atacaaaaac tacaaaaatc tttcagcaat tatggacgac aacc                    44

<210> SEQ ID NO 89
<211> LENGTH: 1700
<212> TYPE: DNA
<213> ORGANISM: Artificial Sequence
<220> FEATURE:
<223> OTHER INFORMATION: xMarker xM0.URA.F-CphI

<400> SEQUENCE: 89
aagatccgat cgaccgagaa ctgagaacgg tgcaatgatc aacatgatct gatgcacgag    60
cgcaacgctc acaagttcat catctcatgg atctgcacat gaacaaacac cagagtcaaa   120
cgacgttgaa attgaggcta ctgcgccaat tgatgacaat acagacgatg ataacaaacc   180
gaagttatct gatgtagaaa aggattaaag atgctaagag atagtgatga tatttcataa   240
ataatgtaat tctatatatg ttaattacct tttttgcgag gcatatttat ggtgaaggat   300 aagtttttgac catcaaagaa ggttaatgtg gctgtggttt cagggtccat aaagcttttc   360
aattcatctt tttttttttt gttctttttt ttgattccgg tttctttgaa attttttttga   420 ttcggtaatc tccgagcaga aggaagaacg aaggaaggag cacagactta gattggtata   480
tatacgcata tgtggtgttg aagaaacatg aaattgccca gtattcttaa cccaactgca   540
cagaacaaaa acctgcagga aacgaagata aatcatgtcg aaagctacat ataaggaacg   600
tgctgctact catcctagtc ctgttgctgc caagctattt aatatcatgc acgaaaagca   660
aacaaacttg tgtgcttcat tggatgttcg taccaccaag gaattactgg agttagttga   720
agcattaggt cccaaaattt gtttactaaa aacacatgtg gatatcttga ctgatttttc   780
```

```
catggagggc acagttaagc cgctaaaggc attatccgcc aagtacaatt ttttactctt    840
cgaagacaga aaatttgctg acattggtaa tacagtcaaa ttgcagtact ctgcgggtgt    900
atacagaata gcagaatggg cagacattac gaatgcacac ggtgtggtgg gcccaggtat    960
tgttagcggt ttgaagcagg cggcagaaga agtaacaaag gaacctagag gcctttttgat  1020
gttagcagaa ttgtcatgca agggctccct atctactgga gaatatacta agggtactgt   1080
tgacattgcg aagagtgaca aagattttgt tatcggcttt attgctcaaa gagacatggg   1140
tggaagagat gaaggttacg attggttgat tatgacaccc ggtgtgggtt tagatgacaa   1200
gggagacgca ttgggtcaac agtatagaac cgtggatgat gtggtctcta caggatctga   1260
cattattatt gttggaagag gactatttgc aaagggaagg gatgctaagg tagagggtga   1320
acgttacaga aaagcaggct gggaagcata tttgagaaga tgcggccagc aaaactaaaa   1380
aactgtatta taagtaaatg catgtatact aaactcacaa attagagctt caatttaatt   1440
atatcagtta ttacccggga atctcggtcg taatgatttc tataatgacg aaaaaaaaaa   1500
aattggaaag aaaaagcttc atggcccttta taaaaaggaa ctatccaata cctcgccaga   1560
accaagtaac agtattttac ggggcacaaa tcaagaacaa taagacagga ctgtaaagat   1620
ggacgcatga tgcacgagcg caacgctcac aagatccgat cgaccgagaa ctgagaacgg   1680
tgcaatgatc aacatgatct                                               1700

<210> SEQ ID NO 90
<211> LENGTH: 1702
<212> TYPE: DNA
<213> ORGANISM: Artificial Sequence
<220> FEATURE:
<223> OTHER INFORMATION: xMarker xM0.URA.PI-MgaI

<400> SEQUENCE: 90
aagatccgat cgaccgagaa ctgagaacgg tgcaatgatc aacatgatct gcgtagctgc     60
ccagtatgag tcaggttcat catctcatgg atctgcacat gaacaaacac cagagtcaaa    120
cgacgttgaa attgaggcta ctgcgccaat tgatgacaat acagacgatg ataacaaacc    180
gaagttatct gatgtagaaa aggattaaag atgctaagag atagtgatga tatttcataa    240
ataatgtaat tctatatatg ttaattacct tttttgcgag gcatatttat ggtgaaggat    300
aagttttgac catcaaagaa ggttaatgtg gctgtggttt cagggtccat aaagcttttc    360
aattcatctt tttttttttt gttctttttt ttgattccgg tttctttgaa attttttga    420
ttcggtaatc tccgagcaga aggaagaacg aaggaaggag cacagactta gattggtata    480
tatacgcata tgtggtgttg aagaaacatg aaattgccca gtattcttaa cccaactgca    540
cagaacaaaa acctgcagga aacgaagata aatcatgtcg aaagctacat ataaggaacg    600
tgctgctact catcctagtc ctgttgctgc caagctattt aatatcatgc acgaaaagca    660
aacaaacttg tgtgcttcat tggatgttcg taccaccaag gaattactgg agttagttga    720
agcattaggt cccaaaattt gtttactaaa aacacatgtg gatatcttga ctgattttc    780
catggagggc acagttaagc cgctaaaggc attatccgcc aagtacaatt ttttactctt    840
cgaagacaga aaatttgctg acattggtaa tacagtcaaa ttgcagtact ctgcgggtgt    900
atacagaata gcagaatggg cagacattac gaatgcacac ggtgtggtgg gcccaggtat    960
tgttagcggt ttgaagcagg cggcagaaga agtaacaaag gaacctagag gcctttttgat 1020
gttagcagaa ttgtcatgca agggctccct atctactgga gaatatacta agggtactgt   1080
tgacattgcg aagagtgaca aagattttgt tatcggcttt attgctcaaa gagacatggg   1140
```

| | |
|---|---:|
| tggaagagat gaaggttacg attggttgat tatgacaccc ggtgtgggtt tagatgacaa | 1200 |
| gggagacgca ttgggtcaac agtatagaac cgtggatgat gtggtctcta caggatctga | 1260 |
| cattattatt gttggaagag gactatttgc aaagggaagg gatgctaagg tagagggtga | 1320 |
| acgttacaga aaagcaggct gggaagcata tttgagaaga tgcggccagc aaaactaaaa | 1380 |
| aactgtatta taagtaaatg catgtatact aaactcacaa attagagctt caatttaatt | 1440 |
| atatcagtta ttacccggga atctcggtcg taatgatttc tataatgacg aaaaaaaaaa | 1500 |
| aattggaaag aaaaagcttc atggccttta taaaaggaa ctatccaata cctcgccaga | 1560 |
| accaagtaac agtattttac ggggcacaaa tcaagaacaa taagacagga ctgtaaagat | 1620 |
| ggacgcatgc gtagctgccc agtatgagtc agaagatccg atcgaccgag aactgagaac | 1680 |
| ggtgcaatga tcaacatgat ct | 1702 |

<210> SEQ ID NO 91
<211> LENGTH: 1732
<212> TYPE: DNA
<213> ORGANISM: Artificial Sequence
<220> FEATURE:
<223> OTHER INFORMATION: xMarker xM0.URA.PI-MtuII

<400> SEQUENCE: 91

| | |
|---|---:|
| aagatccgat cgaccgagaa ctgagaacgg tgcaatgatc aacatgatct acgtgcacta | 60 |
| cgtagagggt cgcaccgcac cgatctacaa gttcatcatc tcatggatct gcacatgaac | 120 |
| aaacaccaga gtcaaacgac gttgaaattg aggctactgc gccaattgat gacaatacag | 180 |
| acgatgataa caaaccgaag ttatctgatg tagaaaagga ttaaagatgc taagagatag | 240 |
| tgatgatatt tcataaataa tgtaattcta tatatgttaa ttaccttttt tgcgaggcat | 300 |
| atttatggtg aaggataagt tttgaccatc aaagaaggtt aatgtggctg tggtttcagg | 360 |
| gtccataaag cttttcaatt catctttttt ttttttgttc ttttttttga ttccggtttc | 420 |
| tttgaaattt ttttgattcg gtaatctccg agcagaagga agaacgaagg aaggagcaca | 480 |
| gacttagatt ggtatatata cgcatatgtg gtgttgaaga acatgaaat tgcccagtat | 540 |
| tcttaaccca actgcacaga acaaaaacct gcaggaaacg aagataaatc atgtcgaaag | 600 |
| ctacatataa ggaacgtgct gctactcatc ctagtcctgt tgctgccaag ctatttaata | 660 |
| tcatgcacga aaagcaaaca aacttgtgtg cttcattgga tgttcgtacc accaaggaat | 720 |
| tactggagtt agttgaagca ttaggtccca aaatttgttt actaaaaaca catgtggata | 780 |
| tcttgactga tttttccatg gagggcacag ttaagccgct aaaggcatta tccgccaagt | 840 |
| acaattttt actcttcgaa gacagaaaat ttgctgacat tggtaataca gtcaaattgc | 900 |
| agtactctgc gggtgtatac agaatagcag aatgggcaga cattacgaat gcacacggtg | 960 |
| tggtgggccc aggtattgtt agcggtttga agcaggcggc agaagaagta acaaaggaac | 1020 |
| ctagaggcct tttgatgtta gcagaattgt catgcaaggg ctccctatct actggagaat | 1080 |
| atactaaggg tactgttgac attgcgaaga gtgacaaaga ttttgttatc ggctttattg | 1140 |
| ctcaaagaga catgggtgga agagatgaag gttacgattg gttgattatg acacccggtg | 1200 |
| tgggtttaga tgacaaggga gacgcattgg gtcaacagta tagaaccgtg gatgatgtgg | 1260 |
| tctctacagg atctgacatt attattgttg gaagaggact atttgcaaag ggaagggatg | 1320 |
| ctaaggtaga gggtgaacgt tacagaaaag caggctggga agcatatttg agaagatgcg | 1380 |
| gccagcaaaa ctaaaaaact gtattataag taaatgcatg tatactaaac tcacaaatta | 1440 |
| gagcttcaat ttaattatat cagttattac ccgggaatct cggtcgtaat gatttctata | 1500 |

| atgacgaaaa aaaaaaaatt ggaaagaaaa agcttcatgg cctttataaa aaggaactat | 1560 |
| ccaatacctc gccagaacca agtaacagta ttttacgggg cacaaatcaa gaacaataag | 1620 |
| acaggactgt aaagatggac gcatacgtgc actacgtaga gggtcgcacc gcaccgatct | 1680 |
| acaagatccg atcgaccgag aactgagaac ggtgcaatga tcaacatgat ct | 1732 |

<210> SEQ ID NO 92
<211> LENGTH: 1716
<212> TYPE: DNA
<213> ORGANISM: Artificial Sequence
<220> FEATURE:
<223> OTHER INFORMATION: xMarker xM0.URA.VDE

<400> SEQUENCE: 92

| aagatccgat cgaccgagaa ctgagaacgg tgcaatgatc aacatgatct tatgtcgggt | 60 |
| gcggagaaag aggtaatgaa agttcatcat ctcatggatc tgcacatgaa caaacaccag | 120 |
| agtcaaacga cgttgaaatt gaggctactg cgccaattga tgacaataca gacgatgata | 180 |
| acaaaccgaa gttatctgat gtagaaaagg attaaagatg ctaagagata gtgatgatat | 240 |
| ttcataaata atgtaattct atatatgtta attaccttt ttgcgaggca tatttatggt | 300 |
| gaaggataag ttttgaccat caaagaaggt taatgtggct gtggtttcag ggtccataaa | 360 |
| gcttttcaat tcatcttttt ttttttttgtt ctttttttg attccggttt ctttgaaatt | 420 |
| tttttgattc ggtaatctcc gagcagaagg aagaacgaag gaaggagcac agacttagat | 480 |
| tggtatatat acgcatatgt ggtgttgaag aaacatgaaa ttgcccagta ttcttaaccc | 540 |
| aactgcacag aacaaaaacc tgcaggaaac gaagataaat catgtcgaaa gctacatata | 600 |
| aggaacgtgc tgctactcat cctagtcctg ttgctgccaa gctatttaat atcatgcacg | 660 |
| aaaagcaaac aaacttgtgt gcttcattgg atgttcgtac caccaaggaa ttactggagt | 720 |
| tagttgaagc attaggtccc aaaatttgtt tactaaaaac acatgtggat atcttgactg | 780 |
| attttttccat ggagggcaca gttaagccgc taaaggcatt atccgccaag tacaattttt | 840 |
| tactcttcga agacagaaaa tttgctgaca ttggtaatac agtcaaattg cagtactctg | 900 |
| cgggtgtata cagaatagca gaatgggcag acattacgaa tgcacacggt gtggtgggcc | 960 |
| caggtattgt tagcggttg aagcaggcgg cagaagaagt aacaaaggaa cctagaggcc | 1020 |
| ttttgatgtt agcagaattg tcatgcaagg gctccctatc tactggagaa tatactaagg | 1080 |
| gtactgttga cattgcgaag agtgacaaag attttgttat cggctttatt gctcaaagag | 1140 |
| acatgggtgg aagagatgaa ggttacgatt ggttgattat gacacccggt gtgggtttag | 1200 |
| atgacaaggg agacgcattg ggtcaacagt atagaaccgt ggatgatgtg gtctctacag | 1260 |
| gatctgacat tattattgtt ggaagaggac tatttgcaaa gggaagggat gctaaggtag | 1320 |
| agggtgaacg ttacagaaaa gcaggctggg aagcatattt gagaagatgc ggccagcaaa | 1380 |
| actaaaaaac tgtattataa gtaaatgcat gtatactaaa ctcacaaatt agagcttcaa | 1440 |
| tttaattata tcagttatta cccgggaatc tcggtcgtaa tgatttctat aatgacgaaa | 1500 |
| aaaaaaaat tggaaagaaa aagcttcatg gcctttataa aaaggaacta tccaatacct | 1560 |
| cgccagaacc aagtaacagt attttacggg gcacaaatca gaacaataa gacaggactg | 1620 |
| taaagatgga cgcattatgt cgggtgcgga gaaagaggta atgaaaaaga tccgatcgac | 1680 |
| cgagaactga gaacggtgca atgatcaaca tgatct | 1716 |

<210> SEQ ID NO 93
<211> LENGTH: 1604
<212> TYPE: DNA

<213> ORGANISM: Artificial Sequence
<220> FEATURE:
<223> OTHER INFORMATION: xMarker xM1.nat.F-CphI

<400> SEQUENCE: 93

```
cgttacgaag cacacactag ttagcgtcga gacacatagc gacgctagaa gatgcacgag    60
cgcaacgctc acaatcgaca ctagtaatac acatcatcgt cctacaagtt catcaaagtg   120
ttggacagac aactatacca gcatggatct cttgtatcgg ttcttttctc ccgctctctc   180
gcaataacaa tgaacactgg gtcaatcata gcctacacag gtgaacagag tagcgtttat   240
acagggttta tacggtgatt cctacggcaa aaatttttca tttctaaaaa aaaaaagaaa   300
aatttttctt tccaacgcta gaaggaaaag aaaaatctaa ttaaattgat ttggtgattt   360
tctgagagtt ccctttttca tatatcgaat tttgaatata aaaggagatc gaaaaaattt   420
ttctattcaa tctgttttct ggttttattt gatagttttt ttgtgtatta ttattatgga   480
ttagtactgg tttatatggg tttttctgta aacttctttt ttatttttagt ttgtttaatc   540
ttattttgag ttacattata gttccctaac tgcaagagaa gtaacattaa aaatgaccac   600
tcttgacgac acggcttacc ggtaccgcac cagtgtcccg ggggacgccg aggccatcga   660
ggcactggat gggtccttca ccaccgacac cgtcttccgc gtcaccgcca ccggggacgg   720
cttcaccctg cgggaggtgc cggtggaccc gcccctgacc aaggtgttcc ccgacgacga   780
atcggacgac gaatcggacg ccggggagga cggcgacccg gactcccgga cgttcgtcgc   840
gtacggggac gacggcgacc tggcgggctt cgtggtcgtc tcgtactccg gctggaaccg   900
ccggctgacc gtcgaggaca tcgaggtcgc cccggagcac cggggggcacg gggtcgggcg   960
cgcgttgatg gggctcgcga cggagttcgc ccgcgagcgg ggcgccgggc acctctggct  1020
ggaggtcacc aacgtcaacg caccggcgat ccacgcgtac cggcggatgg ggttcaccct  1080
ctgcggcctg acaccgccc tgtacgacgg caccgcctcg gacggcgagc aggcgctcta  1140
catgagcatg ccctgcccct gagtttaact tgatactact agatttttc tcttcattta  1200
taaaatttt ggttataatt gaagctttag aagtatgaaa aaatccttttt ttttcattct  1260
ttgcaaccaa aataagaagc ttcttttatt cattgaaatg atgaatataa acctaacaaa  1320
agaaaaagac tcgaatatca aacattaaaa aaaaataaaa gaggttatct gttttcccat  1380
ttagttggag tttgcatttt ctaatagata gaactctcaa ttaatgtgga tttagtttct  1440
ctgttcgttt ttttttgttt tgttctcact gtatttacat ttctatttag tatttagtta  1500
ttcatataat cttaacttct cgaggagctc gatgcacgag cgcaacgctc acaacgttac  1560
gaagcacaca ctagttagcg tcgagacaca tagcgacgct agaa                  1604
```

<210> SEQ ID NO 94
<211> LENGTH: 1604
<212> TYPE: DNA
<213> ORGANISM: Artificial Sequence
<220> FEATURE:
<223> OTHER INFORMATION: xMarker xM4.nat.F-CphI

<400> SEQUENCE: 94

```
ttaatcagcg cccagagact agcactgaat gatcaacggg tagttcacac gatgcacgag    60
cgcaacgctc acaatcgaca ctagtaatac acatcatcgt cctacaagtt catcaaagtg   120
ttggacagac aactatacca gcatggatct cttgtatcgg ttcttttctc ccgctctctc   180
gcaataacaa tgaacactgg gtcaatcata gcctacacag gtgaacagag tagcgtttat   240
acagggttta tacggtgatt cctacggcaa aaatttttca tttctaaaaa aaaaaagaaa   300
```

| | | | | |
|---|---|---|---|---|
| aatttttctt | tccaacgcta | gaaggaaaag | aaaaatctaa | ttaaattgat | ttggtgattt | 360 |
| tctgagagtt | ccctttttca | tatatcgaat | tttgaatata | aaaggagatc | gaaaaaattt | 420 |
| ttctattcaa | tctgttttct | ggttttattt | gatagttttt | ttgtgtatta | ttattatgga | 480 |
| ttagtactgg | tttatatggg | ttttctgta | taacttcttt | ttattttagt | ttgtttaatc | 540 |
| ttattttgag | ttacattata | gttccctaac | tgcaagagaa | gtaacattaa | aaatgaccac | 600 |
| tcttgacgac | acggcttacc | ggtaccgcac | cagtgtcccg | ggggacgccg | aggccatcga | 660 |
| ggcactggat | gggtccttca | ccaccgacac | cgtcttccgc | gtcaccgcca | ccggggacgg | 720 |
| cttcaccctg | cggagggtgc | cggtggaccc | gccctgacc | aaggtgttcc | ccgacgacga | 780 |
| atcggacgac | gaatcggacg | ccggggagga | cggcgacccg | gactcccgga | cgttcgtcgc | 840 |
| gtacggggac | gacggcgacc | tggcgggctt | cgtggtcgtc | tcgtactccg | gctggaaccg | 900 |
| ccggctgacc | gtcgaggaca | tcgaggtcgc | cccggagcac | cggggcacg | ggtcgggcg | 960 |
| cgcgttgatg | gggctcgcga | cggagttcgc | ccgcgagcgg | ggcgccgggc | acctctggct | 1020 |
| ggaggtcacc | aacgtcaacg | caccggcgat | ccacgcgtac | cggcggatgg | ggttcaccct | 1080 |
| ctgcggcctg | gacaccgccc | tgtacgacgg | caccgcctcg | gacggcgagc | aggcgctcta | 1140 |
| catgagcatg | ccctgcccct | gagtttaact | tgatactact | agattttttc | tcttcattta | 1200 |
| taaaatttt | ggttataatt | gaagctttag | aagtatgaaa | aatccttttt | ttttcattct | 1260 |
| ttgcaaccaa | aataagaagc | ttcttttatt | cattgaaatg | atgaatataa | acctaacaaa | 1320 |
| agaaaaagac | tcgaatatca | aacattaaaa | aaaaataaaa | gaggttatct | gtttttcccat | 1380 |
| ttagttggag | tttgcatttt | ctaatagata | gaactctcaa | ttaatgtgga | tttagtttct | 1440 |
| ctgttcgttt | ttttttgttt | tgttctcact | gtatttacat | ttctatttag | tatttagtta | 1500 |
| ttcatataat | cttaacttct | cgaggagctc | gatgcacgag | cgcaacgctc | acaattaatc | 1560 |
| agcgcccaga | gactagcact | gaatgatcaa | cgggtagttc | acac | | 1604 |

<210> SEQ ID NO 95
<211> LENGTH: 2060
<212> TYPE: DNA
<213> ORGANISM: Artificial Sequence
<220> FEATURE:
<223> OTHER INFORMATION: xMarker xM2.hph.F-CphI

<400> SEQUENCE: 95

| | | | | | |
|---|---|---|---|---|---|
| gtactgccta | gtagaaacgg | atctccacgt | actagagtcc | acctggtatc | gatgcacgag | 60 |
| cgcaacgctc | acaatcgaca | ctagtaatac | acatcatcgt | cctacaagtt | catcaaagtg | 120 |
| ttggacagac | aactatacca | gcatggatct | cttgtatcgg | ttcttttctc | ccgctctctc | 180 |
| gcaataacaa | tgaacactgg | gtcaatcata | gcctacacag | gtgaacagag | tagcgtttat | 240 |
| acagggttta | tacggtgatt | cctacggcaa | aaattttca | tttctaaaaa | aaaaaagaaa | 300 |
| aatttttctt | tccaacgcta | gaaggaaaag | aaaaatctaa | ttaaattgat | ttggtgattt | 360 |
| tctgagagtt | ccctttttca | tatatcgaat | tttgaatata | aaaggagatc | gaaaaaattt | 420 |
| ttctattcaa | tctgttttct | ggttttattt | gatagttttt | ttgtgtatta | ttattatgga | 480 |
| ttagtactgg | tttatatggg | ttttctgta | taacttcttt | ttattttagt | ttgtttaatc | 540 |
| ttattttgag | ttacattata | gttccctaac | tgcaagagaa | gtaacattaa | aaatgaaaaa | 600 |
| gcctgaactc | accgcgacgt | ctgtcgagaa | gtttctgatc | gaaaagttcg | acagcgtctc | 660 |
| cgacctgatg | cagctctcgg | agggcgaaga | atctcgtgct | ttcagcttcg | atgtaggagg | 720 |
| gcgtggatat | gtcctgcggg | taaatagctg | cgccgatggt | ttctacaaag | atcgttatgt | 780 |

```
ttatcggcac tttgcatcgg ccgcgctccc gattccggaa gtgcttgaca ttggggaatt      840
cagcgagagc ctgacctatt gcatctcccg ccgtgcacag ggtgtcacgt tgcaagacct      900
gcctgaaacc gaactgcccg ctgttctgca gccggtcgcg gaggccatgg atgcgatcgc      960
tgcggccgat cttagccaga cgagcgggtt cggcccattc ggaccgcaag gaatcggtca     1020
atacactaca tggcgtgatt tcatatgcgc gattgctgat ccccatgtgt atcactggca     1080
aactgtgatg gacgacaccg tcagtgcgtc cgtcgcgcag gctctcgatg agctgatgct     1140
ttgggccgag gactgccccg aagtccggca cctcgtgcac gcggatttcg gctccaacaa     1200
tgtcctgacg gacaatggcc gcataacagc ggtcattgac tggagcgagg cgatgttcgg     1260
ggattcccaa tacgaggtcg ccaacatctt cttctggagg ccgtggttgg cttgtatgga     1320
gcagcagacg cgctacttcg agcggaggca tccggagctt gcaggatcgc gcggctccg      1380 ggcgtatatg ctccgcattg gtcttgacca actctatcag agcttggttg acggcaattt     1440
cgatgatgca gcttgggcgc agggtcgatg cgacgcaatc gtccgatccg gagccgggac     1500
tgtcgggcgt acacaaatcg cccgcagaag cgcggccgtc tggaccgatg gctgtgtaga     1560
agtactcgcc gatagtggaa accgacgccc cagcactcgt ccgagggcaa aggaataggt     1620
ttaacttgat actactagat tttttctctt catttataaa attttggtt ataattgaag      1680 ctttagaagt atgaaaaaat ccttttttt cattctttgc aaccaaaata agaagcttct      1740
tttattcatt gaaatgatga atataaacct aacaaagaa aaagactcga atatcaaaca      1800
ttaaaaaaaa ataaaagagg ttatctgttt tcccatttag ttggagtttg cattttctaa     1860
tagatagaac tctcaattaa tgtggattta gtttctctgt tcgttttttt ttgttttgtt     1920
ctcactgtat ttcatttct atttagtatt tagttattca tataatctta acttctcgag      1980
gagctcgatg cacgagcgca acgctcacaa gtactgccta gtagaaacgg atctccacgt     2040
actagagtcc acctggtatc                                                  2060

<210> SEQ ID NO 96
<211> LENGTH: 1844
<212> TYPE: DNA
<213> ORGANISM: Artificial Sequence
<220> FEATURE:
<223> OTHER INFORMATION: xMarker xM3.kan.F-CphI

<400> SEQUENCE: 96
cgaggattaa cgtgtaaggc cctaagctat gtaccgcatc tcctaagaga gatgcacgag       60
cgcaacgctc acaatcgaca ctagtaatac acatcatcgt cctacaagtt catcaaagtg      120
ttggacagac aactatacca gcatggatct cttgtatcgg ttcttttctc ccgctctctc      180
gcaataacaa tgaacactgg gtcaatcata gcctacacag gtgaacagag tagcgtttat      240
acagggttta tacggtgatt cctacggcaa aaattttca tttctaaaaa aaaaagaaa       300 aatttttctt tccaacgcta gaaggaaaag aaaaatctaa ttaaattgat tggtgatttt     360
tctgagagtt ccctttttca tatatcgaat tttgaatata aaggagatc gaaaaatttt      420 ttctattcaa tctgttttct ggttttattt gatagttttt ttgtgtatta ttattatgga    480
ttagtactgg tttatatggg ttttttctgta aacttctttt ttattttagt ttgtttaatc    540
ttattttgag ttacattata gttccctaac tgcaagagaa gtaacattaa aaatgggtaa    600
ggaaaagact cacgtttcga ggccgcgatt aaattccaac atggatgctg atttatatgg     660
gtataaatgg gctcgcgata atgtcgggca atcaggtgcg acaatctatc gattgtatgg     720
gaagcccgat gcgccagagt tgtttctgaa acatggcaaa ggtagcgttg ccaatgatgt     780
```

```
tacagatgag atggtcagac taaactggct gacggaattt atgcctcttc cgaccatcaa    840
gcattttatc cgtactcctg atgatgcatg gttactcacc actgcgatcc ccggcaaaac    900
agcattccag gtattagaag aatatcctga ttcaggtgaa atattgttg atgcgctggc    960
agtgttcctg cgccggttgc attcgattcc tgtttgtaat tgtcctttta acagcgatcg   1020
cgtatttcgt ctcgctcagg cgcaatcacg aatgaataac ggtttggttg atgcgagtga   1080
ttttgatgac gagcgtaatg gctggcctgt gaacaagtc tggaaagaaa tgcataagct   1140
tttgccattc tcaccggatt cagtcgtcac tcatggtgat ttctcacttg ataaccttat   1200
ttttgacgag gggaaattaa taggttgtat tgatgttgga cgagtcggaa tcgcagaccg   1260
ataccaggat cttgccatcc tatggaactg cctcggtgag ttttctcctt cattacagaa   1320
acggcttttt caaaaatatg gtattgataa tcctgatatg aataaattgc agtttcattt   1380
gatgctcgat gagttttct aagtttaact tgatactact agatttttc tcttcattta   1440
taaaattttt ggttataatt gaagctttag aagtatgaaa aaatccttt ttttcattct   1500
ttgcaaccaa ataagaagc ttcttttatt cattgaaatg atgaatataa acctaacaaa   1560
agaaaaagac tcgaatatca aacattaaaa aaaaataaaa gaggttatct gttttcccat   1620
ttagttggag tttgcatttt ctaatagata gaactctcaa ttaatgtgga tttagtttct   1680
ctgttcgttt ttttttgttt tgttctcact gtatttacat ttctatttag tatttagtta   1740
ttcatataat cttaacttct cgaggagctc gatgcacgag cgcaacgctc acaacgagga   1800
ttaacgtgta aggccctaag ctatgtaccg catctcctaa gaga                   1844

<210> SEQ ID NO 97
<211> LENGTH: 1386
<212> TYPE: DNA
<213> ORGANISM: Artificial Sequence
<220> FEATURE:
<223> OTHER INFORMATION: xMarker xM6.zeo.F-CphI

<400> SEQUENCE: 97
gtcaaagcgc gattcgctag gaatgagagc gagaacgaac cggagtatat gatgcacgag     60
cgcaacgctc acaaaataca catcatcgtc ctacaagttc atcaaagtgt tggacagaca    120
actataccag catggatctc ttgtatcggt tctttctcc cgctctctcg caataacaat    180
gaacactggg tcaatcatag cctacacagg tgaacagagt agcgtttata cagggtttat    240
acggtgattc ctacggcaaa aattttcat ttctaaaaaa aaaagaaaa atttttcttt    300
ccaacgctag aaggaaaaga aaatctaat taaattgatt tggtgatttt ctgagagttc    360
cctttttcat atatcgaatt ttgaatataa aaggagatcg aaaaaatttt tctattcaat    420
ctgttttctg gttttatttg atagtttttt tgtgtattat tattatggat tagtactggt    480
ttatatgggt ttttctgtat aacttctttt tattttagtt tgtttaatct tatttgagt    540
tacattatag ttccctaact gcaagagaag taacattaaa aatggccaag ttgaccagtg    600
ccgttccggt gctcaccgcg cgcgacgtcg ccggagcggt cgagttctgg accgaccggc    660
tcgggttctc ccgggacttc gtggaggacg acttcgccgg tgtggtccgg gacgacgtga    720
ccctgttcat cagcgcggtc caggaccagg tggtgccgga caacaccctg gcctgggtgt    780
gggtgcgcgg cctggacgag ctgtacgccg agtggtcgga ggtcgtgtcc acgaacttcc    840
gggacgcctc cgggccggcc atgaccgaga tcggcgagca gccgtggggg cgggagttcg    900
ccctgcgcga cccggccggc aactgcgtgc acttcgtggc cgaggagcag gactgagttt    960
aacttgatac tactagattt tttctcttca tttataaaat ttttggttat aattgaagct   1020
```

```
ttagaagtat gaaaaaatcc tttttttttca ttctttgcaa ccaaaataag aagcttcttt    1080
tattcattga aatgatgaat ataaacctaa caaaagaaaa agactcgaat atcaaacatt    1140
aaaaaaaaat aaaagaggtt atctgttttc ccatttagtt ggagtttgca ttttctaata    1200
gatagaactc tcaattaatg tggatttagt ttctctgttc gtttttttt  gttttgttct    1260 cactgtattt acatttctat ttagtattta gttattcata taatcttaac ttgatgcacg    1320
agcgcaacgc tcacaagtca aagcgcgatt cgctaggaat gagagcgaga acgaaccgga    1380
gtatat                                                                1386
```

<210> SEQ ID NO 98
<211> LENGTH: 1630
<212> TYPE: DNA
<213> ORGANISM: Artificial Sequence
<220> FEATURE:
<223> OTHER INFORMATION: xMarker s20M.URA.I-SceI

<400> SEQUENCE: 98

```
aagatccgat cgaccgagaa tagggataac agggtaatat gcgtccatct ttacagtcct      60
gtcttattgt tcttgatttg tgccccgtaa aatactgtta cttggttctg gcgaggtatt     120
ggatagttcc ttttttataaa ggccatgaag cttttttcttt ccaattttttt ttttttcgtc    180 attatagaaa tcattacgac cgagattccc gggtaataac tgatataatt aaattgaagc     240
tctaatttgt gagtttagta tacatgcatt tacttataat acagtttttt agttttgctg     300
gccgcatctt ctcaaatatg cttcccagcc tgcttttctg taacgttcac cctctaccctt    360 agcatccctt ccctttgcaa atagtcctct tccaacaata ataatgtcag atcctgtaga     420
gaccacatca tccacggttc tatactgttg acccaatgcg tctcccttgt catctaaacc     480
cacaccgggt gtcataatca accaatcgta accttcatct cttccaccca tgtctctttg     540
agcaataaag ccgataacaa atctttgtc actcttcgca atgtcaacag tacccttagt      600
atattctcca gtagataggg agcccttgca tgacaattct gctaacatca aaaggcctct     660
aggttccttt gttacttctt ctgccgcctg cttcaaaccg ctaacaatac ctgggcccac    720
cacaccgtgt gcattcgtaa tgtctgccca ttctgctatt ctgtatacac ccgcagagta     780
ctgcaatttg actgtattac caatgtcagc aaattttctg tcttcgaaga gtaaaaaatt    840
gtacttggcg gataatgcct ttagcggctt aactgtgccc tccatggaaa aatcagtcaa     900
gatatccaca tgtgttttta gtaaacaaat tttgggacct aatgcttcaa ctaactccag     960
taattccttg gtggtacgaa catccaatga agcacacaag tttgtttgct tttcgtgcat    1020
gatattaaat agcttggcag caacaggact aggatgagta gcagcacgtt ccttatatgt    1080
agctttcgac atgatttatc ttcgtttcct gcaggttttt gttctgtgca gttgggttaa    1140
gaatactggg caatttcatg tttcttcaac accacatatg cgtatatata ccaatctaag    1200
tctgtgctcc ttccttcgtt cttccttctg ctcggagatt accgaatcaa aaaaatttca    1260
aagaaaccgg aatcaaaaaa aagaacaaaa aaaaaaaga tgaattgaaa agctttatgg    1320
accctgaaac cacagccaca ttaaccttct ttgatggtca aaactatcc ttcaccataa     1380 atatgcctcg caaaaaaggt aattaacata tatagaatta cattatttat gaaatatcat    1440
cactatctct tagcatcttt aatccttttc tacatcagat aacttcggtt tgttatcatc    1500
gtctgtattg tcatcaattg gcgcagtagc ctcaatttca acgtcgtttg actctggtgt    1560
ttgttcatgt gcagatccat gagatgatga actagggata acagggtaat aagatccgat    1620
cgaccgagaa                                                            1630
```

<210> SEQ ID NO 99
<211> LENGTH: 1670
<212> TYPE: DNA
<213> ORGANISM: Artificial Sequence
<220> FEATURE:
<223> OTHER INFORMATION: xMarker s40M.URA.I-SceI

<400> SEQUENCE: 99

```
aagatccgat cgaccgagaa ctgagaacgg tgcaatgatc tagggataac agggtaatat      60
gcgtccatct ttacagtcct gtcttattgt tcttgatttg tgccccgtaa aatactgtta     120
cttggttctg gcgaggtatt ggatagttcc tttttataaa ggccatgaag ctttttcttt     180 ccaattttttt tttttcgtc attatagaaa tcattacgac cgagattccc gggtaataac     240
tgatataatt aaattgaagc tctaatttgt gagtttagta tacatgcatt tacttataat     300
acagtttttt agttttgctg gccgcatctt ctcaaatatg cttcccagcc tgcttttctg     360
taacgttcac cctctacctt agcatccctt cccttttgcaa atagtcctct tccaacaata     420
ataatgtcag atcctgtaga gaccacatca tccacggttc tatactgttg acccaatgcg     480
tctcccttgt catctaaacc cacaccgggt gtcataatca accaatcgta accttcatct     540
cttccaccca tgtctctttg agcaataaag ccgataacaa aatctttgtc actcttcgca     600
atgtcaacag taccctttagt atattctcca gtagatagggg agcccttgca tgacaattct     660
gctaacatca aaaggcctct aggttccttt gttacttctt ctgccgcctg cttcaaaccg     720
ctaacaatac ctgggcccac cacaccgtgt gcattcgtaa tgtctgccca ttctgctatt     780
ctgtatacac ccgcagagta ctgcaatttg actgtattac caatgtcagc aaattttctg     840
tcttcgaaga gtaaaaaatt gtacttggcg gataatgcct ttagcggctt aactgtgccc     900
tccatggaaa aatcagtcaa gatatcccaca tgtgttttta gtaaacaaat tttgggacct     960
aatgcttcaa ctaactccag taattccttg gtggtacgaa catccaatga agcacacaag    1020 tttgttttgct tttcgtgcat gatattaaat agcttggcag caacaggact aggatgagta    1080
gcagcacgtt ccttatatgt agcttttcgac atgatttatc ttcgtttcct gcaggttttt    1140
gttctgtgca gttgggttaa gaatactggg caatttcatg tttcttcaac accacatatg    1200
cgtatatata ccaatctaag tctgtgctcc ttccttcgtt cttccttctg ctcggagatt    1260
accgaatcaa aaaatttca agaaaccgg aatcaaaaaa aagaacaaaa aaaaaaaga    1320 tgaattgaaa agctttatgg accctgaaac cacagccaca ttaaccttct ttgatggtca    1380
aaacttatcc ttcaccataa atatgcctcg caaaaaaggt aattaacata tatagaatta    1440
cattatttat gaaatatcat cactatctct tagcatcttt aatccttttc tacatcagat    1500
aacttcggtt tgttatcatc gtctgtattg tcatcaattg gcgcagtagc ctcaatttca    1560
acgtcgtttg actctggtgt tgttcatgt gcagatccat gagatgatga actagggata    1620
acagggtaat aagatccgat cgaccgagaa ctgagaacgg tgcaatgatc               1670
```

<210> SEQ ID NO 100
<211> LENGTH: 1710
<212> TYPE: DNA
<213> ORGANISM: Artificial Sequence
<220> FEATURE:
<223> OTHER INFORMATION: xMarker s60M.URA.I-SceI

<400> SEQUENCE: 100

```
aagatccgat cgaccgagaa ctgagaacgg tgcaatgatc aacatgatct gcgacgagct      60
tagggataac agggtaatat gcgtccatct ttacagtcct gtcttattgt tcttgatttg     120
```

```
tgccccgtaa aatactgtta cttggttctg gcgaggtatt ggatagttcc ttttttataaa    180 ggccatgaag cttttctt ccaattttt ttttttcgtc attatagaaa tcattacgac        240
cgagattccc gggtaataac tgatataatt aaattgaagc tctaatttgt gagtttagta    300
tacatgcatt tacttataat acagtttttt agttttgctg gccgcatctt ctcaaatatg    360
cttcccagcc tgcttttctg taacgttcac cctctacctt agcatcccctt cccttttgcaa  420 atagtcctct tccaacaata ataatgtcag atcctgtaga gaccacatca tccacggttc    480
tatactgttg acccaatgcg tctcccttgt catctaaacc cacaccgggt gtcataatca    540
accaatcgta accttcatct cttccaccca tgtctctttg agcaataaag ccgataacaa    600
aatctttgtc actcttcgca atgtcaacag taccctttagt atattctcca gtagataggg   660
agcccttgca tgacaattct gctaacatca aaaggcctct aggttccttt gttacttctt    720
ctgccgcctg cttcaaaccg ctaacaatac ctgggcccac cacaccgtgt gcattcgtaa    780
tgtctgccca ttctgctatt ctgtatacac ccgcagagta ctgcaatttg actgtattac    840
caatgtcagc aaattttctg tcttcgaaga gtaaaaaatt gtacttggcg ataatgcct    900 ttagcggctt aactgtgccc tccatggaaa aatcagtcaa gatatcccaca tgtgttttta   960 gtaaacaaat tttgggacct aatgcttcaa ctaactccag taattccttg gtggtacgaa    1020
catccaatga agcacacaag tttgtttgct tttcgtgcat gatattaaat agcttggcag    1080
caacaggact aggatgagta gcagcacgtt ccttatatgt agctttcgac atgatttatc    1140
ttcgtttcct gcaggttttt gttctgtgca gttgggttaa gaatactggg caatttcatg   1200
tttcttcaac accacatatg cgtatatata ccaatctaag tctgtgctcc ttccttcgtt    1260
cttccttctg ctcggagatt accgaatcaa aaaaatttca agaaaccgg aatcaaaaaa    1320 aagaacaaaa aaaaaaaga tgaattgaaa agctttatgg accctgaaac cacagccaca    1380
ttaaccttct ttgatggtca aaacttatcc ttcaccataa atatgcctcg caaaaaaggt    1440
aattaacata tatagaatta cattatttat gaaatatcat cactatctct tagcatcttt    1500
aatccttttc tacatcagat aacttcggtt tgttatcatc gtctgtattg tcatcaattg    1560
gcgcagtagc ctcaatttca acgtcgtttg actctggtgt tgttcatgt gcagatccat     1620 gagatgatga actagggata acagggtaat aagatccgat cgaccgagaa ctgagaacgg    1680
tgcaatgatc aacatgatct gcgacgagct                                     1710

<210> SEQ ID NO 101
<211> LENGTH: 62
<212> TYPE: DNA
<213> ORGANISM: Artificial Sequence
<220> FEATURE:
<223> OTHER INFORMATION: Primer KB589-324-35

<400> SEQUENCE: 101
atccccgcgt gcttggccgg ccgtatgttg atcccaaaga agaagagaaa ggtcgagttg    60
gg                                                                   62

<210> SEQ ID NO 102
<211> LENGTH: 51
<212> TYPE: DNA
<213> ORGANISM: Artificial Sequence
<220> FEATURE:
<223> OTHER INFORMATION: Primer 00177-JD-75AN

<400> SEQUENCE: 102
atccccgcgt gcttggccgg ccgtatgaag aacatcaaga agaaccaggt c              51
```

```
<210> SEQ ID NO 103
<211> LENGTH: 51
<212> TYPE: DNA
<213> ORGANISM: Artificial Sequence
<220> FEATURE:
<223> OTHER INFORMATION: Primer KB591-324-36

<400> SEQUENCE: 103
atccccgcgt gcttggccgg ccgtatgact aagttgtatt ctgacttgta c        51

<210> SEQ ID NO 104
<211> LENGTH: 45
<212> TYPE: DNA
<213> ORGANISM: Artificial Sequence
<220> FEATURE:
<223> OTHER INFORMATION: Primer KB592-324-36

<400> SEQUENCE: 104
atcggcgctc gcggcctgca ggttttagtt atggactgca aaacc                45

<210> SEQ ID NO 105
<211> LENGTH: 48
<212> TYPE: DNA
<213> ORGANISM: Artificial Sequence
<220> FEATURE:
<223> OTHER INFORMATION: Primer KB593-324-36

<400> SEQUENCE: 105
atcggcgctc gcggcctgca ggttttagtt atgaactact aatccctc             48

<210> SEQ ID NO 106
<211> LENGTH: 47
<212> TYPE: DNA
<213> ORGANISM: Artificial Sequence
<220> FEATURE:
<223> OTHER INFORMATION: Primer 00177-JD-75AO

<400> SEQUENCE: 106
atcggcgctc gcggcctgca ggttctactt gaggaacgtc tcggaag              47

<210> SEQ ID NO 107
<211> LENGTH: 52
<212> TYPE: DNA
<213> ORGANISM: Artificial Sequence
<220> FEATURE:
<223> OTHER INFORMATION: Primer KB595-324-36

<400> SEQUENCE: 107
atcggcgctc gcggcctgca ggttttactg atatcttttc aaatacttta tc        52

<210> SEQ ID NO 108
<211> LENGTH: 31
<212> TYPE: DNA
<213> ORGANISM: Artificial Sequence
<220> FEATURE:
<223> OTHER INFORMATION: Endonuclease recognition/cleavage site (ES)
      VDE (PI-SceI)

<400> SEQUENCE: 108
tatgtcgggt gcggagaaag aggtaatgaa a                               31

<210> SEQ ID NO 109
<211> LENGTH: 24
<212> TYPE: DNA
<213> ORGANISM: Artificial Sequence
<220> FEATURE:
<223> OTHER INFORMATION: Endonuclease recognition/cleavage site (ES)
```

-continued

F-CphI

<400> SEQUENCE: 109
gatgcacgag cgcaacgctc acaa                                              24

<210> SEQ ID NO 110
<211> LENGTH: 24
<212> TYPE: DNA
<213> ORGANISM: Artificial Sequence
<220> FEATURE:
<223> OTHER INFORMATION: Endonuclease recognition/cleavage site (ES)
      PI-MgaI (pps1)

<400> SEQUENCE: 110
gcgtagctgc ccagtatgag tcag                                              24

<210> SEQ ID NO 111
<211> LENGTH: 40
<212> TYPE: DNA
<213> ORGANISM: Artificial Sequence
<220> FEATURE:
<223> OTHER INFORMATION: Endonuclease recognition/cleavage site (ES)
      PI-MtuII (pps1)

<400> SEQUENCE: 111
acgtgcacta cgtagagggt cgcaccgcac cgatctacaa                              40

<210> SEQ ID NO 112
<211> LENGTH: 18
<212> TYPE: DNA
<213> ORGANISM: Artificial Sequence
<220> FEATURE:
<223> OTHER INFORMATION: Endonuclease recognition/cleavage site (ES)
      I-SceI

<400> SEQUENCE: 112
tagggataac agggtaat                                                     18

<210> SEQ ID NO 113
<211> LENGTH: 49
<212> TYPE: DNA
<213> ORGANISM: Artificial Sequence
<220> FEATURE:
<223> OTHER INFORMATION: Oligonucleotide KB411-266-26

<400> SEQUENCE: 113
aagatccgat cgaccgagaa tagggataac agggtaatcg actctagac                    49

<210> SEQ ID NO 114
<211> LENGTH: 44
<212> TYPE: DNA
<213> ORGANISM: Artificial Sequence
<220> FEATURE:
<223> OTHER INFORMATION: Oligonucleotide KB412-266-26

<400> SEQUENCE: 114
gagtcgatta ccctgttatc cctattctcg gtcgatcgga tctt                         44

<210> SEQ ID NO 115
<211> LENGTH: 69
<212> TYPE: DNA
<213> ORGANISM: Artificial Sequence
<220> FEATURE:
<223> OTHER INFORMATION: Oligonucleotide KB415-266-26

<400> SEQUENCE: 115
aagatccgat cgaccgagaa ctgagaacgg tgcaatgatc tagggataac agggtaatcg        60

```
actctagac                                                              69

<210> SEQ ID NO 116
<211> LENGTH: 64
<212> TYPE: DNA
<213> ORGANISM: Artificial Sequence
<220> FEATURE:
<223> OTHER INFORMATION: Oligonucleotide KB416-266-26

<400> SEQUENCE: 116
gagtcgatta ccctgttatc cctagatcat tgcaccgttc tcagttctcg gtcgatcgga      60
tctt                                                                   64

<210> SEQ ID NO 117
<211> LENGTH: 64
<212> TYPE: DNA
<213> ORGANISM: Artificial Sequence
<220> FEATURE:
<223> OTHER INFORMATION: Oligonucleotide KB419-266-27

<400> SEQUENCE: 117
gagtcgtagg gataacaggg taataagatc cgatcgaccg agaactgaga acggtgcaat      60
gatc                                                                   64

<210> SEQ ID NO 118
<211> LENGTH: 69
<212> TYPE: DNA
<213> ORGANISM: Artificial Sequence
<220> FEATURE:
<223> OTHER INFORMATION: Oligonucleotide KB420-266-27

<400> SEQUENCE: 118
gatcattgca ccgttctcag ttctcggtcg atcggatctt attaccctgt tatccctacg      60
actcgtcta                                                              69

<210> SEQ ID NO 119
<211> LENGTH: 46
<212> TYPE: DNA
<213> ORGANISM: Artificial Sequence
<220> FEATURE:
<223> OTHER INFORMATION: Oligonucleotide KB421-266-27

<400> SEQUENCE: 119
gagtcgaaga tccgatcgac cgagaactga gaacggtgca atgatc                     46

<210> SEQ ID NO 120
<211> LENGTH: 40
<212> TYPE: DNA
<213> ORGANISM: Artificial Sequence
<220> FEATURE:
<223> OTHER INFORMATION: Oligonucleotide KB423-266-27

<400> SEQUENCE: 120
agctcgtcgc agatcatgtt gatcattgca ccgttctcag                            40

<210> SEQ ID NO 121
<211> LENGTH: 20
<212> TYPE: DNA
<213> ORGANISM: Artificial Sequence
<220> FEATURE:
<223> OTHER INFORMATION: Oligonucleotide KB424-266-27

<400> SEQUENCE: 121
aacatgatct gcgacgagct                                                  20
```

<210> SEQ ID NO 122
<211> LENGTH: 20
<212> TYPE: DNA
<213> ORGANISM: Artificial Sequence
<220> FEATURE:
<223> OTHER INFORMATION: Oligonucleotide KB425-266-27

<400> SEQUENCE: 122
ttctcggtcg atcggatctt                                          20

<210> SEQ ID NO 123
<211> LENGTH: 24
<212> TYPE: DNA
<213> ORGANISM: Artificial Sequence
<220> FEATURE:
<223> OTHER INFORMATION: Oligonucleotide KB426-266-27

<400> SEQUENCE: 123
gagtcgatta ccctgttatc ccta                                     24

<210> SEQ ID NO 124
<211> LENGTH: 40
<212> TYPE: DNA
<213> ORGANISM: Artificial Sequence
<220> FEATURE:
<223> OTHER INFORMATION: Oligonucleotide KB427-266-27

<400> SEQUENCE: 124
aagatccgat cgaccgagaa ctgagaacgg tgcaatgatc                    40

<210> SEQ ID NO 125
<211> LENGTH: 49
<212> TYPE: DNA
<213> ORGANISM: Artificial Sequence
<220> FEATURE:
<223> OTHER INFORMATION: Oligonucleotide KB428-266-27

<400> SEQUENCE: 125
aacatgatct gcgacgagct tagggataac agggtaatcg actctagac          49

<210> SEQ ID NO 126
<211> LENGTH: 49
<212> TYPE: DNA
<213> ORGANISM: Artificial Sequence
<220> FEATURE:
<223> OTHER INFORMATION: Oligonucleotide KB429-266-27

<400> SEQUENCE: 126
ttctcggtcg atcggatctt attaccctgt tatccctacg actcgtcta          49

<210> SEQ ID NO 127
<211> LENGTH: 31
<212> TYPE: DNA
<213> ORGANISM: Artificial Sequence
<220> FEATURE:
<223> OTHER INFORMATION: Oligonucleotide KB430-266-28

<400> SEQUENCE: 127
ttctcggtcg atcggatctt cgactcgtct a                             31

<210> SEQ ID NO 128
<211> LENGTH: 44
<212> TYPE: DNA
<213> ORGANISM: Artificial Sequence
<220> FEATURE:
<223> OTHER INFORMATION: Oligonucleotide KB431-266-28

```
<400> SEQUENCE: 128
gagtcgatta ccctgttatc cctagtcagc catttgcatc ctca                        44

<210> SEQ ID NO 129
<211> LENGTH: 40
<212> TYPE: DNA
<213> ORGANISM: Artificial Sequence
<220> FEATURE:
<223> OTHER INFORMATION: Oligonucleotide KB432-266-28

<400> SEQUENCE: 129
aacatgatct gcgacgagct tgaggatgca aatggctgac                              40

<210> SEQ ID NO 130
<211> LENGTH: 29
<212> TYPE: DNA
<213> ORGANISM: Artificial Sequence
<220> FEATURE:
<223> OTHER INFORMATION: Oligonucleotide KB433-266-28

<400> SEQUENCE: 130
tagggataac agggtaatcg actctagac                                         29

<210> SEQ ID NO 131
<211> LENGTH: 20
<212> TYPE: DNA
<213> ORGANISM: Artificial Sequence
<220> FEATURE:
<223> OTHER INFORMATION: Oligonucleotide KB434-266-28

<400> SEQUENCE: 131
gtcagccatt tgcatcctca                                                   20

<210> SEQ ID NO 132
<211> LENGTH: 25
<212> TYPE: DNA
<213> ORGANISM: Artificial Sequence
<220> FEATURE:
<223> OTHER INFORMATION: Oligonucleotide KB439-266-34

<400> SEQUENCE: 132
taatatgcgt ccatctttac agtcc                                             25

<210> SEQ ID NO 133
<211> LENGTH: 26
<212> TYPE: DNA
<213> ORGANISM: Artificial Sequence
<220> FEATURE:
<223> OTHER INFORMATION: Oligonucleotide KB440-266-34

<400> SEQUENCE: 133
cctagttcat catctcatgg atctgc                                            26

<210> SEQ ID NO 134
<211> LENGTH: 26
<212> TYPE: DNA
<213> ORGANISM: Artificial Sequence
<220> FEATURE:
<223> OTHER INFORMATION: Oligonucleotide KB441-266-34

<400> SEQUENCE: 134
tcttgttcat catctcatgg atctgc                                            26

<210> SEQ ID NO 135
<211> LENGTH: 44
```

```
<212> TYPE: DNA
<213> ORGANISM: Artificial Sequence
<220> FEATURE:
<223> OTHER INFORMATION: Oligonucleotide KB464-266-58

<400> SEQUENCE: 135
gagtcgtagg gataacaggg taataagatc cgatcgaccg agaa                          44

<210> SEQ ID NO 136
<211> LENGTH: 1750
<212> TYPE: DNA
<213> ORGANISM: Artificial Sequence
<220> FEATURE:
<223> OTHER INFORMATION: xMarker s80M.URA.I-SceI

<400> SEQUENCE: 136
aagatccgat cgaccgagaa ctgagaacgg tgcaatgatc aacatgatct gcgacgagct          60
tgaggatgca aatggctgac tagggataac agggtaatat gcgtccatct ttacagtcct         120
gtcttattgt tcttgatttg tgccccgtaa atactgttac cttggttctg gcgaggtatt         180
ggatagttcc tttttataaa ggccatgaag cttttctttt ccaattttt tttttcgtc           240 attatagaaa tcattacgac cgagattccc gggtaataac tgatataatt aaattgaagc         300
tctaatttgt gagtttagta tacatgcatt tacttataat acagtttttt agttttgctg         360
gccgcatctt ctcaaatatg cttcccagcc tgcttttctg taacgttcac cctctacctt         420
agcatccctt ccctttgcaa atagtcctct ccaacaata ataatgtcag atcctgtaga          480
gaccacatca tccacggttc tatactgttg acccaatgcg tctcccttgt catctaaacc         540
cacaccgggt gtcataatca accaatcgta accttcatct cttccaccca tgtctctttg         600
agcaataaag ccgataacaa atctttgtc actcttcgca atgtcaacag tacccttagt         660
atattctcca gtagataggg agcccttgca tgacaattct gctaacatca aaaggcctct         720
aggttccttt gttacttctt ctgccgcctg cttcaaaccg ctaacaatac ctgggcccac         780
cacaccgtgt gcattcgtaa tgtctgccca ttctgctatt ctgtatacac ccgcagagta         840
ctgcaatttg actgtattac caatgtcagc aaattttctg tcttcgaaga gtaaaaaatt        900
gtacttggcg gataatgcct ttagcggctt aactgtgccc tccatggaaa aatcagtcaa         960
gatatccaca tgtgttttta gtaaacaaat tttgggacct aatgcttcaa ctaactccag        1020
taattccttg gtggtacgaa catccaatga agcacacaag tttgtttgct tttcgtgcat        1080
gatattaaat agcttggcag caacaggact aggatgagta gcagcacgtt ccttatatgt        1140
agctttcgac atgatttatc ttcgtttcct gcaggttttt gttctgtgca gttgggttaa        1200
gaatactggg caatttcatg tttcttcaac accacatatg cgtatatata ccaatctaag        1260
tctgtgctcc ttccttcgtt cttccttctg ctcggagatt accgaatcaa aaaaatttca        1320
aagaaaccgg aatcaaaaaa aagaacaaaa aaaaaaaaga tgaattgaaa agctttatgg        1380
accctgaaac cacagccaca ttaaccttct ttgatggtca aaacttatcc ttcaccataa        1440
atatgcctcg caaaaaaggt aattaacata tatagaatta cattatttat gaaatatcat        1500
cactatctct tagcatcttt aatccttttc tacatcagat aacttcggtt tgttatcatc        1560
gtctgtattg tcatcaattg gcgcagtagc ctcaatttca acgtcgtttg actctggtgt        1620
ttgttcatgt gcagatccat gagatgatga actagggata acagggtaat aagatccgat        1680
cgaccgagaa ctgagaacgg tgcaatgatc aacatgatct gcgacgagct tgaggatgca        1740
aatggctgac                                                              1750
```

```
<210> SEQ ID NO 137
<211> LENGTH: 35
<212> TYPE: DNA
<213> ORGANISM: Artificial Sequence
<220> FEATURE:
<223> OTHER INFORMATION: Figure 3 oligo 1
<220> FEATURE:
<221> NAME/KEY: misc_feature
<222> LOCATION: (28)...(35)
<223> OTHER INFORMATION: N = A, G, C or T

<400> SEQUENCE: 137
accgatagtt acgatcgagg tactcatnnn nnnnn                              35

<210> SEQ ID NO 138
<211> LENGTH: 34
<212> TYPE: DNA
<213> ORGANISM: Artificial Sequence
<220> FEATURE:
<223> OTHER INFORMATION: Figure 3 oligo 2
<220> FEATURE:
<221> NAME/KEY: misc_feature
<222> LOCATION: (28)...(34)
<223> OTHER INFORMATION: N = A, G, C or T

<400> SEQUENCE: 138
agtagtacct cgatcgtaac tatcggtnnn nnnn                               34

<210> SEQ ID NO 139
<211> LENGTH: 35
<212> TYPE: DNA
<213> ORGANISM: Artificial Sequence
<220> FEATURE:
<223> OTHER INFORMATION: Figure 3 oligo 3
<220> FEATURE:
<221> NAME/KEY: misc_feature
<222> LOCATION: (28)...(35)
<223> OTHER INFORMATION: N = A, G, C or T

<400> SEQUENCE: 139
accgatagtt acgatcgagg tactactnnn nnnnn                              35

<210> SEQ ID NO 140
<211> LENGTH: 34
<212> TYPE: DNA
<213> ORGANISM: Artificial Sequence
<220> FEATURE:
<223> OTHER INFORMATION: Figure 3 oligo 4
<220> FEATURE:
<221> NAME/KEY: misc_feature
<222> LOCATION: (28)...(35)
<223> OTHER INFORMATION: N = A, G, C or T

<400> SEQUENCE: 140
agtagtacct cgatcgtaac tatcggtnnn nnnn                               34

<210> SEQ ID NO 141
<211> LENGTH: 36
<212> TYPE: DNA
<213> ORGANISM: Artificial Sequence
<220> FEATURE:
<223> OTHER INFORMATION: Figure 4 oligo 3

<400> SEQUENCE: 141
accgatagtt acgatcgagg tactcattag ggataa                             36

<210> SEQ ID NO 142
<211> LENGTH: 41
<212> TYPE: DNA
<213> ORGANISM: Artificial Sequence
```

```
-continued

<220> FEATURE:
<223> OTHER INFORMATION: Figure 4 oligo 4

<400> SEQUENCE: 142
agtagtacct cgatcgtaac tatcggttat taccctgtta t                    41

<210> SEQ ID NO 143
<211> LENGTH: 27
<212> TYPE: DNA
<213> ORGANISM: Artificial Sequence
<220> FEATURE:
<223> OTHER INFORMATION: Figure 4 oligo 5

<400> SEQUENCE: 143
accgatagtt acgatcgagg tactcat                                    27

<210> SEQ ID NO 144
<211> LENGTH: 27
<212> TYPE: DNA
<213> ORGANISM: Artificial Sequence
<220> FEATURE:
<223> OTHER INFORMATION: Figure 4 oligo 6

<400> SEQUENCE: 144
atgagtacct cgatcgtaac tatcggt                                    27
```

NUCLEIC ACIDS, COMPOSITIONS AND METHODS FOR THE EXCISION OF TARGET NUCLEIC ACIDS

Figure 1:
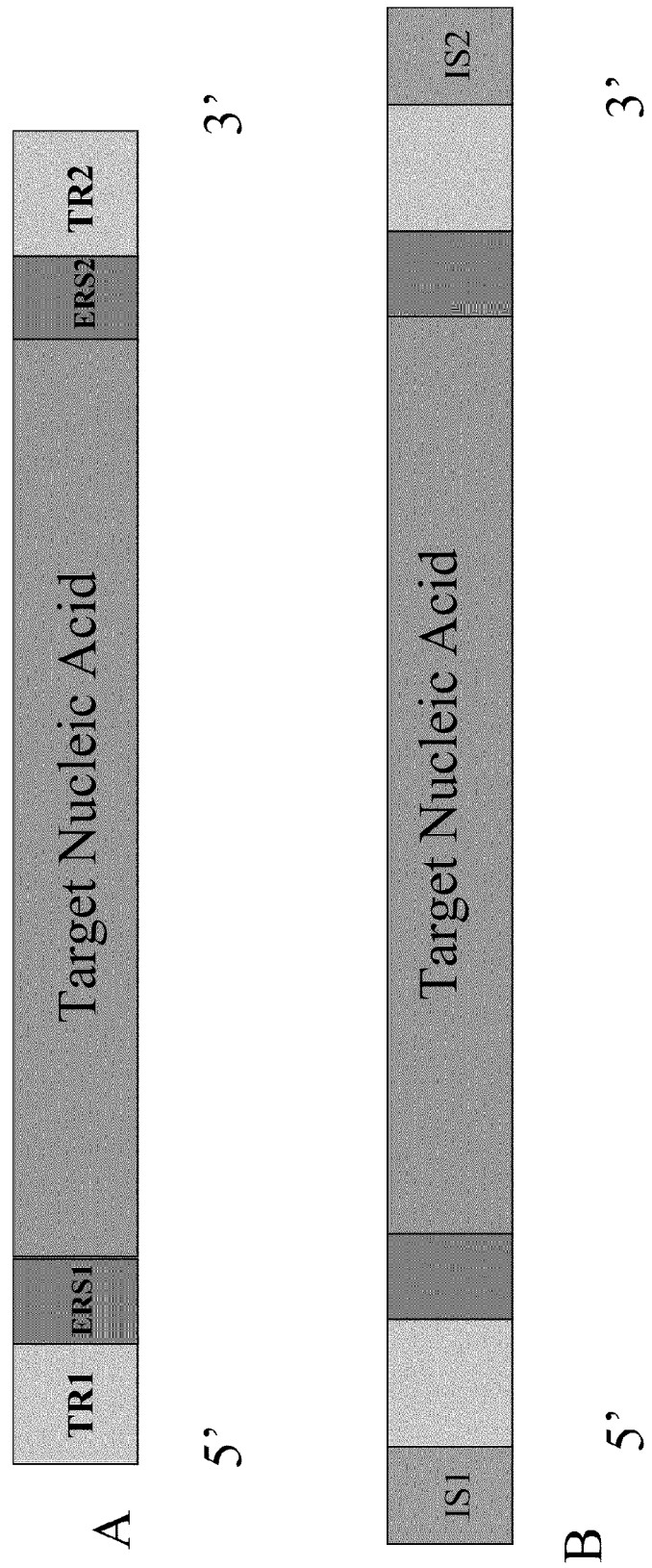

This application claims benefit under 35 U.S.C. §119(e) of U.S. Provisional Application No. 61/378,350, filed Aug. 30, 2010, which is hereby incorporated by reference in its entirety.

1. FIELD OF THE INVENTION

The nucleic acids, compositions, and methods provided herein generally relate to the fields of molecular biology and genetic engineering.

2. BACKGROUND

Genetic engineering techniques to excise a target nucleic acid from a host cell genome or an episome are needed in a variety of fields including metabolic engineering, industrial microbiology, synthetic biology, and basic molecular genetics research. Previous methods for removal of target nucleic acids, however, have been restricted and limited in application. Site specific recombinase methods of removal, for example, leave behind deleterious specific recombinase binding sites that create potential genomic instabilities within the host cells. Other methods can produce excision events at low frequency, thus necessitating methods for growth-selection of rare host cells that undergo the excision event. There exists a need for nucleic acids, compositions, and methods that can allow for high frequency and high fidelity excision of a target nucleic acid from a host cell genome or an episome without creating potential genomic instabilities.

3. SUMMARY

Provided herein are nucleic acids, compositions, and methods that allow for the excision of one or more loci from the genome of a host cell. In a first aspect, provided herein is an excisable nucleic acid construct comprising, in a 5' to 3' orientation: a) a first tandem repeat nucleic acid, b) a first homing endonuclease recognition site, c) a target nucleic acid, d) a second homing endonuclease recognition site and e) a second tandem repeat nucleic acid. In some embodiments, the excisable nucleic acid construct is integrated into the host cell genome.

The first and second homing endonuclease recognition sites allow for a homing endonuclease to cleave the excisable nucleic acid construct. A homing endonuclease bound to a homing endonuclease recognition site can cleave the excisable nucleic acid construct at or adjacent to the homing endonuclease recognition site. In some embodiments, each of the first and second homing endonuclease recognition sites independently comprises 20-40 nucleotide base pairs. In some embodiments, each of the homing endonuclease recognition sites independently consists of 20-40 nucleotide base pairs. In some embodiments, each of the homing endonuclease recognition sites independently consists of 25-40 nucleotide base pairs. In some embodiments, each of the homing endonuclease recognition sites independently consists of 30-40 nucleotide base pairs. In some embodiments, each of the homing endonuclease recognition sites independently consists of 35-40 nucleotide base pairs. In some embodiments, each of the homing endonuclease recognition sites independently consists of 24 nucleotide base pairs.

In some embodiments, at least one of the first or second homing endonuclease recognition sites is a recognition site for a homing endonuclease selected from the group consisting of: an LAGLIDADG (SEQ ID NO: 1) homing endonuclease, an HNH homing endonuclease, a His-Cys box homing endonuclease, a GIY-YIG (SEQ ID NO: 2) homing endonuclease, and a cyanobacterial homing endonuclease. In certain embodiments, each of the first and second homing endonuclease recognition sites independently is a recognition site for a homing endonuclease selected from the group consisting of: an LAGLIDADG (SEQ ID NO: 1) homing endonuclease, an HNH homing endonuclease, a His-Cys box homing endonuclease, a GIY-YIG (SEQ ID NO: 2) homing endonuclease, and a cyanobacterial homing endonuclease.

In some embodiments, at least one of the first or second homing endonuclease recognition sites is a recognition site for a homing endonuclease selected from the group consisting of: I-CreI, I-MsoI, I-SceI, I-SceIV, H-DreI, I-HmuI, I-PpoI, I-DirI, I-NjaI, I-NanI, I-NitI, I-TevI, I-TevII, I-TevIII, F-TevI, F-TevII, F-CphI, PI-MgaI, I-CsmI, I-CeuI, and PI-SceI. In certain embodiments, each of the first and second homing endonuclease recognition sites independently is a recognition site for a homing endonuclease selected from the group consisting of: I-CreI, I-MsoI, I-SceI, I-SceIV, H-DreI, I-HmuI, I-PpoI, I-DirI, I-NjaI, I-NanI, I-NitI, I-TevI, I-TevII, I-TevIII, F-TevI, F-TevII, F-CphI, PI-MgaI, I-CsmI, I-CeuI, and PI-SceI. In particular embodiments, at least one of the first or second homing endonuclease recognition sites is a recognition site for I-SceI. In particular embodiments, at least one of the first or second homing endonuclease recognition sites is a recognition site for F-CphI.

After cleavage of the target nucleic acid, repair of the host cell genome can occur through intrachromosomal recombination facilitated by the first and second tandem repeats. In some embodiments, each of the first and second tandem repeat nucleic acids independently comprises at least 18 nucleotide base pairs. In some embodiments, each of the first and second tandem repeat nucleic acids independently comprises 18-80 nucleotide base pairs. In some embodiments, each of the first and second tandem repeat nucleic acids independently consists of 18-50 nucleotide base pairs.

In some embodiments, the target nucleic acid encodes a selectable marker. In some embodiments, the selectable marker is selected from the group consisting of: URA3, hygromycin B phosphotransferase, aminoglycoside phosphotransferase, zeocin resistance gene and phosphinothricin N-acetyltransferase.

In some embodiments, the excisable nucleic acid construct described above further comprises a first genomic integration site linked 5' of the first tandem repeat and a second genomic integration site linked 3' of the second tandem repeat. Advantageously, the first and second genomic integration sites can facilitate integration of the excisable nucleic acid construct into a host cell genome.

In another aspect, provided herein is a host cell comprising the excisable nucleic acid construct described above. In some embodiments, the excisable nucleic acid construct further comprises a first integration site linked 5' of the first tandem repeat and a second integration site linked 3' of the second tandem repeat.

In some embodiments, the host cell is a prokaryote. In some embodiments, the host cell is a eukaryote. In certain embodiments, the host cell is a unicellular eukaryotic organism. In certain embodiments, the host cell is a yeast cell. In certain embodiments, the host cell is a haploid yeast cell. In other embodiments, the host cell is a diploid yeast cell. In certain embodiments, the host cell is a yeast cell of the strain *S. cerevisiae*.

In some embodiments the host cell further comprises a vector comprising a homing endonuclease nucleic acid encoding a homing endonuclease, wherein the homing endonuclease is capable of binding to and cleaving at or adjacent to at least one of the first or second homing endonuclease recognition sites. In certain embodiments, the vector comprises a homing endonuclease nucleic acid encoding a homing endonuclease capable of binding to and cleaving at or adjacent to each of the first and second homing endonuclease recognition sites.

In some embodiments, the vector comprises a promoter element that controls the expression of the homing endonuclease nucleic acid encoding the homing endonuclease. In some embodiments, the promoter element is an inducible promoter. In some embodiments, the promoter element is a constitutive promoter.

In another aspect, provided herein is a host cell comprising an excisable nucleic acid construct described above, integrated into the host cell genome. In certain embodiments, the excisable nucleic acid construct comprises, in a 5' to 3' orientation: a) a first tandem repeat nucleic acid, b) a first homing endonuclease recognition site, c) a target nucleic acid, d) a second homing endonuclease recognition site and e) a second tandem repeat nucleic acid. In some embodiments, the host cell further comprises a vector comprising a homing endonuclease nucleic acid that encodes a homing endonuclease capable of binding to and cleaving at or adjacent to at least one of the first or second homing endonuclease recognition sites. In some embodiments, the homing endonuclease nucleic acid encodes a homing endonuclease capable of binding to and cleaving at or adjacent to each of the first and second homing endonuclease recognition sites. In some embodiments, the homing endonuclease is I-SceI. In some embodiments, the homing endonuclease is F-CphI.

In another aspect, provided herein is a kit comprising the excisable nucleic acid construct described above; and a vector comprising a homing endonuclease nucleic acid encoding a homing endonuclease capable of binding to and cleaving at or adjacent to at least one of the first or second homing endonuclease recognition sites. In some embodiments, the homing endonuclease is I-SceI. In some embodiments, the homing endonuclease is F-CphI.

In another aspect, provided herein is a method of excising at least one target nucleic acid from the genome of a host cell. In certain embodiments, the host cell comprises a nucleic acid, in a 5' to 3' orientation: a) a first tandem repeat nucleic acid, b) a first homing endonuclease recognition site, c) a target nucleic acid, d) a second homing endonuclease recognition site and e) a second tandem repeat nucleic acid. In certain embodiments, the method comprises expressing a homing endonuclease in the host cell such that the homing endonuclease cleaves at or adjacent to at least one of the first or second homing endonuclease recognition sites. In some embodiments of the method, the homing endonuclease cleaves at or adjacent to each of the first and second homing endonuclease recognition sites. In some embodiments, at least one of the first or second homing endonuclease recognition sites is a recognition site for I-SceI. at least one of the first or second homing endonuclease recognition sites is a recognition site for F-CphI.

Advantageously, a genomic nucleic acid with an excision of the target nucleic acid is formed by recombination mediated by the first and second tandem repeat. In some embodiments, the newly formed genomic nucleic acid comprises a third tandem repeat, created as a product of the recombination of the first and second tandem repeats. In advantageous embodiments, the only portion of the excisable endonuclease construct remaining in the host cell is the third tandem repeat, which can be as few as 18 nucleotide base pairs in length.

The compositions and methods provided herein advantageously allow for the precise and efficient excision of a target nucleic acid from a host cell genome or an episome without creating potential genomic instabilities. Many instances in genetic engineering exist where there may be a need to remove a target nucleic acid at a chosen genomic or episomal location. For example, the compositions and method described above can advantageously be used for removing selection markers to enable their reuse in the same host cell or its progeny. "Marker recycling" may be useful in situations requiring multiple genetic engineering events in a host organism with a limited battery of selectable markers. The compositions and methods provided may also be used to remove unwanted nucleic acids (e.g. an antibiotic resistance marker) from a host cell before releasing the host cell in a manufacturing or natural environment.

Further, the compositions and method described can be used for turning on or off expression of a particular gene in a host cell and its progeny. To turn off a gene, the compositions and methods described can be used, for example, to excise the nucleic acids representing one or more of the gene's cis-acting regulatory elements, some or all of its coding sequence, or one or more of its transcriptional activators. To turn on expression of a gene, an interfering stretch of nucleic acids can be excised to create required adjacent interactions between the elements needed for expression of the particular gene.

4. BRIEF DESCRIPTION OF THE FIGURES

FIG. 1. Embodiments of an excisable nucleic acid construct. FIG. 1A: An excisable nucleic acid construct comprising, in a 5' to 3' orientation: a first tandem repeat nucleic acid ("TR1"); a first homing endonuclease recognition site ("ERS1"); a target nucleic acid ("Target nucleic acid"); a second homing endonuclease recognition site ("ERS2"); and a second tandem repeat nucleic acid ("TR2"). FIG. 1B: The excisable nucleic acid construct depicted in FIG. 1A, further comprising a first integration site (IS1) linked 5' of the first homing endonuclease recognition site and a second integration site (IS2) linked 3' of the second tandem repeat nucleic acid.

Figure 2:
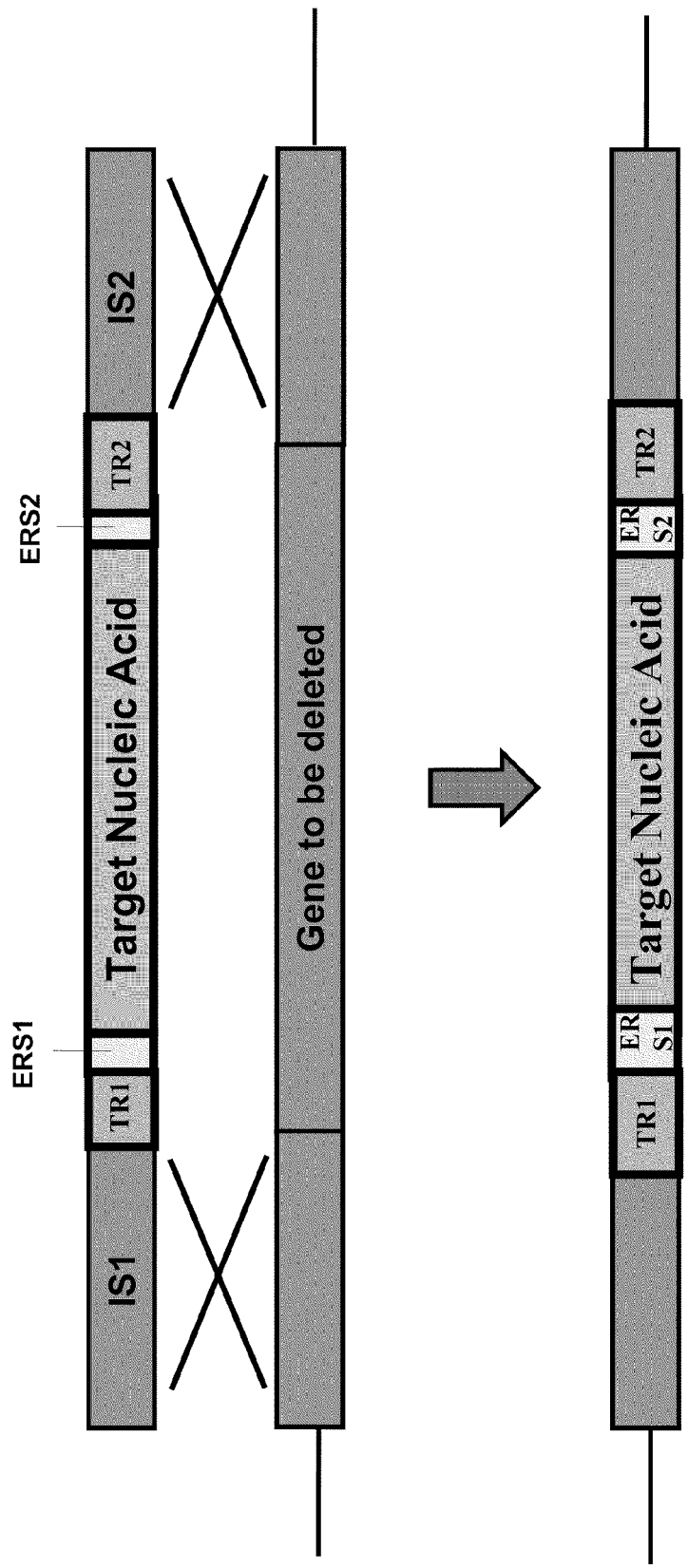

FIG. 2. An excisable nucleic acid construct is transformed to knock-out and/or knock-in a target nucleic acid into a specific locus of the host cell genome through integration site (IS) mediated homologous recombination. The target nucleic acid is flanked by two copies of a homing endonuclease restriction site (ER) which in turn are flanked by two tandem repeats (TR) sequences that direct repair after cleavage.

Figure 3:
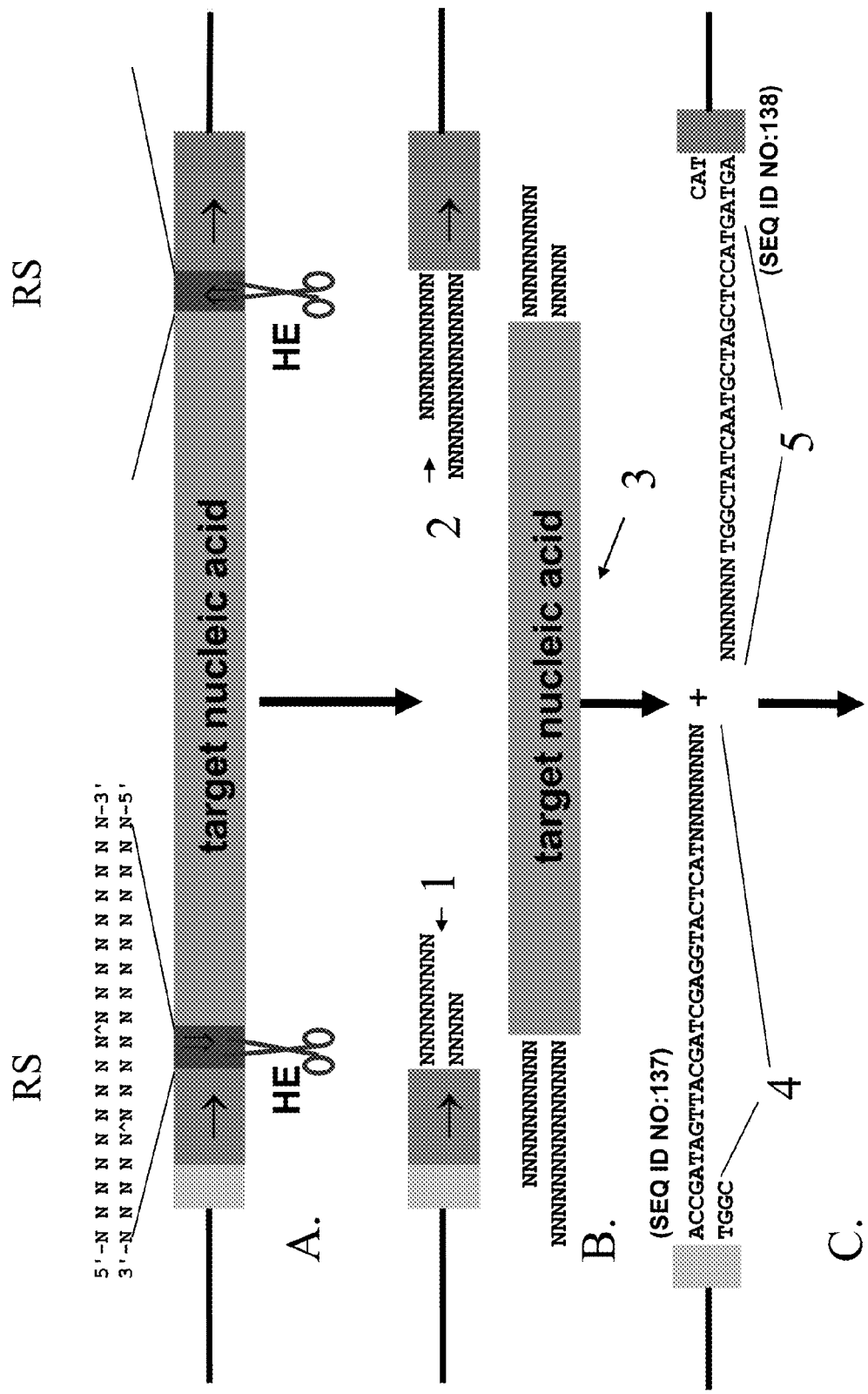

FIG. 3. Excision of a target nucleic acid. In some embodiments, cleavage of each of the first and second homing (FIG. 3A) endonuclease recognition sites (RS) by corresponding homing endonucleases (HE) creates three nucleic acid fragments: (1) a left arm of genomic or episomal nucleic acid (2) a nucleic acid fragment comprising the target nucleic acid and (3) a right arm of genomic or episomal nucleic acid (FIG. 3B). After cleavage, endogenous 5' to 3' exonucleases in the host cell rapidly degrade one strand of each nucleic acid fragment, destroying the nucleic acid fragment comprising the target nucleic acid and leaving 3' tails on the left (4) and right arms (5) of genomic or episomal nucleic acid (FIG. 3C).

Figure 4:
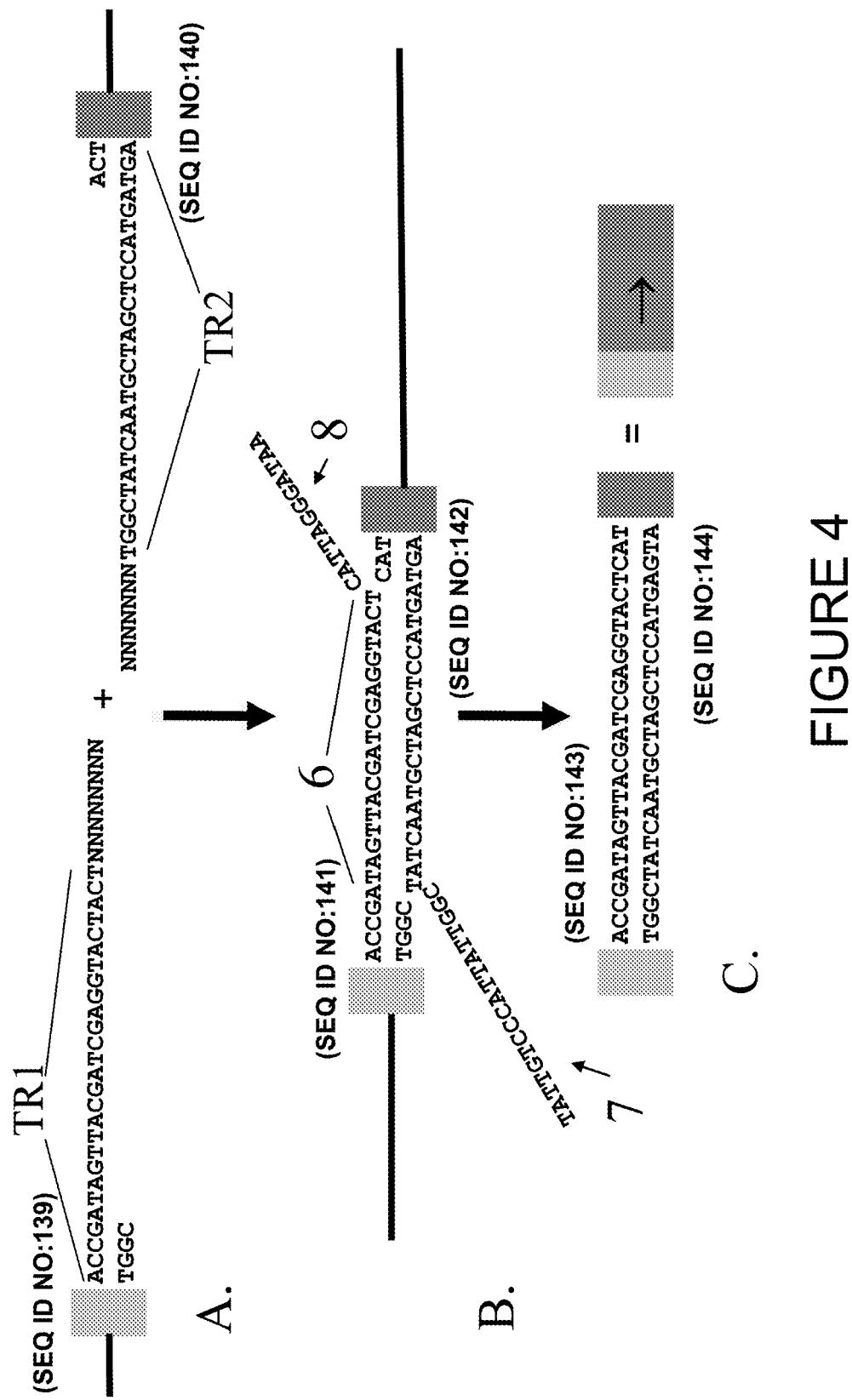

FIG. 4. Excision of a target nucleic acid (cont'd). The single strand degradation of the left and right arms expose a tandem repeat found on each arm, the tandem repeats complementary to one another (FIG. 4A). The complementary regions on the tandem repeats form a heteroduplex (FIG. 4B,6) and undergo recombination facilitated by host cell proteins. The extreme 3' ends of the single strand of the right (7) and left arms (8) are not complementary and thus are not part of the heteroduplex formed by the complementary portions of the first and second tandem repeats. These extreme non complementary 3' ends can be cleaved by a flap nuclease. Finally, repair DNA synthesis and DNA ligase fill in the heteroduplex and seal nicks, creating an intact genomic or episomal nucleic acid with a precise excision of the target nucleic acid (FIG. 4C).

5. DETAILED DESCRIPTION OF THE EMBODIMENTS

5.1 Definitions

As used herein, the term "homing endonuclease" refers to any one of several endonucleases whose natural biological function is to catalyze a gene conversion event to spread the endonuclease-encoding allele of a particular gene to endonuclease-free alleles of the gene. See, e.g., Chevalier, *Nucleic Acids Res* 1(29): 3757-74 (2001); Jacquier, *Cell* 41: 383-94 (1985). At least five different families of homing endonucleases are known, including: 1) LAGLIDADG (SEQ ID NO: 1) homing endonucleases, 2) HNH homing endonucleases, 3) His-Cys box homing endonucleases, 4) GIY-YIG (SEQ ID NO: 2) homing endonucleases and 5) cyanobacterial homing endonucleases. See, e.g., Stoddard, *Quarterly Review of Biophysics* 38(1): 49-95 (2006). Examples of specific homing endonucleases from these families include but are not limited to: I-CreI, I-MsoI, I-SceI, I-SceIV, H-DreI, I-HmuI, I-PpoI, I-DirI, I-NjaI, I-NanI, I-NitI, I-TevI, I-TevII, I-TevIII, F-TevI, F-TevII, F-CphI, PI-MgaI, I-CsmI, I-CeuI, and PI-SceI.

As used herein, the term "homing endonuclease recognition site" refers to a nucleic acid that is recognized by a specific homing endonuclease. Subsequent to binding of the homing endonuclease recognition site, the homing endonuclease can create a double strand break at or adjacent to the homing endonuclease recognition site.

As used herein, the term "adjacent" refers to a distance of about 1 to about 100, 1 to about 75, 1 to about 50, 1 to about 25, 1 to about 20, 1 to about 15, 1 to about 10, or 1 to about 5 nucleotides from a particular nucleic acid.

As used herein, the terms "cleaves" and cleavage" with respect to homing endonucleases refer to the act of creating a double stranded break in a particular nucleic acid. The double strand break can leave a blunt end or sticky end (i.e., 5' or 3' overhang), as understood by those of skill in the art.

As used herein, the term "tandem repeat" refers to a nucleic acid that is part of a group of two or more nucleic acids, wherein each member shares sufficient nucleotide homology with respect to the other member(s) to mediate recombination between one another. Tandem repeats are arranged in either the same orientation ("direct tandem repeat") or in the opposite orientation ("inverted tandem repeat") with respect to the other member of the tandem.

As used herein, the term "target DNA segment" refers to any target DNA segment that is to be excised from a host cell genome using the compositions and methods provided herein. Useful examples include but are not limited to: a protein-coding sequence, selectable marker, reporter gene, fluorescent marker coding sequence, promoter, enhancer, terminator, transcriptional activator, transcriptional repressor, transcriptional activator binding site, transcriptional repressor binding site, intron, exon, poly-A tail, multiple cloning site, nuclear localization signal, mRNA stabilization signal, integration loci, epitope tag coding sequence, degradation signal, or any other naturally occurring or synthetic DNA molecule. In some embodiments, the target DNA segment can be of natural origin. Alternatively, a target DNA segment can be completely of synthetic origin, produced in vitro. Furthermore, a target DNA segment can comprise any combination of isolated naturally occurring DNA molecules, or any combination of an isolated naturally occurring DNA molecule and a synthetic DNA molecule. For example, a target DNA segment may comprise a heterologous promoter operably linked to a protein coding sequence, a protein coding sequence linked to a poly-A tail, a protein coding sequence linked in-frame with a epitope tag coding sequence, and the like.

As used herein, the term "vector" is used in reference to extrachromosomal nucleic acid molecules capable of replication in a cell and to which an insert sequence can be operatively linked so as to bring about replication of the insert sequence. Useful examples include but are not limited to circular DNA molecules such as plasmid constructs, phage constructs, cosmid vectors, etc., as well as linear nucleic acid constructs (e.g., lambda phage constructs, bacterial artificial chromosomes (BACs), yeast artificial chromosomes (YACs), etc.). A vector may include expression signals such as a promoter and/or a terminator, a selectable marker such as a gene conferring resistance to an antibiotic, and one or more restriction sites into which insert sequences can be cloned. Vectors can have other unique features (such as the size of DNA insert they can accommodate).

As used herein, the term "genomic" refers to both chromosomal and episomal DNA contained in a host cell.

5.2 Excisable Nucleic Acid Constructs

In one aspect, provided herein is an excisable nucleic acid construct comprising, in a 5' to 3' orientation: a) a first tandem repeat (DR1), b) a target DNA segment (D), and c) a second tandem repeat (DR2), as well as a first homing endonuclease recognition site (ES1) located either between DR1 and D or between D and DR2, and optionally a second homing endonuclease recognition site (ES2) located either between D and DR2 or between DR1 and D, respectively (FIG. 1A). Thus, in some embodiments, the excisable nucleic acid construct comprises, in a 5' to 3' orientation: a) a first tandem repeat (DR1), b) a first homing endonuclease recognition site (ES1), c) a target DNA segment (D), and d) a second tandem repeat (DR2). In some embodiments, the excisable nucleic acid construct comprises, in a 5' to 3' orientation: a) a first tandem repeat (DR1), b) a target DNA segment (D), c) a first homing endonuclease recognition site (ES1), and d) a second tandem repeat (DR2). In some embodiments, the excisable nucleic acid construct comprises, in a 5' to 3' orientation: a) a first tandem repeat (DR1), b) a first homing endonuclease recognition site (ES1), c) a target DNA segment (D), d) a second homing endonuclease recognition site (ES2), and e) a second tandem repeat (DR2).

In some embodiments, the excisable nucleic acid construct described above further comprises a first genomic integration site (IS1) linked 5' of the first tandem repeat and a second genomic integration site linked 3' of the second tandem repeat (IS2). Thus, in some embodiments, the excisable nucleic acid construct comprises, in a 5' to 3' orientation: a) a first integration site (IS1), b) a first tandem repeat (DR1), c) a first homing endonuclease recognition site (ES1), d) a target DNA segment (D), e) a second tandem repeat (DR2), and f) a second integration site (IS2). In some embodiments, the excisable nucleic acid construct comprises, in a 5' to 3' orientation: a)

first integration site (IS1), b) a first tandem repeat (DR1), c) a target DNA segment (D), d) a first homing endonuclease recognition site (ES1), e) a second tandem repeat (DR2), and f) a second integration site (IS2). In some embodiments, the excisable nucleic acid construct comprises, in a 5' to 3' orientation: a) a first integration site (IS1), b) a first tandem repeat (DR1), c) a first homing endonuclease recognition site (ES1), d) a target DNA segment (D), e) a second homing endonuclease recognition site (ES2), f) a second tandem repeat (DR2), and g) a second integration site (IS2).

Advantageously, the first and second integration sites can facilitate integration of the excisable nucleic acid construct into a host cell genome. The excisable nucleic acid construct, when integrated into a host cell genome, allows for high frequency and high fidelity excision of the target DNA segment (D) from the host cell genome. In some embodiments, the excisable nucleic acid construct is a linear DNA molecule.

The excisable nucleic acid construct may be used to facilitate the excision of selection markers in genetic engineering applications or for the removal of antibiotic resistance markers before release of organisms into a manufacturing environment or the natural environment. It may also be used to permanently turn on or turn off expression of genes in a host cell and its descendents. To prevent expression of a gene, its cis-acting regulatory sequences, its coding sequence, or a gene encoding a transcriptional activator can be excised. To trigger expression of genes, the gene or DNA binding site for a transcriptional repressor can be excised to allow expression of its regulated gene(s), or an interfering stretch of DNA can be excised to create required adjacent interactions between the elements needed for expression of particular genes.

The excisable nucleic acid construct can be generated by any technique apparent to one skilled in the art. In certain embodiments, the excisable nucleic acid construct is generated using polymerase chain reaction (PCR) and molecular cloning techniques well known in the art. See, e.g., *PCR Technology: Principles and Applications for DNA Amplification*, ed. HA Erlich, Stockton Press, New York, N.Y. (1989); Sambrook et al., 2001, *Molecular Cloning—A Laboratory Manual*, 3$^{rd}$ edition, Cold Spring Harbor Laboratory, Cold Spring Harbor, N.Y.; *PCR Technology: Principles and Applications for DNA Amplification*, ed. H A Erlich, Stockton Press, New York, N.Y. (1989).

Each element of the excisable nucleic acid construct is discussed in detail below.

5.2.1. Homing Endonuclease Recognition Sites

The excisable nucleic acid construct comprises at least a first homing endonuclease recognition site (ES1), and optionally a second homing endonuclease recognition site (ES2). In some embodiments where the excisable nucleic acid construct comprises only a first homing endonuclease recognition site, ES1 can be positioned 3' of the first tandem repeat (DR1) and 5' of the target DNA segment (D), or 3' of the target DNA segment (D) and 5' of the second tandem repeat (DR2). In some embodiments where the excisable nucleic acid construct comprises a first and a second homing endonuclease recognition site, ES1 is positioned 3' of the first tandem repeat (DR1) and 5' of the target DNA segment (D), and ES2 is positioned 3' of the target DNA segment (D) and 5' of the second tandem repeat (DR2).

Homing endonuclease recognition sites allow for a corresponding homing endonuclease to cleave the excisable nucleic acid construct at or adjacent to the homing endonuclease recognition site.

Homing endonuclease recognition sites range from 14-40 nucleotide base pairs in length. In some embodiments, each homing endonuclease recognition site consists of 14-40 nucleotides. In some embodiments, each homing endonuclease recognition site consists of 18-40 nucleotides. In some embodiments, each homing endonuclease recognition site consists of 20-40 nucleotides. In some embodiments, each homing endonuclease recognition site consists of 25-40 nucleotides. In some embodiments, each homing endonuclease recognition site consists of 30-40 nucleotides. In some embodiments, each homing endonuclease recognition site consists of 35-40 nucleotides. In some embodiments, each homing endonuclease recognition site consists of 14, 15, 16, 17, 18, 19, 20, 21, 22, 23, 24, 25, 26, 27, 28, 29, 30, 31, 32, 33, 34, 35, 36, 37, 38, 39 or 40 nucleotides. In some embodiments, each homing endonuclease recognition site consists of 24 nucleotides.

In some embodiments, ES1 is positioned 3' of DR1 and 5' of D. In some embodiments, ES1 is positioned to the 3' end of DR1. In some embodiments, ES1 is positioned immediately adjacent to the 3' end of DR1. In some embodiments, ES1 is positioned downstream to the 3' end of DR1. In some embodiments ES1 is positioned to the 5' end of D. In some embodiments, ES1 is positioned immediately adjacent to the 5' end of D. In some embodiments, ES1 is positioned upstream to the 5' end of D.

In some embodiments, ES1 is positioned 3' of D and 5' of DR2. In some embodiments, ES1 is positioned to the 3' end of D. In some embodiments, ES1 is positioned immediately adjacent to the 3' end of D. In some embodiments, ES1 is positioned downstream to the 3' end of D. In some embodiments, ES1 is positioned to the 5' end of DR2. In some embodiments, ES1 is positioned immediately adjacent to the 5' end of DR2. In some embodiments, ES2 is positioned upstream to the 5' end of DR2.

In some embodiments, ES2, when present in combination with ES1, is positioned 3' of D and 5' of DR2. In some embodiments, ES2 is positioned to the 3' end of D. In some embodiments, ES2 is positioned immediately adjacent to the 3' end of D. In some embodiments, ES2 is positioned downstream to the 3' end of D. In some embodiments, ES2 is positioned to the 5' end of DR2. In some embodiments, ES2 is positioned immediately adjacent to the 5' end of DR2. In some embodiments, ES2 is positioned upstream to the 5' end of DR2.

In some embodiments, where ES1 and ES2 are both present, ES1 and ES2 are arranged in the opposite orientation with respect to one another. In some embodiments, where ES1 and ES2 are both present, ES1 and ES2 are arranged in the same orientation with respect to one another.

In some embodiments, ES1 and ES2 are recognition sites for any homing endonuclease known to those of skill in the art. Homing endonucleases of many types (but not those from group II introns) catalyze a staggered double strand break (DSB) with a 4 bp single-stranded 3' overhang. In some embodiments, at least one of ES1 and ES2 is a recognition site for a homing endonuclease selected from the group consisting of: an LAGLIDADG (SEQ ID NO: 1) homing endonuclease, an HNH homing endonuclease, a His-Cys box homing endonuclease, a GIY-YIG (SEQ ID NO: 2) homing endonuclease, and a cyanobacterial homing endonuclease. In certain embodiments, each of ES1 and ES2 is a recognition site for a homing endonuclease selected from the group consisting of: an LAGLIDADG (SEQ ID NO: 1) homing endonuclease, an HNH homing endonuclease, a His-Cys box homing endonuclease, a GIY-YIG (SEQ ID NO: 2) homing endonuclease, and a cyanobacterial homing endonuclease. See, e.g., Stoddard, *Quarterly Review of Biophysics* 38(1): 49-95 (2006). These families differ greatly in their conserved nuclease active-site core motifs and catalytic mechanisms, biological and genomic distributions, and wider relationship to non-homing nuclease systems. Examples of useful specific homing endonucleases from these families include, but are not limited to: I-CreI (see, Rochaix et al., *Nucleic Acids Res.* 13: 975-984 (1985), I-MsoI (see, Lucas et al., *Nucleic Acids Res.* 29: 960-969 (2001), I-SceI (see, Foury et al., *FEBS Lett.* 440: 325-331 (1998), I-SceIV (see, Moran et al., *Nucleic Acids Res.* 20: 4069-4076 (1992), H-DreI (see, Chevalier et al., *Mol. Cell.* 10: 895-905 (2002), I-HmuI (see, Goodrich-Blair et al., *Cell* 63: 417-424 (1990); Goodrich-Blair et al., *Cell* 84: 211-221 (1996), I-PpoI (see, Muscarella et al., *Mol. Cell. Biol.* 10: 3386-3396 (1990), I-DirI (see, Johansen et al., *Cell* 76: 725-734 (1994); Johansen, *Nucleic Acids Res.* 21: 4405 (1993), I-NjaI (see, Elde et al., *Eur. J. Biochem.* 259: 281-288 (1999); De Jonckheere et al., *J. Eukaryot. Microbiol.* 41: 457-463 (1994), I-NanI (see, Elde et al., *S. Eur. J. Biochem.* 259: 281-288 (1999); De Jonckheere et al., *J. Eukaryot. Microbiol.* 41: 457-463 (1994)), I-NitI (see, De Jonckheere et al., *J. Eukaryot. Microbiol.* 41: 457-463 (1994); Elde et al., *Eur. J. Biochem.* 259: 281-288 (1999), I-TevI (see, Chu et al., *Cell* 45: 157-166 (1986), I-TevII (see, Tomaschewski et al., *Nucleic Acids Res.* 15: 3632-3633 (1987), I-TevIII (see, Eddy et al., *Genes Dev.* 5: 1032-1041 (1991), F-TevI (see, Fujisawa et al., *Nucleic Acids Res.* 13: 7473-7481 (1985), F-TevII (see, Kadyrov et al., *Dokl. Biochem.* 339: 145-147 (1994); Kaliman, *Nucleic Acids Res.* 18: 4277 (1990), F-CphI (see, Zeng et al., *Curr. Biol.* 19: 218-222 (2009), PI-MgaI (see, Saves et al., *Nucleic Acids Res.* 29:4310-4318 (2001), I-CsmI (see, Colleaux et al., *Mol. Gen. Genet.* 223:288-296 (1990), I-CeuI (see, Turmel et al., *J. Mol. Biol.* 218: 293-311 (1991) and PI-SceI (see, Hirata et al., *J. Biol. Chem.* 265: 6726-6733 (1990).

In some embodiments, at least one of ES1 or ES2 is a recognition site for a homing endonuclease selected from the group consisting of: I-CreI, I-MsoI, I-SceI, I-SceIV, H-DreI, I-HmuI, I-PpoI, I-DirI, I-NjaI, I-NanI, I-NitI, I-TevI, I-TevII, I-TevIII, F-TevI, F-TevII, F-CphI, PI-MgaI, I-CsmI, I-CeuI, and PI-SceI. In certain embodiments, each of ES1 and ES2 is a recognition site for a homing endonuclease selected from the group consisting of: I-CreI, I-MsoI, I-SceI, I-SceIV, H-DreI, I-HmuI, I-PpoI, I-DirI, I-NjaI, I-NanI, I-NitI, I-TevI, I-TevII, I-TevIII, F-TevI, F-TevII, F-CphI, PI-MgaI, I-CsmI, I-CeuI, and PI-SceI.

In particular embodiments of the compositions and methods provided herein, ES1 and ES2 are selected based on the absence of the homing endonuclease recognition site from the wild-type (unengineered) nuclear DNA of the host cell. For example, the recognition sites for I-SceI, PI-MtuII(pps1), PI-MgaI(pps1), and F-CphI are absent from wild-type (unengineered) *S. cerevisiae* nuclear DNA (see, e.g., *Curr Biol* 2009; 19:218-22; *Proc Natl Acad Sci USA* 1988; 85:6022-6; *J Biol Chem* 2002; 277:16257-64; *J Biol Chem* 2002; 277: 40352-61; and *Nucleic Acids Res* 2001; 29:4310-8), while the site for VDE aka PI-SceI is present in some strains and absent in others. (see, e.g., *Nucleic Acids Res* 2001; 29:4215-23). Thus, in some embodiments of the compositions and methods provided herein, ES1 and ES2 are recognition sites for I-SceI, and the host cell is a *S. cerevisiae* cell. In some embodiments, the ES1 and ES2 are recognition sites for PI-MtuII(pps1), and the host cell is a *S. cerevisiae* cell. In some embodiments, the ES1 and ES2 are recognition sites for PI-MgaI(pps1), and the host cell is a *S. cerevisiae* cell. In some embodiments, the ES1 and ES2 are recognition sites for F-CphI, and the host cell is a *S. cerevisiae* cell.

In some embodiments, the selection of ES1 and ES2 is based on fulfillment of one or more of the following criteria: (1) the homing endonuclease recognition site is absent from the entirety of the wild-type (unengineered) genome of the host cell (i.e., including mitochondrial DNA); (2) in the absence of the expression of the corresponding homing endonuclease, the recognition site of the homing endonuclease is not cleaved; and (3) nuclear expression of the corresponding homing endonuclease, e.g., to induce excision of a genomically integrated target nucleic acid, is not detrimental to the host cell. In some embodiments, in addition to being absent from the wild-type (unengineered) nuclear DNA of the host cell, ES1 and ES2 fulfill one, two, or all three of the criteria listed above.

5.2.2. Tandem Repeats

The excisable nucleic acid construct comprises a first and a second tandem repeat. The first tandem repeat (DR1) is located 5' of the target DNA segment (D) and the second tandem repeat (DR2) is located 3' of the target DNA segment (D).

The first and second tandem repeats can mediate the recombination of the remainder of the excisable nucleic acid construct following cleavage by homing endonucleases. Tandem repeats positioned in the same direction with respect to each other (direct tandem repeats) can advantageously mediate intrachromosomal recombination within a host cell, via the single stranded annealing pathway. See, e.g., Ivanov et al., *Genetics* 142:693-704 (1996).

DR1 and DR2 can be any tandem repeats that can mediate recombination of the remainder of the excisable nucleic acid construct following cleavage by homing endonucleases. Properties of tandem repeats that may affect such recombination include but are not limited to: length, GC content, homology with the native sequence of the host cell genome, and the degree of sequence identity between the tandem repeats. The extent of sequence identity may be determined using any computer program and associated parameters, including those described herein, such as BLAST 2.2.2 or FASTA version 3.0t78, with the default parameters.

In some embodiments, DR1 is positioned to the 5' end of ES1. In some embodiments, DR1 is positioned immediately adjacent to the 5' end of ES1. In some embodiments, DR1 is positioned upstream to the 5' end of ES1.

In some embodiments, DR2 is positioned to the 3' end of ES1, or when both ES1 and ES2 are present, to the 3' end of ES2. In some embodiments, DR2 is positioned immediately adjacent to the 3' end of ES1, or when both ES1 and ES2 are present, to the 3' end of ES2. In some embodiments, DR2 is positioned downstream to the 3' end of ES1, or when both ES1 and ES2 are present, to the 3' end of ES2.

In some embodiments, each of DR1 and DR2 consists of at least 18 nucleotides. In some embodiments, each of DR1 and DR2 consists of 18-80 nucleotides. In some embodiments, each of DR1 and DR2 consists of 18-75 nucleotides. In some embodiments, each of DR1 and DR2 consists of 18-70 nucleotides. In some embodiments, each of DR1 and DR2 consists of 18-65 nucleotides. In some embodiments, each of DR1 and DR2 consists of 18-60 nucleotides. In some embodiments, each of DR1 and DR2 consists of 18-55 nucleotides. In some embodiments, each of DR1 and DR2 consists of 18-50 nucleotides. In some embodiments, each of DR1 and DR2 consists of 18-45 nucleotides. In some embodiments, each of DR1 and DR2 consists of 18-40 nucleotides. In some embodiments, each of DR1 and DR2 consists of 18-35 nucleotides. In some embodiments, each of DR1 and DR2 consists of 19-30 nucleotides. In some embodiments, each of DR1 and DR2 consists of 18-25 nucleotides.

In some embodiments, each of DR1 and DR2 consists of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 nucleotides.

In some embodiments, DR1 and DR2 share at least 25% nucleotide sequence identity. In some embodiments, DR1 and DR2 share at least 30% nucleotide sequence identity. In some embodiments, DR1 and DR2 share at least 35% nucleotide sequence identity. In some embodiments, DR1 and DR2 share at least 40% nucleotide sequence identity. In some embodiments, DR1 and DR2 share at least 45% nucleotide sequence identity. In some embodiments, DR1 and DR2 share at least 50% nucleotide sequence identity. In some embodiments, DR1 and DR2 share at least 60% nucleotide sequence identity. In some embodiments, DR1 and DR2 share at least 65% nucleotide sequence identity. In some embodiments, DR1 and DR2 share at least 70% nucleotide sequence identity. In some embodiments, DR1 and DR2 share at least 75% nucleotide sequence identity. In some embodiments, DR1 and DR2 share at least 80% nucleotide sequence identity. In some embodiments, DR1 and DR2 share at least 85% nucleotide sequence identity. In some embodiments, DR1 and DR2 share at least 90% nucleotide sequence identity. In some embodiments, DR1 and DR2 share at least 95% nucleotide sequence identity. In some embodiments, DR1 and DR2 share at least 99% nucleotide sequence identity. In some embodiments, DR1 and DR2 share 100% nucleotide sequence identity.

In preferred embodiments, DR1 and DR2 are positioned in the same orientation with respect to one another (i.e. they are direct tandem repeats).

5.2.3. Target DNA Segment

The excisable nucleic acid construct comprises a target DNA segment (D). In some embodiments, the target DNA segment (D) is positioned 3' of the first homing endonuclease recognition site (ES1). In some embodiments, where a second homing endonuclease recognition site (ES2) is present, the target DNA segment (D) is positioned 5' of ES2. In some embodiments, the target DNA segment (D) is positioned 3' of the first homing endonuclease recognition site (ES1) and 5' of the second tandem repeat (DR2). In some embodiments, the target DNA segment (D) is positioned 3' of the first tandem repeat (DR1) and 5' of the first homing endonuclease recognition site (ES1).

In some embodiments, the 5' end of D is positioned to the 3' end of ES1. In some embodiments, the 5' end of D is positioned immediately adjacent to the 3' end of ES1. In some embodiments, the 5' end of D is positioned downstream to the 3' end of ES1.

In some embodiments, the 5' end of D is positioned to the 3' end of DR1. In some embodiments, the 5' end of D is positioned immediately adjacent to the 3' end of DR1. In some embodiments, the 5' end of D is positioned downstream to the 3' end of DR1.

In some embodiments, when ES1 is present in combination with ES2, the 3' end of D is positioned to the 5' end of ES2. In some embodiments, when ES1 is present in combination with ES2, the 3' end of D is positioned immediately adjacent to the 5' end of ES2. In some embodiments, when ES1 is present in combination with ES2, the 3' end of D is positioned upstream to the 5' end of ES2.

In some embodiments, the 3' end of D is positioned to the 5' end of DR2. In some embodiments, the 3' end of D is positioned immediately adjacent to the 5' end of DR2. In some embodiments, the 3' end of D is positioned upstream to the 5' end of DR2.

The target DNA segment can be any target DNA segment deemed useful by one of skill in the art. For example, the target DNA segment may comprise a gene of interest that can be "knocked in" a host genome and subsequently "knocked out" by excision. In some embodiments, the target nucleic can comprise a selectable marker that may be used to select for the integration of the excisable nucleic acid construct into a host genome and that is subsequently removed from the host genome by excision.

Useful examples of a target DNA segment include but are not limited to: a protein-coding sequence, selectable marker, reporter gene, fluorescent marker coding sequence, promoter, enhancer, terminator, transcriptional activator, transcriptional repressor, transcriptional activator binding site, transcriptional repressor binding site, intron, exon, poly-A tail, multiple cloning site, nuclear localization signal, mRNA stabilization signal, integration loci, epitope tag coding sequence, degradation signal, or any other naturally occurring or synthetic DNA molecule. In some embodiments, the DNA segment can be of natural origin. Alternatively, a target DNA segment can be completely of synthetic origin, produced in vitro. Furthermore, a target DNA segment can comprise any combination of isolated naturally occurring DNA molecules, or any combination of an isolated naturally occurring DNA molecule and a synthetic DNA molecule. For example, a target DNA segment may comprise a heterologous promoter operably linked to a protein coding sequence, a protein coding sequence linked to a poly-A tail, a protein coding sequence linked in-frame with a epitope tag coding sequence, and the like. The target DNA segment may be obtained by standard procedures known in the art from cloned DNA (e.g., a DNA "library"), by chemical synthesis, by cDNA cloning, or by the cloning of genomic DNA, or fragments thereof, purified from the desired cell, or by PCR amplification and cloning. See, for example, Sambrook et al., *Molecular Cloning, A Laboratory Manual*, 3d. ed., Cold Spring Harbor Laboratory Press, Cold Spring Harbor, N.Y. (2001); Glover, D. M. (ed.), *DNA Cloning: A Practical Approach*, 2d. ed., MRL Press, Ltd., Oxford, U.K. (1995).

In some embodiments, D comprises a promoter element operably linked to a nucleic acid encoding a homing endonuclease. For example, where the excisable nucleic acid construct comprises a first and second recognition site, e.g., for the homing endonuclease F-CphI, the target DNA segment can include a nucleic acid sequence encoding F-CphI, which nucleic acid sequence is operably linked to a promoter element. In particular embodiments, the promoter element which controls the expression of the nucleic acid encoding the homing endonuclease is an inducible promoter, e.g., a galactose inducible promoter of *Saccharomyces cerevisiae* (e.g., promoters of the GAL1, GAL7, and GAL10 genes), such that excision of the target DNA segment, including the sequence encoding the homing endonuclease, can be selectively excised, for example, after integration of the excisable nucleic acid construct into the host cell genome. In some embodiments, the homing endonuclease is selected from the group consisting of: an LAGLIDADG (SEQ ID NO: 1) homing endonuclease, an HNH homing endonuclease, a His-Cys box homing endonuclease, a GIY-YIG (SEQ ID NO: 2) homing endonuclease, and a cyanobacterial homing endonuclease. In certain embodiments, the homing endonuclease is selected from the group consisting of: I-CreI, I-MsoI, I-SceI, I-SceIV, H-DreI, I-HmuI, I-PpoI, I-DirI, I-NjaI, I-NanI, I-NitI, I-NgrI, I-TevI, I-TevII, I-TevIII, F-TevI, F-TevII, F-CphI, PI-MgaI, PI-MtuII, I-CsmI, I-PanI, I-CeuI, and PI-SceI. In particular embodiments, the homing endonuclease is I-SceI. In certain embodiments, the homing endonuclease is F-CphI.

In some embodiments, D encodes one or more selectable markers. In some embodiments, the selectable marker is an antibiotic resistance marker. Antibiotic resistance markers are common to most plasmid vectors used for creating recombinant nucleic acid sequences. For instance, pBR and pUC-derived plasmids contain as a selectable marker the bacterial drug resistance marker AMP$^r$ or BLA gene (See, Sutcliffe, J. G., et al., *Proc. Natl. Acad. Sci. U.S.A.* 75:3737 (1978)). The BLA gene encodes the enzyme Tem-1, which functions as a beta-lactamase and is responsible for bacterial resistance to beta-lactam antibiotics, such as narrow-spectrum cephalosporins, cephamycins, and carbapenems (ertapenem), cefamandole, and cefoperazone, and all the anti-gram-negative-bacterium penicillins except temocillin.

Other useful selectable markers include but are not limited to: NAT1, PAT, AUR1-C, PDR4, SMR1, CAT, mouse dhfr, HPH, DSDA, KAN$^R$, and SH BLE genes. The NAT1 gene of *S. noursei* encodes nourseothricin N-acetyltransferase and confers resistance to nourseothricin. The PAT gene from *S. viridochromogenes* Tu94 encodes phosphinothricin N-acetyltransferase and confers resistance to bialophos. The AUR1-C gene from *S. cerevisiae* confers resistance to Auerobasidin A (AbA), an antifuncal antibiotic produced by *Auerobasidium pullulans* that is toxic to budding yeast *S. cerevisiae*. The PDR4 gene confers resistance to cerulenin. The SMR1 gene confers resistance to sulfometuron methyl. The CAT coding sequence from Tn9 transposon confers resistance to chloramphenicol. The mouse dhfr gene confers resistance to methotrexate. The HPH gene of *Klebsiella pneumonia* encodes hygromycin B phosphotransferase and confers resistance to Hygromycin B. The DSDA gene of *E. coli* encodes D-serine deaminase and allows yeast to grow on plates with D-serine as the sole nitrogen source. The KAN$^R$ gene of the Tn903 transposon encodes aminoglycoside phosphotransferase and confers resistance to G418. The SH BLE gene from *Streptoalloteichus hindustanus* encodes a Zeocin binding protein and confers resistance to Zeocin (bleomycin).

In other embodiments, the selectable marker comprises a yeast gene that permits for selection of transformed cells of a yeast host strain. In some embodiments, the selectable marker rescues an auxotrophy, for example a nutritional auxotrophy, in the host strain. In such embodiments, the host strain comprises a functional disruption in one or more genes of the amino acid biosynthetic pathways of the host that cause an auxotrophic phenotype, such as, for example, HIS3, LEU2, LYS1, MET15, and TRP1, or a functional disruption in one or more genes of the nucleotide biosynthetic pathways of the host that cause an auxotrophic phenotype, such as, for example, ADE2 and URA3. In particular embodiments, the genetically modified yeast host strain comprises a functional disruption in the URA3 gene. The functional disruption in the host yeast that causes an auxotrophic phenotype can be a point mutation, a partial or complete gene deletion, or an addition or substitution of nucleotides. Functional disruptions within the amino acid or nucleotide biosynthetic pathways cause the host strains to become auxotrophic mutants which, in contrast to the prototrophic wild-type strains, are incapable of optimum growth in media without supplementation with one or more nutrients. The functionally disrupted biosynthesis genes in the host strain can then serve as auxotrophic gene markers which can later be rescued, for example, upon introducing one or more plasmids comprising a functional copy of the disrupted biosynthesis gene.

Utilization of the URA3, TRP1, and LYS2 yeast genes as selectable markers has a marked advantage because both positive and negative selections are possible. Positive selection is carried out by auxotrophic complementation of the URA3, TRP1, and LYS2 mutations whereas negative selection is based on the specific inhibitors 5-fluoro-orotic acid (FOA), 5-fluoroanthranilic acid, and a-aminoadipic acid (aAA), respectively, that prevent growth of the prototrophic strains but allow growth of the URA3, TRP1, and LYS2 mutants, respectively. The URA3 gene encodes orotidine-5' phosphate decarboxylase, an enzyme that is required for the biosynthesis of uracil. Ura3– (or ura5–) cells can be selected on media containing FOA, which kills all URA3+ cells but not ura3– cells because FOA appears to be converted to the toxic compound 5-fluorouracil by the action of decarboxylase. The negative selection on FOA media is highly discriminating, and usually less than $10^{-2}$ FOA-resistant colonies are Ura+. The FOA selection procedure can be used to produce ura3 markers in haploid strains by mutation, and, more importantly, for selecting those cells that do not have the URA3-containing plasmids. The TRP1 gene encodes a phosphoribosylanthranilate isomerase that catalyzes the third step in tryptophan biosynthesis. Counterselection using 5-fluoroanthranilic acid involves antimetabolism by the strains that lack enzymes required for the conversion of anthranilic acid to tryptophan and thus are resistant to 5-fluoroanthranilic acid. The LYS2 gene encodes an aminoadipate reductase, an enzyme that is required for the biosynthesis of lysine. Lys2- and lys5-mutants, but not normal strains, grow on a medium lacking the normal nitrogen source but containing lysine and aAA. Apparently, lys2 and lys5 mutations cause the accumulation of a toxic intermediate of lysine biosynthesis that is formed by high levels of aAA, but these mutants still can use aAA as a nitrogen source. Similar with the FOA selection procedure, LYS2-containing plasmids can be conveniently expelled from lys2 hosts.

In other embodiments, the selectable marker is a marker other than one which rescues an auxotophic mutation. For example, the yeast host cell strain can comprise mutations other than auxotrophic mutations, for example, mutations that are not lethal to the host and that also do not cause adverse effects on the intended use of the strain, e.g., industrial fermentation, so long as the mutations can be identified by a known selection method.

5.2.4. Genomic Integration Sequences

In some embodiments, the excisable nucleic acid construct comprises a first and second genomic integration sequence. The genomic integration sites allows for the excisable nucleic acid constructs described herein to be integrated into the genome of the host cell, e.g., by host cell mediated homologous recombination. To integrate an excisable nucleic acid construct into the genome by homologous recombination, the excisable nucleic acid construct preferably comprises at one terminus a nucleic acid sequence comprising an upstream genomic integration sequence (IS1) and at the other terminus a nucleic acid sequence comprising a downstream genomic integration sequence (IS2), wherein each genomic integration sequence is of sufficient length to initiate homologous recombination by the host cell with its chromosome. In some embodiments, the first genomic integration sequence (IS1) is located 5' of the first tandem repeat (DR1) and the second genomic integration sequence (IS2) is located 3' of the second tandem repeat (DR2).

In certain embodiments, IS1 is positioned to the 5' of DR1. In some embodiments, IS1 is positioned immediately adjacent to the 5' of DR1. In some embodiments, IS1 is positioned upstream to the 5' of DR1.

In certain embodiments, IS2 is positioned to the 3' of DR2. In some embodiments, IS2 is positioned immediately adjacent to the 3' of DR2. In some embodiments, IS2 is positioned downstream to the 3' of DR2.

The first and second integration sequence allow for the excisable nucleic acid construct to integrate via homologous recombination into a particular locus of a host cell genome. Targeted integration of the excisable nucleic acid construct into a host cell genome may provide useful advantages. For example, the excisable nucleic acid construct may be integrated into a gene of interest in the host cell genome, thereby "knocking out" the gene of interest and rendering it non-functional (FIG. 2). Alternatively, targeted integration of the excisable nucleic acid construct may be useful in "knocking in" a gene of interest at a particular genomic locus or in "knocking in" regulatory elements near a gene of interest, for example, to activate or up-regulate the expression of a gene of interest.

Properties that may affect the integration of an excisable nucleic acid construct at a particular genomic locus include but are not limited to: the lengths of the genomic integration sequences, the overall length of the excisable nucleic acid construct, and the nucleotide sequence or location of the genomic integration locus. For instance, effective heteroduplex formation between one strand of a genomic integration sequence and one strand of a particular locus in a host cell genome may depend on the length of the genomic integration sequence. An effective range for the length of a genomic integration sequence is 50 to 5,000 nucleotides. For a discussion of effective lengths of homology between genomic integration sequences and genomic loci see Hasty et al., *Mol Cell Biol* 11:5586-91 (1991).

IS1 and IS2 can comprise any nucleotide sequence of sufficient length and sequence identity to a host cell genomic locus that allows for genomic integration of the excisable nucleic acid construct. In certain embodiments, each of IS1 and IS2 comprises nucleotide sequences of sufficient length and sequence identity to a prokaryotic genomic locus to allow the integration of the excisable nucleic acid construct into the prokaryotic genomic locus. In certain embodiments, each of IS1 and IS2 comprises nucleotide sequences of sufficient length and sequence identity to a eukaryotic genomic locus to allow the integration of the excisable nucleic acid construct into the eukaryotic genomic locus. In certain embodiments, each of IS1 and IS2 comprises nucleotide sequences of sufficient length and sequence identity to a yeast genomic locus to allow the integration of the excisable nucleic acid construct into the yeast genomic locus. In certain embodiments, each of IS1 and IS2 comprises nucleotide sequences of sufficient length and sequence identity to a *Saccharomyces cerevisiae* genomic locus to allow the integration of the excisable nucleic acid construct into the *Saccharomyces cerevisiae* genomic locus. Suitable *Saccharomyces cerevisiae* genomic loci for integration of an excisable nucleic acid construct include but are not limited to the NDT80, HO, GAL80, HTX3, GAL2, and GAL1-GAL10-GAL7 locus.

In certain embodiments, each of IS1 and IS2 consists of about 50 to 5,000 nucleotides. In certain embodiments, each of IS1 and IS2 consists of about 100 to 2,500 nucleotides. In certain embodiments, each of IS1 and IS2 consists of about 100 to 1,000 nucleotides. In certain embodiments, each of IS1 and IS2 consists of about 250 to 750 nucleotides. In certain embodiments, each of IS1 and IS2 consists of about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900 or 5,000 nucleotides. In some embodiments, each of IS1 and IS2 consists of about 500 nucleotides.

An excisable nucleic acid construct comprising a first and a second genomic integration sequence can be made using any technique apparent to one of skill in the art. In certain embodiments, an excisable nucleic acid construct comprising a first and a second integration sites is made using overlap extension PCR and molecular cloning techniques known in the art. See, e.g., U.S. Patent Application Publication No. 2010/0136633, U.S. Pat. No. 5,023,171 (splicing by overextension PCR); Sambrook et al., 2001, *Molecular Cloning—A Laboratory Manual*, 3$^{rd}$ edition, Cold Spring Harbor Laboratory, Cold Spring Harbor, N.Y.

5.3 Host Cells

In another aspect provided herein is a host cell comprising the excisable nucleic acid construct described above. In certain embodiments, the host cell comprises the excisable nucleic acid construct integrated into the host cell genome.

Suitable host cells include any cell in which an excision of a target DNA segment from a chromosomal or episomal locus is desired. In some embodiments, the host cell is a prokaryotic cell. In some embodiments, the host cell is a bacterial cell. In some embodiments, the host cell is an *Escherichia coli* cell. In some embodiments, the host cell is a eukaryotic cell. In some embodiments, the host cell is a mammalian cell. In some embodiments, the host cell is a Chinese hamster ovary (CHO) cell, a COS-7 cell, a mouse fibroblast cell, a mouse embryonal carcinoma cell, or a mouse embryonic stem cell. In some embodiments, the host cell is an insect cell. In some embodiments, the host cell is a S2 cell, a Schneider cell, a S12 cell, a 5B1-4 cell, a Tn5 cell, or a Sf9 cell. In some embodiments, the host cell is a unicellular eukaryotic organism cell.

In some embodiments, the host cell is a yeast cell. In some embodiments, the host cell is a diploid yeast cell. In some embodiments, the host cell is a haploid yeast cell. Useful yeast host cells include yeast cells that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis,* and *Zygozyma,* among others.

In some embodiments, the yeast host cell is a *Saccharomyces cerevisiae* cell, a *Pichia pastoris* cell, a *Schizosaccharomyces pombe* cell, a *Dekkera bruxellensis* cell, a *Kluyveromyces lactis* cell, a *Arxula adeninivorans* cell, or a *Hansenula polymorpha* (now known as *Pichia angusta*) cell. In a particular embodiment, the yeast host cell is a *Saccharomyces cerevisiae* cell. In some embodiments, the yeast host cell is a Saccharomyces fragilis cell or a *Kluyveromyces lactis* (previously called *Saccharomyces lactis*) cell. In some embodiments, the yeast host cell is a cell belonging to the genus *Candida*, such as *Candida lipolytica, Candida guilliermondii, Candida krusei, Candida pseudotropicalis*, or *Candida utilis*. In another particular embodiment, the yeast host cell is a *Kluveromyces marxianus* cell.

In particular embodiments, the yeast host cell is a *Saccharomyces cerevisiae* cell selected from the group consisting of a Baker's yeast cell, a CBS 7959 cell, a CBS 7960 cell, a CBS 7961 cell, a CBS 7962 cell, a CBS 7963 cell, a CBS 7964 cell, a IZ-1904 cell, a TA cell, a BG-1 cell, a CR-1 cell, a SA-1 cell, a M-26 cell, a Y-904 cell, a PE-2 cell, a PE-5 cell, a VR-1 cell, a BR-1 cell, a BR-2 cell, a ME-2 cell, a VR-2 cell, a MA-3 cell, a MA-4 cell, a CAT-1 cell, a CB-1 cell, a NR-1 cell, a BT-1 cell, and a AL-1 cell. In some embodiments, the host cell is a *Saccharomyces cerevisiae* cell selected from the group consisting of a PE-2 cell, a CAT-1 cell, a VR-1 cell, a BG-1 cell, a CR-1 cell, and a SA-1 cell. In a particular embodiment, the *Saccharomyces cerevisiae* host cell is a PE-2 cell. In another particular embodiment, the *Saccharomyces cerevisiae* host cell is a CAT-1 cell. In another particular embodiment, the *Saccharomyces cerevisiae* host cell is a BG-1 cell.

In certain embodiments, an excisable nucleic acid construct as described above may be introduced into a host cell using any conventional technique to introduce exogenous nucleic acids into a cell known in the art. Such methods include, but are not limited to, direct uptake of the molecule by a cell from solution, or facilitated uptake through lipofection using, e.g., liposomes or immunoliposomes; particle-mediated transfection; etc. See, e.g., U.S. Pat. No. 5,272,065; Goeddel et al., eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY. Particular methods for transforming yeast cells are well known in the art. See Hinnen et al., Proc. Natl. Acad. Sci. USA 75:1292-3 (1978); Cregg et al., Mol. Cell. Biol. 5:3376-3385 (1985). Exemplary techniques include but are not limited to, spheroplasting, electroporation, PEG 1000 mediated transformation, and lithium acetate or lithium chloride mediated transformation.

5.4 Homing Endonuclease Expression Vector

In another aspect provided herein is an expression vector encoding a homing endonuclease useful in excising a target DNA segment from the genome of a host cell comprising an excisable nucleic acid construct.

In certain embodiments, the expression vector encodes a homing endonuclease selected from the group consisting of: an LAGLIDADG (SEQ ID NO: 1) homing endonuclease, an HNH homing endonuclease, a His-Cys box homing endonuclease, a GIY-YIG (SEQ ID NO: 2) homing endonuclease, and a cyanobacterial homing endonuclease. In certain embodiments, the expression vector encodes a homing endonuclease selected from the group consisting of: I-CreI, I-MsoI, I-SceI, I-SceIV, H-DreI, I-HmuI, I-PpoI, I-DirI, I-NjaI, I-NanI, I-NitI, I-NgrI, I-TevI, I-TevII, I-TevIII, F-TevI, F-TevII, F-CphI, PI-MgaI, PI-MtuII, I-CsmI, I-PanI, I-CeuI, and PI-SceI. In particular embodiments, the expression vector encodes I-SceI. In certain embodiments, the expression vector encodes F-CphI.

The homing endonuclease expression vector is any expression vector that allows for the expression of a homing endonuclease within a host cell. Suitable expression vectors include but are not limited to those known for use in expressing genes in *Escherichia coli*, yeast, or mammalian cells. Examples of *Escherichia coli* expression vectors include but are not limited to pSCM525, pDIC73, pSCM351, and pSCM353. Examples of yeast expression vectors include but are not limited to pPEX7 and pPEX408. Other examples of suitable expression vectors include the yeast-*Escherichia coli* pRS series of shuttle vectors comprising CEN.ARS sequences and yeast selectable markers; and 2µ plasmids.

In certain embodiments, the homing endonuclease expression vector further comprises a selectable marker that allows for selection of host cells comprising the expression vector. In certain embodiments, the selectable marker is selected from the group consisting of: URA3, hygromycin B phosphotransferase, aminoglycoside phosphotransferase, zeocin resistance, and phosphinothricin N-acetyltransferase.

In certain embodiments, the expression vector further comprises a transcription termination sequence and a promoter operatively linked to the nucleotide sequence encoding the homing endonuclease. In some embodiments, the promoter is a constitutive promoter. In some embodiments, the promoter is an inducible promoter.

Illustrative examples of promoters suitable for use in yeast cells include, but are not limited to the promoter of the TEF1 gene of *K. lactis*, the promoter of the PGK1 gene of *Saccharomyces cerevisiae*, the promoter of the TDH3 gene of *Saccharomyces cerevisiae*, repressible promoters, e.g., the promoter of the CTR3 gene of *Saccharomyces cerevisiae*, and inducible promoters, e.g., galactose inducible promoters of *Saccharomyces cerevisiae* (e.g., promoters of the GAL1, GAL7, and GAL10 genes).

In some embodiments, an additional nucleotide sequence comprising a nuclear localization sequence (NLS) is linked to the 5' of the nucleotide sequence encoding the homing endonuclease. The NLS can facilitate nuclear localization of larger homing endonucleases (>25 kD). In some embodiments, the nuclear localization sequence is an SV40 nuclear localization sequence. In some embodiments, the nuclear localization sequence is a yeast nuclear localization sequence.

A homing endonuclease expression vector can be made by any technique apparent to one skilled in the art. In certain embodiments, the vector is made using polymerase chain reaction (PCR) and molecular cloning techniques well known in the art. See, e.g., *PCR Technology: Principles and Applications for DNA Amplification*, ed. HA Erlich, Stockton Press, New York, N.Y. (1989); Sambrook et al., 2001, *Molecular Cloning—A Laboratory Manual*, 3$^{rd}$ edition, Cold Spring Harbor Laboratory, Cold Spring Harbor, N.Y.

5.5 Methods of Excising a Target DNA Segment

In another aspect provided herein are methods of excising a target DNA segment from the genome of a host cell comprising an excisable nucleic acid construct described above. In certain embodiments, the methods comprise contacting the excisable nucleic acid construct, e.g., a chromasomally integrated nucleic acid construct, with a homing endonuclease in a host cell such that the homing endonuclease cleaves at or adjacent to at least one homing endonuclease recognition site. In some embodiments, the homing endonuclease cleaves at or adjacent to each of the homing endonuclease recognition sites.

The excisable nucleic acid construct can be contacted with the homing endonuclease by any technique deemed suitable by one of skill in the art. In certain embodiments, a homing endonuclease is expressed within a host cell using a homing endonuclease expression vector. Any homing endonuclease expression vector may be used including the expression vectors described above. The homing endonuclease expression vector may comprise a selectable marker, e.g., a counter-selectable marker, that allows for selection of host cells that do not contain the expression vector subsequent to excision of the target DNA segment. The expression vector used may also be a transient vector that has no selection marker, or is one that is not selected for. In particular embodiments, the progeny of a host cell comprising a transient vector loses the vector over time. In other embodiments, the excisable nucleic acid construct can be contacted with a purified form of the homing endonuclease.

In some embodiments, cleavage of each of ES1 and ES2 advantageously creates three nucleic acid fragments (FIGS. 3A and 3B): (1) a left arm of a genomic nucleic acid; (2) a nucleic acid fragment comprising the target DNA segment; and (3) a right arm of the genomic nucleic acid. After cleavage, endogenous 5' to 3' exonucleases found in the host cell rapidly degrade one strand of each nucleic acid fragment, destroying the nucleic acid fragment comprising the target DNA segment and leaving long 3' tails on the left (4) and right (5) arms of the genomic nucleic acid (FIG. 3C) comprising DR1 and DR2 as complementary regions (FIG. 4A). The complementary regions form a heteroduplex (FIG. 4B, 6) and undergo recombination facilitated by host cell proteins. In some embodiments, the complementary regions advantageously undergo recombination via the single strand annealing pathway. The extreme 3' ends of the tails on the right (7) and left (8) arms are not complementary and thus hang out of the heteroduplex formed by the complementary portions. These extreme non-complementary 3' ends are advantageously cleaved by a flap nuclease. Finally, repair DNA synthesis and DNA ligase fill in the heteroduplex and seal nicks, creating an intact genomic nucleic acid with a precise excision of the target DNA segment (FIG. 4C). In embodiments in which DR1 and DR2 share 100% nucleotide sequence identity with one another, DR1 and DR1 advantageously recombine to create a genomic nucleic acid comprising a third tandem repeat that shares 100% nucleotide sequence identity with DR1 and DR2.

An advantage of the methods presented is that DR1 and DR2 of a particular excisable nucleic acid construct may comprise any tandem repeat that can mediate the recombination of the excisable nucleic acid construct upon cleavage. Therefore, multiple excisable nucleic acid constructs, each with unique tandem repeats, can be used within the same cell without concerns of genomic instabilities due to recombination of tandem repeats between different excisable nucleic acid constructs. Further, the methods can advantageously be used for removing selection markers to enable their reuse in the same host cell or its progeny.

In other embodiments, the excision event can be used to promote, suppress, or alter the expression of an endogenous gene of interest in the host cell. For example, in some embodiments, the first genomic integration sequence comprises a nucleotide sequence that is homologous to a nucleotide sequence positioned 5' of the coding sequence of the endogenous gene of interest, and the second genomic integration sequence comprises a nucleotide sequence that is homologous to a nucleotide sequence positioned within the coding sequence of the endogenous gene of interest, and the target DNA segment comprises a nucleotide sequence encoding a promoter that can be induced or repressed, for example, by addition of an inducer or repressor, respectively, to the culture medium in which the host cell is cultivated. Upon integration of the integrating sequence at the target locus, the native promoter of the target gene is replaced with the inducible or repressible promoter from the target DNA segment, rendering production of the gene product of the gene of interest dependent on the presence of the inducing or repressing agent in the culture medium. Similarly, the target DNA segment of the excisable nucleic acid construct may comprise a nucleotide sequence encoding a repressor that can be induced or repressed by addition of an inducer or repressor, respectively. Such exogenous regulation of the expression of the gene of interest can be removed as desired by inducing an excision event as described herein, such that the regulatable promoter or repressor is excised from the host cell genome.

In other embodiments, integration of the excisable nucleic acid construct into the host cell genome can be used to disrupt the expression of an endogenous gene of interest, for example, by interrupting the operable linkage between the coding sequence of the endogenous gene of interest and its native promoter element. Where restoration of the expression of the endogenous gene is desired, an excision event in accordance with the methods described herein can be induced to operably re-link the native promoter element with the coding sequence of the endogenous gene of interest, that is, to bring the native promoter element back within operable proximity of the coding sequence for the endogenous gene of interest.

5.6 Kits

In another aspect, provided herein is a kit for the excision of a target DNA segment from the genome of a host cell. In some embodiments, the kit comprises: (a) an excisable nucleic acid construct comprising, in a 5' to 3' orientation: (i) a first tandem repeat (DR1), (ii) a first homing endonuclease recognition site (ES1), (iii) a target DNA segment (D), and (iv) a second tandem repeat (DR2); and (b) a vector comprising a homing endonuclease nucleic acid encoding a homing endonuclease capable of binding to and cleaving at or adjacent to at least one of the first or second homing endonuclease recognition sites. In some embodiments, the kit comprises: (a) an excisable nucleic acid construct comprising, in a 5' to 3' orientation: (i) a first tandem repeat (DR1), (ii) a target DNA segment (D), (iii) a first homing endonuclease recognition site (ES1), and (iv) a second tandem repeat (DR2); and (b) a vector comprising a homing endonuclease nucleic acid encoding a homing endonuclease capable of binding to and cleaving at or adjacent to at least one of the first or second homing endonuclease recognition sites. In some embodiments, the kit comprises: (a) an excisable nucleic acid construct comprising, in a 5' to 3' orientation: (i) a first tandem repeat nucleic acid (DR1), (ii) a first homing endonuclease recognition site (ES1), (iii) a target nucleic acid, (iv) a second homing endonuclease recognition site (ES2), and (v) a second tandem repeat nucleic acid (DR2); and (b) a vector comprising a homing endonuclease nucleic acid encoding a homing endonuclease capable of binding to and cleaving at or adjacent to at least one of the first or second homing endonuclease recognition sites.

In some embodiments, each of the first and second tandem repeat nucleic acids independently comprises at least 18 nucleotide base pairs. In some embodiments, the excisable nucleic acid construct further comprises a first integration site linked 5' of the first homing endonuclease recognition site and a second integration site linked 3' of the second tandem repeat nucleic acid.

In a particular embodiment, the kit provided herein comprises: (a) an excisable nucleic acid construct comprising, in a 5' to 3' orientation: (i) a first tandem repeat nucleic acid of at least 18 nucleotide base pairs, (ii) a first I-SceI site, (iii) a target nucleic acid, (iv) a second I-SceI site, and (v) a second tandem repeat nucleic acid of at least 18 nucleotide base pairs; and (b) a vector comprising a nucleic acid encoding I-SceI. In some embodiments, the excisable nucleic acid construct further comprises a first integration site linked 5' of the first homing endonuclease recognition site and a second integration site linked 3' of the second tandem repeat nucleic acid.

In another particular embodiment, the kit provided herein comprises: (a) an excisable nucleic acid construct comprising, in a 5' to 3' orientation: (i) a first tandem repeat nucleic acid, (ii) a first F-CphI site, (iii) a target nucleic acid, (iv) a second F-CphI site, and (v) a second tandem repeat nucleic acid; and (b) a vector comprising a nucleic acid encoding F-CphI. In some embodiments, the excisable nucleic acid construct further comprises a first integration site linked 5' of the first homing endonuclease recognition site and a second integration site linked 3' of the second tandem repeat nucleic acid.

In some embodiments, the kit further comprises instructions for use that describe the methods of excising a target DNA segment from the genome of a host cell disclosed herein. In some embodiments, the kit comprises an excisable nucleic acid construct comprising a target DNA segment, wherein the target DNA segment is selected from, e.g., a protein-coding sequence, reporter gene, fluorescent marker coding sequence, promoter, enhancer, terminator, intron, exon, poly-A tail, multiple cloning site, nuclear localization signal, mRNA stabilization signal, selectable marker, integration loci, epitope tag coding sequence, or degradation signal.

6. EXAMPLES

6.1 Example 1

Construction of xMarker Constructs

The compositions and methods described herein were implemented to prepare and characterize a series of excisable selection markers for use in S. cerevisiae, described herein as "xMarkers," which tested the parameters of the DNA construct shown in FIG. 1. The xMarkers demonstrated the usefulness and extensibility to the endonucleases listed in Table 1 below.

With respect to the reagents used in the experiments described below, restriction enzymes were obtained from New England Biolabs and Fermentas. Phusion, a high-fidelity thermostable polymerase from Finnzymes, was used for construction of DNA used in cloning of plasmids or in yeast transformations for chromosomal integrations. A low-fidelity thermostable polymerase kit was used for PCR of genomic DNA from yeast colonies (Qiagen Taq PCR kit). Oligonucleotides were obtained from Integrated DNA Technologies (IDT). Other chemicals were obtained from Sigma, Fisher, and Zymo Research (e.g., standard molecular biology buffer components like Tris and EDTA and standard yeast reagents like lithium acetate and yeast nitrogen base). Competent E. coli cells used for DNA cloning were purchased from Invitrogen. DNA minipreps were performed with the miniprep kit from Qiagen. Molecular biology, yeast molecular genetics, and yeast cell culture techniques were performed according to standard protocols.

6.1.1. Construction of First Generation xMarkers

The initial series of xMarkers used URA3 as the selectable marker, and each member of the series differed in the number of I-SceI cleavage sites (1 or 2) and in the length of direct repeats (20, 40, 60, or 80 bp). URA3 is a counterselectable marker whose presence can be selected by growth on medium lacking uracil and whose absence can be selected by growth on medium containing 5-fluoroorotic acid. Direct repeat sequences were designed to consist of a 112 bp stretch of DNA, wherein each segment of 20 bp had a GC content of ~50%, and that stretches of 20, 40, 60, and 80 bp had little predicted secondary structure at temperatures above 30° C. The I-SceI cleavage sites all shared the same 18 bp sequence: 5'-TAGGGATAACAGGGTAAT-3' (SEQ ID NO: 3). Table 2 lists all tested first generation xMarkers with the number of cleavage sites and their orientation relative to each other, the length and sequence of the direct repeats (DR), and the sequence of the I-SceI cleavage site(s). For the xMarkers with two I-SceI sites, the sequence of elements was DR→/I-SceI site→/URA3/I-SceI site→/DR→. For the xMarker with one I-SceI site, the sequence of elements was DR→/I-SceI site→/URA3/DR→.

TABLE 1

Recognition and cleavage sites for the endonucleases.

| Meganuclease | minimal site size (base pairs) | site size used (base pairs) | sequence of site used |
|---|---|---|---|
| I-SceI | 18 | 18 | TAGGGATAACAGGGTAAT (SEQ ID NO: 3) |
| VDE) (PI-SceI) | 31 | 31 | TATGTCGGGTGCGGAGAAAGAGGTAATGAAA (SEQ ID NO: 4) |
| F-Cph | 20 | 24 | GATGCACGAGCGCAACGCTCACAA (SEQ ID NO: 5) |
| PI-MgaI (pps1) | 22 | 24 | GCGTAGCTGCCCAGTATGAGTCAG (SEQ ID NO: 6) |
| PI-MtuII (pps1) | unknown | 40 | ACGTGCACTACGTAGAGGGTCGCACCGCACC GATCTACAA (SEQ ID NO: 7) |

TABLE 2

List of characteristics of individual elements in first generation I-SceI xMarkers, with order and orientation of the elements as shown in FIG. 1

| name of URA3 xMarker | length of DR (bp) | I-SceI sites (#) | orientation of I-SceI sites to each other | DR (scar) sequence |
|---|---|---|---|---|
| 20mer-direct | 20 | 2 | direct | AAGATCCGATCGACCGAGAA (SEQ ID NO: 8) |
| 40mer-direct | 40 | 2 | direct | AAGATCCGATCGACCGAGAACTGAGAA CGGTGCAATGATC (SEQ ID NO: 9) |
| 60mer-direct (aka s0x-URA3) | 60 | 2 | direct | AAGATCCGATCGACCGAGAACTGAGAA CGGTGCAATGATC-AACATGATCTGCGACGAGCT (SEQ ID NO: 10) |
| 80mer-direct | 80 | 2 | direct | AAGATCCGATCGACCGAGAACTGAGAA CGGTGCAATGATC-AACATGATCTGCGACGAGCTTGAGGAT GCAAATGGCTGAC (SEQ ID NO: 11) |
| 60mer-single | 60 | 1 | solo | AAGATCCGATCGACCGAGAACTGAGAA CGGTGCAATGATC-AACATGATCTGCGACGAGCT (SEQ ID NO: 12) |

Due to the repeated sites in the xMarkers, construction required that the left half and the right half be constructed separately before joining the two halves. The first generation xMarkers were created in three steps.

First, the sequences flanking the selection marker on the left (5') and on the right (3') were constructed separately by annealing of phosphorylated oligonucleotides. The left and right double-stranded flanking sequences created by annealing were designed to have complementary, non-palindromic, 3' single-stranded overhangs of five bases (TAGAC on top and GTCTA on bottom). Table 3 lists the oligos used for each xMarker. For each annealing reaction, an equimolar mixture of oligonucleotides in DNA ligase buffer was heated to 95° C. in a heat block for 5 minutes and then the heat block was turned off and allowed to cool slowly to room temperature over the course of 1-2 hours.

TABLE 3

List of oligonucleotides mixed for annealing to make left segments and right segments flanking the marker in first generation I-SceI xMarkers.

| name of URA3 xMarker | oligos annealed for left segment | oligos annealed for right segment |
|---|---|---|
| 20mer-direct | KB411, KB412 | KB464, KB429 |
| 40mer-direct | KB415, KB416 | KB419, KB420 |
| 60mer-direct (aka s0x-URA3) | KB423, KB425, KB426, KB427, KB428 | KB419, KB423, KB424, KB429 |
| 80mer-direct | KB423, KB425, KBB427, KB431, KB432, KB433 | KB419, KB423, KB429, KB432, KB434 |
| 60mer-single | KB423, KB425, KB426, KB427, KB428 | KB421, KB423, KB424, KB430 |

Second, the corresponding left and right flanking DNAs from the annealing mixtures were mixed with the RYSE 12 entry vector for a 3-way ligation. The right end of the left repeat sequence was joined to the left end of the right repeat sequence by a sticky end ligation, and on the opposite ends the left and right repeat sequences were joined to the plasmid by blunt end ligations. The spacer between the I-SceI cleavage sites contained divergent SchI restriction sites, separated by an XbaI site. These plasmids were called xMarker entry vectors, because they did not yet have a marker, and they had only the flanking sequences to direct cleavage and repair.

Third, the URA3 selection marker was ligated into the xMarker entry vectors. The URA3 marker was amplified by PCR from a plasmid (RaBit 12-0-M-555) to give a blunt-ended marker. For the directly repeated dual I-SceI site xMarkers, the URA3 PCR used oligonucleotides KB439 and KB440; for the single I-SceI site xMarker, the oligonucleotides were KB439 and KB441. The xMarker entry vectors were digested with SchI to give a blunt-ended linear plasmid. Then the two fragments were ligated together using ligase standard conditions. This generated the xMarker structure shown in FIG. 1. Individual isolates of ligated plasmids were recovered and the desired plasmids were identified by DNA sequencing of the insert in the plasmid.

6.1.2. Construction of Second Generation xMarkers

The second generation of xMarkers were all created with 60 bp direct repeats to aid DNA repair and with two I-SceI cleavage sites in direct repeat. Each xMarker had a unique 60 bp sequence, which was chosen to be a semi-random sequence, as indicated below in Table 4.

TABLE 4

List of 2nd generation I-SceI xMarkers and their 60 by repeat sequences.

| name of xMarker | selection | sequence of 60 by repeat |
|---|---|---|
| s1x_hphA | hygromcycin B resistance (hph) | CGTTACGAAGCACACACTAGTTAGCGTCGAGACA CATAGCGACGCTAGAACTTGCGACTT (SEQ ID NO: 13) |
| s2x_hphA | hygromcycin B resistance (hph) | GTACTGCCTAGTAGAAACGGATCTCCACGTACTA GAGTCCACCTGGTATCTATTAGCCCG (SEQ ID NO: 14) |
| s3x_kanA | kanamycin/G418 resistance (kan) | CGAGGATTAACGTGTAAGGCCCTAAGCTATGTAC CGCATCTCCTAAGAGAGTGTGACCCA (SEQ ID NO: 15) |
| s4x_kanA | kanamycin/G418 resistance (kan) | TTAATCAGCGCCCAGAGACTAGCACTGAATGATC AACGGGTAGTTCACACACTGCCAGAC (SEQ ID NO: 16) |
| s5x_natA | nourseothricin resistance (nat) | ATGGAATCACGGGGCTATTCCACTTGCTAATAAC GAGGCGCTTATCAACGGCGAGCACAT (SEQ ID NO: 17) |
| s6x_natA | nourseothricin resistance (nat) | AGTCAAAGCGCGATTCGCTAGGAATGAGAGCGA GAACGAACCGGAGTATATCACAATCGC (SEQ ID NO: 18) |
| s7x_URA3 | uracil prototropy (URA3) | ACTAGAGCGAAATGGAGAGGTACGTGATCCTACT AGAGCCCACGCTATCATACAGTTGGC (SEQ ID NO: 19) |
| s8x_URA3 | uracil prototropy (URA3) | GTACGTCCGTACTTATGCTGAGCGCTCCTACACG AAAAACTCACCGTGACTAGCATAACG (SEQ ID NO: 20) |

The 60 bp sequences were chosen to satisfy two criteria: (1) the first, second, and third 20 bp windows had a melting temperature of 60°±2° C. and (2) no sequence window 13 bp or longer that appeared in the 60 bp sequence was identical to any native sequence in the yeast genome. This set included four different selection markers: URA3; hygromycin B phosphotransferase or hph; nourseothricin acetyltransferase or nat; and aminoglycoside phosphotransferase or kan. These three drug resistance genes from bacteria were all controlled by adjacent sequences corresponding to the promoter and terminator of the TEF1 gene from *Kluyveromyces* lactic, and the suffix "A" was appended to indicate this TEF1-derived regulatory control; the cassettes were then called hphA, natA, and kanA.

Due to the repeated sites in the xMarkers, construction required that the left half and the right half be constructed separately before joining the two halves. The second generation xMarkers were created in two steps, using a strategy different from the first generation. The 60 bp sequence and a 20 bp I-SceI cleavage site were introduced to the left and right of the marker by priming PCR amplification of the marker with long-tailed oligonucleotides listed in Table 5 below.

TABLE 5

List of primers used for PCR amplification of left and right portions of 2nd generation I-SceI xMarkers.

| name of xMarker | left portion primers | right portion primers | restriction enzyme | alternative left portion primers | alternative right portion primers | alternative restriction enzyme |
|---|---|---|---|---|---|---|
| s1x_hphA | KB469, KB467 | KB470, KB468 | NdeI | KB469, KB492 | KB470, KB491 | RsrII or BanI |
| s2x_hphA | KB471, KB467 | KB472, KB468 | NdeI | KB471, KB492 | KB472, KB491 | RsrII or BanI |
| s3x_kanA | KB475, KB473 | KB476, KB474 | PvuI | KB475, KB494 | KB476, KB493 | NciI or BstXI |
| s4x_kanA | KB477, KB473 | KB478, KB474 | PvuI | KB477, KB494 | KB478, KB493 | NciI or BstXI |
| s5x_natA | KB481, KB479 | KB482, KB480 | StyI | none | none | none |
| s6x_natA | KB483, KB479 | KB484, KB480 | StyI | none | none | none |
| s7x_URA3 | KB487, KB485 | KB488, KB486 | NcoI | KB487, KB496 | KB488, KB495 | BsiHKAI or AlwNI |
| s8x_URA3 | KB489, KB485 | KB490, KB486 | NcoI | KB489, KB496 | KB490, KB495 | BsiHKAI or AlwNI |

The oligonucleotides contained a priming region of 20-22 bp at the 3' end and a 5' tail of 80 bp containing the unique 60 bp sequence and the I-SceI site. Two slightly different I-SceI sites were used on the left and the right of the marker: on the left, version 1 (v1) was 5'-GCTAGGGATAACAGGGTAAT-3'(SEQ ID NO: 21) and on the right, version 2 (v2) was 5'-ACTAGGGATAACAGGTTTAT-3' (SEQ ID NO: 22). The second generation xMarkers all had a structure of elements summarized by DR(60 bp)→/I-SceI site(v1)→/marker/I-SceI site(v2)→/DR (60 bp)→.

The xMarker construction overview is as follows. First, the left portion of the marker and the right portion of the marker were amplified separately by PCR. The primers were designed so that a middle segment of the marker was included in both the left and right PCR products, and so that this overlap segment included a unique restriction site that left single-stranded complementary overhangs. Second, the two PCR products were digested separately with the chosen restriction enzyme, gel-purified, and added to a three-piece ligation mixture with the linearized RYSE 12 entry vector. Similar to the first generation ligation, the left and right portions annealed and ligated using sticky ends, while the outermost ends of the marker construct participated in a blunt-ended ligation with the recipient plasmid. A difference from the first generation method is that after the ligation, the product already contains the marker gene and construction is completed. Individual isolates of ligated plasmids were recovered and the desired plasmids were identified by DNA sequencing of the insert in the plasmid. These plasmids were new xMarker 12 RaBits that could be used for RYSE-based stitching of compound DNA constructs, just as previous 12 RaBits were used.

The xMarker details are described below. The unique restriction sites internal to the markers that were used initially for each marker are as follows: hphA, NdeI (RsrII or BanI); kanA, PvuI (NciI or BstXI); natA, StyI; and URA3, NcoI (BsiHKAI or AlwNI). The enzymes chosen later were used if the initial enzymes did not yield positive clones; their benefit is that the single-stranded overhangs are not palindromic, so that it is not likely to get a ligated plasmid with two left or two right portions. Amplification of the left portion of a marker was performed with a ~20 bp reverse primer that annealed to the top strand on the right of the indicated restriction site and with a primer to the left edge of the marker that included a 5' tail, such that the 5' oligonucleotide had a structure as follows: 60 bp sequence→/I-SceI site (v1)→/~20 bp forward primer. Amplification of the right portion of a marker was performed with a ~20 bp forward primer that annealed to the bottom strand on the left of the indicated restriction site and with a primer to the right edge of the marker that included a 5' tail, such that the 3' oligonucleotide had a structure like this: 60 bp sequence(reverse complement)→/I-SceI site (v2, reverse complement)→/~20 bp reverse primer. Table 4 contains a list of the primers used for amplification of the left and right portions of each xMarker. The templates used for PCR amplification of the markers were RaBit plasmids: 12-0-M-21 for hphA, 12-0-M-261 for kanA, 12-0-M-262 for natA, and 12-0-M-555 for URA3. The finished xMarker second generation plasmids were themselves 12 RaBits that could be used for RYSE-based stitching of compound DNA constructs, just as previous 12 RaBits were used.

6.1.3. Construction of I-SceI Expression Plasmids

The I-SceI gene was placed under control of the *S. cerevisiae* promoter for GAL1 and cloned into a set of CEN.ARS plasmids with various markers. The yeast-*E. coli* shuttle vectors with CEN.ARS sequences and LEU2 (pRS415 aka pAM63) and URA3 (pRS416 aka pAM63) markers were previously described (see, e.g., Gene 1992; 110:119-22; and Genetics 1989; 122:19-27). Derivatives of pRS416 were made by replacing the auxotrophic markers with the drug resistance markers kanA (pAM1110), natA (pAM1111), and hphA (pAM1112). Each of the vectors was digested at a unique blunt-ended restriction site within the polylinker/multiple cloning site, either EcoRV (drug resistance markers) or SmaI (URA3 and LEU2), and then treated with phosphatase. The linearized vectors were ligated to a tripartite stitched PCR product that had been treated with polynucleotide kinase (PNK) to phosphorylate the 5' ends. The PCR product was made by stitching together three pieces of DNA having overlapping ends using the oligonucleotide primers called RYSE4 and RYSE11: (1) the promoter from *S. cerevisiae* GAL1 with RYSE linkers 2 and 3, provided by a Sap1-liberated insert from RaBit 23-0-P-39, (2) the I-SceI coding sequence with RYSE linkers 3 and 4, provided by a PCR product from a custom-synthesized gene used as template and primers 00177-JD-75AN and 00177-JD-75AO, and (3) the terminator from *S. cerevisiae* TDH with RYSE linkers 4 and 5, provided by a Sap1-liberated insert from RaBit 45-0-T-64. Individual isolates of ligated plasmids were recovered and the desired plasmids were identified by DNA sequencing of the $P_{GAL1}$-I-SceI-$T_{TDH3}$ insert in the plasmid. The expression plasmids were called pAM1592 (URA3), pAM1593 (kanA), pAM1594 (natA), and pAM1595 (hphA). The $P_{GAL1}$ promoter is highly expressed when cells are grown in galactose and, in wild-type cells (GAL80+GAL4), is not expressed when cells are grown in glucose. However, in mutants lacking the GAL80 repressor (gal80Δ), $P_{GAL1}$ is expressed even in the absence of galactose; glucose repression of $P_{GAL1}$ is further reduced by addition of a GAL4 mutant with a promoter mutation, called $GAL4_{OC}$ (for Operator Constitutive).

As described above, expression of the endonuclease was placed under the control of a strong promoter that was inducibly expressed in some host strain genetic backgrounds (GAL80+) and constitutively expressed in others (gal80Δ+/– $GAL4_{OC}$). Many other inducible promoters or constitutive promoters are expected to work well. Even if the promoter is constitutive, the expression of endonuclease can readily be eliminated after a desired time period by losing the plasmid; about half of the cells lose these plasmids after 10 generations in non-selective media (see, e.g., Gene 1992; 110:119-22; and Genetics 1989; 122:19-27).

6.1.4. Construction of Third Generation xMarkers: Additional Endonucleases

The initial series of xMarkers for other endonucleases (other than I-SceI) used URA3 as the selectable marker. Each member of the series of xMarkers contained a recognition/cleavage site for a different endonuclease [VDE, F-CphI, PI-MgaI (pps1), PI-MtuII (pps1)]. See Table 1 above for a description of the cleavage sites. All xURA3 markers contained two copies of the same 50 bp sequence in directly repeated orientation flanking the cleavage sites; this unique 50 bp sequence destined to be the scar after excision was called xM0. Table 6 below provides a description of the scar sequences.

TABLE 6

Scar sequences of 50 by used for 3rd generation xMarkers with endo-nucleases other than I-SceI

| Scar Sequence code | Enzyme | Marker | sequence |
|---|---|---|---|
| xM0 | F-CphI, PI-MgaI, PI-MgaII, VDE | URA3 | AAGATCCGATCGACCGAGAACTGAGAAC GGTGCAATGATCAACATGATCT (SEQ ID NO: 23) |
| xM1 | F-CphI | NatR | CGTTACGAAGCACACACTAGTTAGCGTC GAGACACATAGCGACGCTAGAA (SEQ ID NO: 24) |
| xM2 | F-CphI | HygR | GTACTGCCTAGTAGAAACGGATCTCCAC GTACTAGAGTCCACCTGGTATC (SEQ ID NO: 25) |
| xM3 | F-CphI | KanR | CGAGGATTAACGTGTAAGGCCCTAAGCT ATGTACCGCATCTCCTAAGAGA (SEQ ID NO: 26) |
| xM4 | F-CphI | NatR | TTAATCAGCGCCCAGAGACTAGCACTGA ATGATCAACGGGTAGTTCACAC (SEQ ID NO: 27) |
| xM5 | F-CphI | TBD | GAATCACGGGGCTATTCCACTTGCTAATA ACGAGGCGCTTATCAACGGCG (SEQ ID NO: 28) |
| xM6 | F-CphI | zeoR | GTCAAAGCGCGATTCGCTAGGAATGAGA GCGAGAACGAACCGGAGTATAT (SEQ ID NO: 29) |
| xM7 | F-CphI | TBD | ACTAGAGCGAAATGGAGAGGTACGTGAT CCTACTAGAGCCCACGCTATCA (SEQ ID NO: 30) |
| xM8 | F-CphI | TBD | GTACGTCCGTACTTATGCTGAGCGCTCCT ACACGAAAAACTCACCGTGAC (SEQ ID NO: 31) |
| xM9 | F-CphI | TBD | GCATTAAGTCGTAGCTAGCGGATTCTCTC TTCGTGCATCCTAGCAAATGG (SEQ ID NO: 32) |

The scar sequences were chosen to satisfy the following criteria: (1) GC content of ~50%, (2) the first and second sequence of 20 bp (within the 50 bp total) had a melting temperature of 60°±2° C., (3) minimal predicted secondary structure at temperatures above 30° C., and (4) no sequence window 13 bp or longer that appeared in the 50 bp sequence was identical to any native sequence in the yeast genome. The general sequence and orientation of elements in the xMarkers was as shown in FIG. 1: DR(50 bp)→, cleavage site→, URA3, cleavage site→, DR(50 bp)→.

Due to the repeated sites in the xMarkers, creation of the DNA molecules required that the left half and the right half be constructed separately before joining the two halves. Construction of the markers described here used the "2nd Generation" strategy described above in section 6.2.

First, the left portion of the marker and the right portion of the marker were amplified separately by PCR. Four oligonucleotides were designed for PCR amplification of each xMarker: two "outer" oligonucleotides for PCR annealed to the ends of the marker and two "inner" oligonucleotides annealed inside the marker gene. The outer oligonucleotides contained 20-22 bp of sequence at the 3' end that was complementary to the template and 74-90 bp of sequence at the 5' end that did not anneal to the template and served to introduce the cleavage and scar sequences. The outer oligonucleotides were phosphorylated with PNK prior to inclusion in a PCR reaction, to facilitate ligation in later steps. The inner oligonucleotides were designed so that a middle segment of the marker was included in both the left and right PCR products, and so that this overlap segment included a unique restriction site that could be used to generate single-stranded, complementary overhangs. When possible, it was advantageous to choose restriction enzymes that generated non-palindromic overhangs, to reduce the likelihood of ligation of two left portions (or two right portions) together.

Second, the two PCR products were digested separately with the chosen restriction enzyme and gel-purified. Third, the left and right segments, each having a sticky end and a blunt end, were added the linearized RYSE 12 entry vector plasmid for a three-piece ligation. The left and right portions annealed and ligated using sticky ends, while the outermost ends of the marker construct participated in a blunt-ended ligation with the recipient plasmid. Individual clones of ligated plasmids were recovered and the desired plasmids were identified by DNA sequencing. These plasmids were new xMarker 12 RaBits that could be used for RYSE-based stitching of compound DNA constructs, just as previous 12 RaBits were used.

After the first set of xURA3 markers was tested, the F-CphI endonuclease was chosen for further work. Additional xMarkers with different selectable markers were made for use with F-CphI. This set included six different selection markers: URA3; hygromycin B phosphotransferase or hph; nourseothricin acetyltransferase or nat; aminoglycoside phosphotransferase or kan; zeocin resistance gene or ble; and phosphinothricin N-acetyltransferase or pat. These drug resistance genes from bacteria were all controlled by adjacent sequences corresponding to the promoter and terminator of the TEF1 gene from *Kluyveromyces lactis*, and the suffix "A" was appended to indicate this TEF1-derived regulatory control; the cassettes were then called hphA, natA, kanA, zeoA, and patA. Table 7 lists the restriction sites and the inner oligonucleotides for each marker; and Table 8 lists the outer oligonucleotides for each marker.

TABLE 7

Templates, restriction sites, and "inner" oligonucleotides used for construction of 3rd generation xMarkers

| Marker | Template for PCR | Internal restriction enzymes for 3-way ligations | reverse inner oligonucleotide (RIO) | forward inner oligonucleotide (FIO) |
|---|---|---|---|---|
| URA3 | RaBit 12-0-M-555 | BsiHKAI, PpuMI, BslI, or AlwNI | KB496-266-100 | KB495-266-100 |
| hphA | RaBit 12-0-M-21 | RsrII or BanI | KB492-266-100 | KB491-266-100 |
| kanA | RaBit 12-0-M-261 | BstXI | KB494-266-100 or TD_187 | KB493-266-100 or TD_186 |
| natA | RaBit 12-0-M-262 | StyI | KB479-266-81 | KB480-266-81 |
| zeoA | pAM1800 | BglI | TD_183 | TD_182 |
| patA | pAM1894 | TBD | TBD | TBD |

TABLE 8

"Outer" oligonucleotides used for construction of 3rd generation xMarkers

| Marker | scar | cleavage site | PCR template | forward outer oligo (FOO) | reverse outer oligo (ROO) |
|---|---|---|---|---|---|
| x0.URA.VDE | xM0 | VDE | RaBit 12-0-M-555 | KB518-266-135 | KB519-266-135 |
| x0.URA.PI-MgaI | xM0 | PI-MgaI | RaBit 12-0-M-555 | KB522-266-136 | KB523-266-136 |
| x0.URA.PI-MtuII | xM0 | PI-MtuII | RaBit 12-0-M-555 | KB524-266-136 | KB525-266-136 |
| x0.URA.F-Cph | xM0 | F-Cph | RaBit 12-0-M-555 | KB520-266-136 | KB521-266-136 |
| x1.natA.F-Cph | xM1 | F-Cph | RaBit 12-0-M-262 | MF51-312-97 | MF52-312-97 |
| x2.hphA.F-Cph | xM2 | F-Cph | RaBit 12-0-M-21 | MF53-312-98 | MF54-312-98 |
| x3.kanA.F-Cph | xM3 | F-Cph | RaBit 12-0-M-261 | TD_180 | TD_181 |
| x4.natA.F-Cph | xM4 | F-Cph | RaBit 12-0-M-262 | MF57-312-98 | MF58-312-98 |
| x6.zeoA.F-Cph | xM6 | F-Cph | pAM1800 | TD_176 | TD_177 |

6.1.5. Construction of Endonuclease Expression Plasmids

Table 9 below describes plasmids containing the endonuclease genes I-SceI, F-CphI, PI-MtuII (pps1), PI-MgaI (pps1) and VDE. The endonuclease genes were either chemically synthesized (I-SceI, F-CphI, PI-MtuII (pps1), PI-MgaI (pps1)) or amplified by PCR from *S. cerevisiae* genomic DNA (VDE).

TABLE 9

Plasmids containing endonuclease genes

| Plasmid | backbone | yeast marker | endonuclease | promoter | terminator |
|---|---|---|---|---|---|
| pAM1592 | pRS416 | URA3 | I-SceI | GAL1 | TDH3 |
| pAM1593 | pAM1110 | kanA | I-SceI | GAL1 | TDH3 |
| pAM1594 | pAM1111 | natA | I-SceI | GAL1 | TDH3 |
| pAM1595 | pAM1112 | hphA | I-SceI | GAL1 | TDH3 |
| pAM1677 | pAM1112 | hphA | VDE with N-terminal SV40 NLS | ACS2 | ADE6 |
| pAM1678 | pUC19 | none | PI-MgaI (pps1) with N-terminal SV40 NLS | none | none |
| pAM1679 | pUC19 | none | PI-MtuII (pps1) with N-terminal SV40 NLS | none | none |
| pAM1680 | pUC19 | none | F-CphI | none | none |
| pAM1749 | pAM1112 | hphA | F-CphI | ACS2 | ADE6 |
| pAM1750 | pAM1112 | hphA | PI-MgaI (pps1) with N-terminal SV40 NLS | ACS2 | ADE6 |
| pAM1751 | pAM1112 | hphA | PI-MtuII (pps1) with N-terminal SV40 NLS | ACS2 | ADE6 |
| pAM1799 | pAM1112 | hphA | F-CphI | GAL1 | TDH3 |
| pAM1800 | pAM1801/pAM1799 | zeoA | F-CphI | GAL1 | TDH3 |
| pAM1862 | pAM64 = pRS416 | URA3 | F-CphI | GAL1 | TDH3 |
| pAM1863 | pAM1110 | kanA | F-CphI | GAL1 | TDH3 |
| pAM1864 | pAM1111 | natA | F-CphI | GAL1 | TDH3 |
| pAM1865 | pAM1112 | hphA | PI-MtuII (pps1) with N-terminal SV40 NLS | GAL1 | TDH3 |
| pAM1866 | pAM1112 | hphA | PI-MgaI (pps1) with N-terminal SV40 NLS | GAL1 | TDH3 |
| pAM1867 | pAM1112 | hphA | VDE with N-terminal SV40 NLS | GAL1 | TDH3 |

Since three of the endonucleases (all but F-CphI and I-SceI) were too large (>25 kD; 353-456 amino acids) to freely travel through the nuclear pores from the intracellular site of synthesis (cytoplasm) to the site of action (nucleus), a DNA sequence was added to the 5' end of the coding sequence to append the SV40 nuclear localization sequence (NLS) to the amino-terminus of the protein. This NLS was described to be essential for the activity of VDE during mitotic (normal proliferative) growth in *S. cerevisiae*, since this native yeast enzyme naturally enters the nucleus only during meiosis. See, e.g., *Mol Cell Biol* 2003; 23:1726-36. The NLS was added to VDE using oligonucleotides with tails containing the coding sequence for the SV40 NLS; the NLS was added to PI-MtuII and PI-MgaI as part of the chemical syntheses of the entire genes. PCR-based "stitching" or "overlap extension" was used to fuse the endonuclease coding sequences, with or without NLS, with a promoter and a terminator. A first set of constructs was made with the *S. cerevisiae* promoter from ACS2 and the terminator from ADE6, without using the RYSE linkers. For this first set, the promoter-gene-terminator PCR stitching products were digested with SacI and XhoI, whose unique restriction sites had been introduced by tails on the oligonucleotides used for priming the PCR reactions of the individual pieces; then the constructs were ligated into the recipient plasmid that had been digested with SacI and XhoI and treated with phosphatase. A second set used the *S. cerevisiae* promoter from GAL1 and the terminator from TDH3; this set used the RYSE linkers and RYSE RaBits for the promoter (23-0-P-39) and terminator (45-0-T-64). For this second set of plasmids, the promoter-gene-terminator constructs were stitched with the RYSE primers RYSE4 and RYSE11 that had been previously phosphorylated using polynucleotide kinase (PNK), so that the blunt-ended stitched product could be efficiently ligated into a CEN.ARS plasmid with a yeast marker that had been linearized with a restriction enzyme that created blunt ended double-strand breaks. Finally, individual isolates of ligated plasmids were recovered and the desired plasmids were identified by DNA sequencing of the "promoter-gene-terminator" insert in the plasmid. The details of the plasmid construction are described below.

The recipient plasmids were all based on the "pRS" series of yeast-*E. coli* shuttle vectors with CEN.ARS sequences and yeast selectable markers, e.g., the URA3 marked version (pRS416 aka pAM64) was previously described (see, e.g., *Gene* 1992; 110:119-22; and *Genetics* 1989; 122:19-27). Derivatives of pRS416 were made by replacing the auxotrophic markers with the drug resistance markers kanA (pAM1110), natA (pAM1111), and hphA (pAM1112). For the second set of plasmids, pAM1112 was digested at a unique blunt-ended restriction site (EcoRV) within the polylinker/multiple cloning site, and then treated with phosphatase. The linearized vector was ligated to tripartite stitched PCR products that had been treated with polynucleotide kinase (PNK) to phosphorylate the 5' ends. For the first set of plasmids, the tripartite stitched PCR products and the pAM1112 recipient plasmid were both digested with XhoI and SacI and then mixed for ligation.

The "promoter-gene-terminator" PCR products for endonuclease gene expression were made by stitching together three pieces of DNA having overlapping ends. The oligonucleotides and templates used to create the three pieces, and the oligonucleotides used for stitching together the three pieces are shown in Table 10.

TABLE 10

Pieces used PCR stitches of promoter-endonuclease-terminator

| identity | promoter piece: oligos and template OR RaBit | endonuclease piece: oligos and template | terminator piece: oligos and template OR RaBit | priming oligos for stitching | treatment of stitched product prior to ligation |
|---|---|---|---|---|---|
| $P_{ACS2}$-VDE-$T_{ADE6}$ | KB510, KB512, genomic DNA (KB512 tail encodes NLS; KB510 tail introduces SacI site) | KB513, KB515, genomic DNA (KB513 tail encodes NLS) | KB514, KB511, genomic DNA (KB511 tail introduces XhoI site) | KB510, KB511 | digest with XhoI and SacI |
| $P_{ACS2}$-F-Cph-$T_{ADE6}$ | KB510, KB540, genomic DNA (KB510 tail introduces SacI site) | KB539, KB542, pAM1680 | KB541, KB511, genomic DNA (KB511 tail introduces XhoI site) | KB510, KB511 | digest with XhoI and SacI |
| $P_{ACS2}$-PI-MgaI-$T_{ADE6}$ | KB510, KB528, genomic DNA (KB510 tail introduces SacI site) | KB527, KB530, pAM1678 | KB529, KB511, genomic DNA (KB511 tail introduces XhoI site) | KB510, KB511 | digest with XhoI and SacI |
| $P_{ACS2}$-PI-MtuII-$T_{ADE6}$ | KB510, KB534, genomic DNA (KB510 tail introduces SacI site) | KB533, KB536, pAM1679 | KB535, KB511, genomic DNA (KB511 tail introduces XhoI site) | KB510, KB511 | digest with XhoI and SacI |
| $P_{GAL1}$-VDE-$T_{TDH3}$ | 23-0-P-39 | round 1: KB590, KB594, pAM1677; round 2: KB589, KB594, round 1 product | 45-0-T-64 | PNK-treated RYSE4, RYSE11 | none |
| $P_{GAL1}$-F-Cph-$T_{TDH3}$ | 23-0-P-39 | KB591, KB595, pAM1680 | 45-0-T-64 | PNK-treated RYSE4, RYSE11 | none |
| $P_{GAL1}$-PI-MgaI-$T_{TDH3}$ | 23-0-P-39 | KB589, KB593, pAM1678 | 45-0-T-64 | PNK-treated RYSE4, RYSE11 | none |
| $P_{GAL1}$-PI-MtuII-$T_{TDH3}$ | 23-0-P-39 | KB589, KB592, pAM1679 | 45-0-T-64 | PNK-treated RYSE4, RYSE11 | none |

6.1.6. Construction of I-SceI Expression Plasmids

The I-SceI gene was placed under control of the S. cerevisiae promoter for GAL1 and cloned into a set of CEN.ARS plasmids with various markers. The yeast-E. coli shuttle vectors with CEN.ARS sequences and LEU2 (pRS415 aka pAM63) and URA3 (pRS416 aka pAM63) markers were previously described (see, e.g., Gene 1992; 110:119-22; and Genetics 1989; 122:19-27). Derivatives of pRS416 were made by replacing the auxotrophic markers with the drug resistance markers kanA (pAM1110), natA (pAM1111), and hphA (pAM1112). Each of the vectors was digested at a unique blunt-ended restriction site within the polylinker/multiple cloning site, either EcoRV (drug resistance markers) or SmaI (URA3 and LEU2), and then treated with phosphatase. The linearized vectors were ligated to a tripartite stitched PCR product that had been treated with polynucleotide kinase (PNK) to phosphorylate the 5' ends. The PCR product was made by stitching together three pieces of DNA having overlapping ends using the oligonucleotide primers called RYSE4 and RYSE11: (1) the promoter from S. cerevisiae GAL1 with RYSE linkers 2 and 3, provided by a Sap1-liberated insert from RaBit 23-O—P-39, (2) the I-SceI coding sequence with RYSE linkers 3 and 4, provided by a PCR product from a custom-synthesized gene used as template and primers 00177-JD-75AN and 00177-JD-75AO, and (3) the terminator from S. cerevisiae TDH with RYSE linkers 4 and 5, provided by a Sap1-liberated insert from RaBit 45-0-T-64. Individual isolates of ligated plasmids were recovered and the desired plasmids were identified by DNA sequencing of the $P_{GAL1}$-I-SceI-$T_{TDH3}$ insert in the plasmid. The expression plasmids were called pAM1592 (URA3), pAM1593 (kanA), pAM1594 (natA), and pAM1595 (hphA). The $P_{GAL1}$ promoter is highly expressed when cells are grown in galactose and, in wild-type cells (GAL80+GAL4), is not expressed when cells are grown in glucose. However, in mutants lacking the GAL80 repressor (gal80Δ), $P_{GAL1}$ is expressed even in the absence of galactose; glucose repression of $P_{GAL1}$ is further reduced by addition of a GAL4 mutant with a promoter mutation, called GAL4$_{OC}$ (for Operator Constitutive).

Expression of the endonuclease was placed under the control of a strong promoter that was inducibly expressed in some host strain genetic backgrounds (GAL80+) and constitutively expressed in others (gal80Δ+/–GAL4$_{OC}$). Many other inducible promoters or constitutive promoters are expected to work well. Even if the promoter is constitutive, the expression of endonuclease can readily be eliminated after a desired time period by losing the plasmid; about half of the cells lose these plasmids after 10 generations in non-selective media (see, e.g., Gene 1992; 110:119-22; and Genetics 1989; 122:19-27).

6.1.7. Construction of F-CphI Expression Plasmids

After the F-CphI expression plasmid with the hphA marker (pAM1799) was made and tested, the $P_{GAL1}$-F-CphI-$T_{TDH3}$ cassette was subcloned into other CEN.ARS plasmids with different markers (pAM1110, pAM1111, pAM64) using the restriction enzymes XhoI and XbaI, each of which cleaved a unique site in the recipient plasmids and pAM1799. The plasmids were all cut with XhoI and XbaI, the plasmid vectors were treated with phosphatase, and the $P_{GAL1}$-F-CphI-$T_{TDH3}$ cassette was ligated with the other backbones. After ligation, the correct plasmid isolates were identified by restriction digestion.

The zeocin-resistance plasmid (pAM1800) was created by a method different from the others. Rather than stitch together the "promoter-gene-terminator" PCR product for $P_{GAL1}$-F-CphI-$T_{TDH3}$ and then ligate into a recipient plasmid with the zeocin resistance marker, the construction started with the F-CphI expression plasmid with the hphA marker (pAM1799) and exchanged the marker by exploiting yeast homologous recombination in vivo to substitute the zeocin resistance gene in place of the hygromycinB resistance gene. First, pAM1799 was linearized with NdeI, a restriction enzyme that cut a unique site in the hygromycin B resistance coding sequence. Second, the zeocin resistance gene was PCR-amplified from pAM1500 (or any Topo plasmid) using oligonucleotides with long tails (JU183 and JU184) that introduced sequence from the $P_{TEF}$ promoter and $T_{TEF}$ terminator that was homologous to the sequence in pAM1799 that controlled expression of the hph marker. Third, the two pieces of DNA were gel-purified and transformed into yeast for "gap repair" recombination that precisely replaced the hygromycin B resistance gene with the zeocin resistance gene. The correct plasmid was verified by DNA sequencing.

The $P_{GAL1}$ promoter is highly expressed when cells are grown in galactose and is not expressed when wild-type cells (with genotype GAL80 GAL4) are grown in glucose. However, in mutants lacking the GAL80 repressor (gal80Δ), $P_{GAL1}$ is expressed even in the absence of galactose; glucose repression of $P_{GAL1}$ is further reduced by addition of a GAL4 mutant with a promoter mutation, called GAL4$_{OC}$ (for Operator Constitutive). The $P_{ACS2}$ promoter is moderately expressed in all carbon sources.

6.2 Example 2

Excision of Selection Markers from Chromosomal DNA

This example demonstrates the utility of the xMarker constructs described in Example 1 in mediating excision of a selection marker from the chromosomal DNA of a host cell. As described below, the construct is transformed into cells, cells are plated on media selective for the xMarker, and the correct integration is confirmed by colony PCR; such strains perform just like any other strain made with a standard marker and the xMarker is stably maintained. Third, when the excision of the xMarker is desired, the strain is transformed with a single-copy (CEN.ARS) plasmid containing its own marker and an expression construct for the meganuclease gene. After growing under conditions that select for the presence of the plasmid for several generations and induce expression of the endonuclease gene, the strain is tested for loss of the xMarker. Finally, the strain is grown under conditions that permit loss of the meganuclease expression plasmid and isolates are tested for loss of the plasmid. At the end of this process, the strain is ready for re-use of the xMarkers.

For this strategy, it is essential that the xMarker is stable for a period of time sufficient for selection and verification of the cells that correctly integrated the desired DNA construct. High stability is ensured by using cells that lack the endonuclease gene until it is introduced by a second transformation. However, an alternative approach utilizes a host strain with a stably integrated endonuclease gene under the control of an inducible promoter. In this alternative scheme, the xMarker would be stable until the strain was cultured under conditions that induced expression of the endonuclease from the regulated promoter. If promoters with the desired characteristics are available, this approach would save time and effort required for transformation of the endonuclease plasmid.

Each xMarker contained the URA3 selectable marker gene flanked by two endonuclease cleavage sites, which in turn were flanked by a directly repeated sequence. For each, a knock-out construct with the structure GOI US/xMarker/GOI DS (GOI=gene of interest, US=upstream, DS=downstream) was stitched together using overlap extension PCR with three elements. The new-endonuclease URA3 xMarkers were initially tested in the context of an hxt3Δ construct. Each PCR reaction used as templates three RaBits liberated from their plasmid backbones by digestion with SapI: (1) HXT3 upstream (01-0-U-407), (2) an xMarker RaBit (x0.URA.VDE, x0.URA.F-CphI, 12-0-x0.URA.PI-MtuII, 12-0-x0.URA.PI-MgaI), and (3) HXT3 DS (29-0-D-408). The primers used for PCR stitching were RYSE0 and RYSE19. After PCR, the reaction mixture was loaded on an agarose gel and the desired full-length product was purified from the gel. Yeast cells were transformed with gel-purified PCR products and plated on selective plates (CSM-Uracil). Desired transformants had the mutant genotype hxt3Δ:: xURA3, with several versions of the xURA3 marker as listed in Table 6. Colonies that arose on the CSM-Uracil plates were tested for the presence of the desired chromosomal locus by PCR amplification of genomic DNA from cells lysed by boiling ("colony PCR") using primer pairs that amplified across the novel DNA junctions created by recombination. The primers were KB502, KB503, and CPK904; the latter two produced a 738 bp fragment for hxt3Δ::xURA3 and the former two produced a 538 bp fragment for intact HXT3. Two isolates for each xMarker variant were chosen for further analysis.

The xURA3 markers have the advantage of counterselection on 5-FOA plates, which permit growth only of cells lacking URA3. In contrast, isolates that have excised the other xMarkers must be identified by screening, e.g., replica plating from non-selective plates on which all isolates grow to selective plates on which the desired isolates fail to grow. The first generation xMarkers used URA3 to take advantage of counterselection, which permitted quantification of rare excision events. In accordance with expectation, when the strains containing xURA3 markers and lacking the endonuclease expression plasmids were plated or streaked onto 5-FOA, no colonies grew because the spontaneous excision of the xMarker was very rare in the absence of endonuclease-catalyzed cleavage. This suggested that without endonuclease expression the URA3 xMarker was rarely excised ($<10^{-6}$ of cells).

Isolates with the confirmed genotype hxt3Δ::xURA3 were transformed with the cognate expression plasmids for each endonuclease that were marked with hphA (pAM1799, pAM1865, pAM1866). Cells from transformation mixtures were allowed time to express the new marker gene (hphA) during outgrowth in liquid YPD for 3-6 hrs, then plated on YPD+hygromycinB plates. Since the host strain genotype was gal80Δ GAL4oc, the GAL1 promoter driving endonuclease gene expression was constitutively expressed and did not need an inducer. After three days growth, the transformant colonies were restreaked on YPD+hygromycinB plates and grown another three days. Colonies from the restreaks (four colonies per endonuclease) were resuspended in 3 ml of YPD and grown overnight in nonselective conditions to permit loss of the plasmids. Cell density was determined, cultures were diluted, and cells were plated at an estimated density of 150, 15,000, or 150,000 cells per plate on three different solid media: YPD, YPD+hygromycinB, and 5-FOA. All cells were expected to form colonies on YPD, only cells that had maintained the endonuclease expression plasmid were expected to form colonies on hygromycin B, and only cells that had excised the xURA3 marker were expected for form colonies on 5-FOA.

The results shown in Table 11 indicate that F-CphI mediated high efficiency xMarker excision, PI-MtuII mediated low efficiency xMarker excision, and PI-MgaI mediated undetectable levels of xMarker excision. The loss of the CEN.ARS endonuclease expression plasmids was a high frequency event, suggesting that it would be easy to isolate cells that had lost the endonuclease prior to another round of transformations with new xMarkers.

TABLE 11

Results comparing xMarker excision efficiency of different endonucleases and frequency of loss of expression plasmid after several generations of non-selective growth

| Endonuclease | % of cells that lost xURA3 Marker | % of cells that lost hphA-marked endonuclease expression plasmid |
| --- | --- | --- |
| F-CphI | 90.8% | 31.9% |
| PI-MgaI | 0.058% | 76.5% |
| PI-MtuII | <0.0007% | ND |
| VDE | ND | ND |

To determine if the F-CphI mediated excision of the marker left behind a "perfect" scar, the 5-FOA resistant (functionally ura3⁻) colonies were subjected to colony PCR using oligonucleotide primers that flanked the integration site of the xURA3 marker (oligonucleotides KB503 and KB604); the 533 bp PCR product was sent for DNA sequencing with oligonucleotide primer KB503. Of 16 colonies tested, all had a "perfect" scar in which the only DNA sequence remaining from the xMarker was a single copy of the 50 bp sequence.

Additional xMarkers with F-CphI cleavage sites and various selectable markers were created and tested (natA, kanA, hphA, zeoA). The excision frequencies and fidelities of excision of these markers were tested in haploid and diploid *S. cerevisiae* strains, both singly and in combinations. The frequency of excision was often 100% of the colonies tested and always >80%. The fidelity of excision was nearly 100%. Almost all of the excision events in many independent cultures gave the expected scar; excision left behind only one copy of the 50 bp unique sequence that was introduced as a direct repeat in the xMarker and the marker itself was absent (Table 12).

TABLE 12 xMarker excision frequencies for different endonucleases and DRs of at least 50 bp length

| | | | | | xMarker Excision | | | Excision Precision | |
|---|---|---|---|---|---|---|---|---|---|
| Endo-nuclease | Length of DR (bp) | # of ES's | xMarker Targeting Construct | Endo-nuclease Expression Plasmid | # of Cells Tested[a] | # of Cells with Excised xMarker | Excision Frequency | # of Cells Tested | # of Cells with Perfect Scar[b] |
| F-CphI | 50 | 2 | HXT3-US_xM0.URA.F-CphI_HXT3-DS | pAM1799 | 402 | 365 | 0.91 | ND | ND |
| | 50 | 2 | GAL80-US_xM0.URA.F-CphI_GAL80-DS | pAM1800 | 8 | 8 | 1 | 8 | 8 |
| | 50 | 2 | GAL80-US_xM1.nat.F-CphI_GAL80-DS | pAM1800 | 16 | 16 | 1 | 8 | 8 |
| | 50 | 2 | GAL80-US_xM3.kan.F-CphI_GAL80-DS | pAM1800 | 8 | 8 | 1 | 8 | 8 |
| | 50 | 2 | GAL80-US_xM4.nat.F-CphI_GAL80-DS | pAM1800 | 8 | 8 | 1 | 8 | 8 |
| | 50 | 2 | GAL80-US_xM6.zeo.F-CphI_GAL80-DS | pAM1862/pAM1864 | 16 | 16 | 1 | 16 | 16 |
| PI-MgaI | 50 | 2 | HXT3-US_xM0.URA.PI-MgaI_HXT3-DS | pAM1866 | ~6.6 × 10$^5$ | 0 | <1.5 × 10$^{-6}$ | ND | ND |
| PI-MtuII | 50 | 2 | HXT3-US_xM0.URA.PI-MtuII_HXT3-DS | pAM1865 | ~6.6 × 10$^5$ | 419 | 6.3 × 10$^{-4}$ | ND | ND |
| VDE | 50 | 2 | HXT3-US_xM0.URA.VDE_HXT3-DS | pAM1677 | 535 | 9 | 1.7 × 10$^{-2}$ | ND | ND |
| I-SceI | 60 | 2 | NDT80-US_s60M.URA.I-SceI_NDT80-DS | pAM1595 | 288 | 155 | 0.54 | 4 | 4 |
| | 80 | 2 | NDT80-US_s80M.URA.I-SceI_NDT80-DS | pAM1595 | 237 | 76 | 0.32 | 8 | 8 |

[a]Number of colonies on YPD plates, adjusted by dilution factor.
[b]Perfect scar = after excision only DNA sequence remaining from the xMarker is a single copy of the DR sequence.
ND = not determined.

Strains with xMarkers at the NDT80 locus (deleting the NDT80 gene) were made as follows. The stitched PCR product used to transform cells was made by stitching the xMarker (as a 12 RaBit) with the 01-0-U-97 and 29-0-U-23 RaBits with the oligonucleotides called RYSE0 and RYSE19. After transformation, the identity of the correct isolates was verified by colony PCR using a pair of oligonucleotides in which one was outside of the transformed DNA (CPK650) and the other was inside the marker (e.g., KB561 and KB562 for URA3; KB563 and KB564 for natA, kanA, and hygA), which gave a PCR product of ~1.1 kb. The removal of native NDT80 sequence was verified by the absence of a PCR product from colony PCR with oligonucleotides AET83 and AET84, which gave a PCR product of 442 bp from the parental strain with an intact NDT80 locus. After transformation with a F-CphI expression plasmid (pAM1800), individual colonies were tested for the intended excision by colony PCR with JU197 and JU198, which gave a band of 492 bp for a perfect excision that left behind only one copy of the 50 bp scar sequence; this band was run on a gel to visualize and separate from any other DNA, then extracted from the gel and sent for DNA sequencing using the same oligonucleotides used to prime the PCR reaction.

Strains with xMarkers at the GAL80 locus (deleting the GAL80 gene) were made as follows. The stitched PCR product used to transform cells was made by stitching the xMarker (as a 12 RaBit) with the 01-0-U-270 and 29-0-U-95 RaBits with the oligonucleotides called RYSE0 and RYSE19. After transformation, the identity of the correct isolates was verified by colony PCR. Oligonucleotides JU436 and RYSE3 amplified the vicinity around the 5' junction where the transformed DNA integrated within the GAL80 upstream sequence to give a PCR product of 572 bp (alternatively, JU210 and RYSE3 were used to give a PCR product of 182 bp); JU221 and RYSE4 gave a 386 bp product from amplification of the 3' junction of the marker with the GAL80 downstream sequence by (alternatively, JU439 and RYSE4 were used to give a PCR product of 531 bp); a negative control was colony PCR with primers JU212 and JU210, which gave a 290 bp product for an intact GAL80 locus and no product for the desired locus. After transformation with a F-CphI expression plasmid (pAM1800 or pAM1799), individual colonies were tested for the intended excision by colony PCR with JU210 and JU211, which gave a band of 277 bp for a perfect excision that left behind only one copy of the 50 bp scar sequence; this band was run on a gel to visualize and separate from any other DNA, then extracted from the gel and sent for DNA sequencing using the same oligonucleotides used to prime the PCR reaction.

After transformation with an expression plasmid for F-CphI, eight of the colonies that arose on selective plates were randomly selected for colony PCR to diagnose excision. For the following xMarkers all eight colonies gave the expected PCR product and the DNA sequencing verified perfect scars: x0URA3, x1nat, x3kan, x4nat, and x6zeo. The x2hph marker gave anomalous results; sequencing of the scars and resequencing xMarker (the 12 RaBit) revealed that the direct repeats were not as intended, and instead only 19 bp were directly repeated flanking the marker with a scrambling of the adjacent sequences. Despite the small region provided for repair of the double-stranded break the excision frequency and fidelity was good; in the first trial, six out of eight colonies had clearly excised the marker and left behind scars of variable lengths; in the second trial, eight of eight colonies had excised the marker and left behind scars of 19 bp. This suggests that 17-18 bp would be sufficient for the direct repeat length, and 50 bp is more than enough to guide repair of the chromosome after cleavage by F-CphI.

High frequency and precision of excision of the xMarkers was observed in several circumstances. The simplest circumstance was a single xMarker in each strain. A more complicated circumstance was excision of an xMarker in a heterozygous diploid strain that had one intact GAL80 allele and one allele that had been deleted by an xMarker; in this case, the intact GAL80 locus remained intact after the excision of the xMarker at the disrupted allele. This is important, because it might have happened that the cleaved chromosome ends near the xMarker, after action of the F-CphI, could have used the intact second copy of the chromosome as a template for repair, thereby leading to a gene conversion event that would restore the intact GAL80 locus to the chromosome from which it had been deleted. This gene conversion event was not seen, and instead the cell apparently preferentially repaired the broken chromosome by an intrachromosomal single-stranded annealing mechanism.

Perhaps the most challenging (and useful) circumstance is simultaneous excision of more than one xMarker from the same strain, where each xMarker was used to mark a different integration into a different locus. In a trial of excision of two markers from a single haploid strain, there was no evidence for chromosomal translocation or genomic instability and there was a high frequency of perfect excision (8 of 8 colonies tested). Thus, it does not appear that excision of multiple markers in a single strain will lead to widespread and high frequency genomic instability.

These results demonstrate that the compositions and methods described herein, for creating and excising specialized variants of selectable markers, work with high frequency, efficiency, and fidelity. The I-SceI and F-CphI endonucleases work well for this approach, with F-CphI showing unexpectedly exceptional excision frequency and fidelity. The excision events themselves do not cause genomic instability even in diploid cells and even in cells with more than one xMarker. Major advantages of this approach include the ability to simultaneously excise many xMarkers at once and the ability to choose a large variety of unique scar sequences, such that even repeated use and recycling of xMarkers in the same strain can be designed such that each scar is unique. This is an advantage over Flp/FRT or Cre/lox systems that necessarily leave behind multiple copies of the binding and cleavage site for the site-specific recombinase, littered throughout the genome, waiting to be cleaved again upon re-introduction of the recombinase, which potentially causes translocations and excisions of chromosome segments. Another advantage is that the excision frequency is often higher than 50% and thus the approach can be used to excise any desired target DNA, using a screening approach to identify the desired product strains, even when there is no selection method available to permit growth only of the successfully excised product isolates. This demonstration of the basics of this approach proves that it is a useful and easy method, with high frequency and fidelity. It can readily be extended to more complex applications, such as triggering a permanent switch for gene expression.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. An excisable nucleic acid construct comprising, in a 5' to 3' orientation:
   (a) a first tandem repeat nucleic acid;
   (b) a first F-CphI endonuclease recognition site;
   (c) a target nucleic acid;
   (d) a second F-CphI endonuclease recognition site; and
   (e) a second tandem repeat nucleic acid.

2. The excisable nucleic acid construct of claim 1, wherein each of the first and second tandem repeat nucleic acids independently comprises 18-80 nucleotide base pairs.

3. The excisable nucleic acid construct of claim 1, wherein the target nucleic acid encodes a selectable marker.

4. The excisable nucleic acid construct of claim 3, wherein the selectable marker is selected from the group consisting of: URA3, hygromycin B phosphotransferase, aminoglycoside phosphotransferase, zeocin resistance gene and phosphinothricin N-acetyltransferase.

5. The excisable nucleic acid construct of claim 1, further comprising a first integration site linked 5' of the first homing endonuclease recognition site and a second integration site linked 3' of the second tandem repeat nucleic acid.

6. The excisable nucleic acid construct of claim 1, wherein the target nucleic acid comprises a promoter element operably linked to a nucleic acid encoding F-CphI endonuclease.

7. A host cell comprising:
   (a) the excisable nucleic acid construct of claim 1; and
   (b) a vector comprising a nucleic acid encoding F-CphI endonuclease.

8. The host cell of claim 7, wherein the vector comprises a promoter element that controls the expression of the nucleic acid encoding F-CphI endonuclease.

9. The host cell of claim 8, wherein the promoter element is an inducible promoter.

10. The host cell of claim 7 that is a yeast cell.

11. The host cell of claim 10 that is a haploid yeast cell.

12. The host cell of claim 10 that is a diploid yeast cell.

13. The host cell of claim 10 that is a *Saccharomyces cerevisiae* cell.

14. The host cell of claim 7, wherein the excisable nucleic acid construct is integrated into the host cell genome.

15. A method of excising at least one target nucleic acid from the genome of a host cell comprising the excisable nucleic acid construct of claim 1, wherein the method comprises: contacting the excisable nucleic acid construct with F-CphI in the host cell.

16. The method of claim 15, wherein said excising operably links a promoter element to a gene of interest.

17. The method of claim 15, wherein the host cell is a yeast cell.

18. The method of claim 15, wherein the host cell is a haploid yeast cell.

19. The method of claim 15, wherein the host cell is a diploid yeast cell.

20. The method of claim 15, wherein the host cell is a *Saccharomyces cerevisiae* cell.

* * * * *